US009765402B2

(12) United States Patent
Mayer-Blackwell et al.

(10) Patent No.: US 9,765,402 B2
(45) Date of Patent: Sep. 19, 2017

(54) NANOLITER QPCR PLATFORM FOR PARALLEL QUANTITATIVE ASSESSMENT OF REDUCTIVE DEHALOGENASE GENES

(71) Applicant: The Board of Trustees of the Leland Stanford Junior University, Palo Alto, CA (US)

(72) Inventors: Koshlan Mayer-Blackwell, Stanford, CA (US); Alfred M. Spormann, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 145 days.

(21) Appl. No.: 14/661,050

(22) Filed: Mar. 18, 2015

(65) Prior Publication Data

US 2015/0267265 A1 Sep. 24, 2015

Related U.S. Application Data

(60) Provisional application No. 61/968,578, filed on Mar. 21, 2014.

(51) Int. Cl.
*C12Q 1/68* (2006.01)
(52) U.S. Cl.
CPC .................... *C12Q 1/689* (2013.01)
(58) Field of Classification Search
None
See application file for complete search history.

(56) References Cited

FOREIGN PATENT DOCUMENTS

| EP | 0864542 A2 * | 9/1998 | ............ C02F 3/2806 |
| JP | 2010119340 A * | 6/2010 | |

OTHER PUBLICATIONS

Maphosa et al. (Exploiting the ecogenomics toolbox for environmental diagnostics of organohalide-respiring bacteria, Trends Biotechnol. Jun. 2010;28(6):308-16. doi: 10.1016/j.tibtech.2010.03.005. Epub Apr. 29, 2010).*
Buttet et al. (Functional Genotyping of Sulfurospirillum spp. in Mixed Cultures Allowed the Identification of a New Tetrachloroethene Reductive Dehalogenase, Appl. Environ. Microbiol. Nov. 2013 vol. 79 No. 22 6941-6947, Accepted manuscript posted online Aug. 30, 2013).*
Nolan et al. (Quantification of mRNA using real-time RT-PCR, Nature Protocols, vol. 1, No. 3, Nov. 9, 2006).*
Untergasser et al. (Primer3Plus, an enhanced web interface to Primer3, Nucleic Acids Research, 2007, vol. 35, 2007).*
Rozen et al. (Primer3 on the WWW for General Users and for Biologist Programmers, in Methods in Molecular Biology, vol. 132: Bioinformatics Methods and Protocols, 2000)).*
Buck ("Design Strategies and Performance of Custom DNA Sequencing Primers" Biotechniques. 1999. 27(3): pp. 528-536).*
Lowe (Nucleic Acids Research, vol. 18, No. 7, p. 1757-1761, 1990).*
Kimoto et al. (Cloning of a novel dehalogenase from environmental DNA, Biosci Biotechnol Biochem. 2010;74(6):1290-2. Epub Jun. 7, 2010).*
Neumann et al. (Tetrachloroethene dehalogenase from Dehalospirillum multivorans: cloning, sequencing of the encoding genes, and expression of the pceA gene in *Escherichia coli*, J Bacteriol. Aug. 1998;180(16):4140-5).*
Schoville et al. (Investigating the molecular basis of local adaptation to thermal stress: population differences in gene expression across the transcriptome of the copepod Tigriopus californicus, BMC Evol Biol. Sep. 5, 2012;12:170. doi: 10.1186/1471-2148-12-170).*
von Wintzingerode et al. (Development of primers for amplifying genes encoding CprA- and PceA-like reductive dehalogenases in anaerobic microbial consortia, dechlorinating trichlorobenzene and 1,2-dichloropropane, FEMS Microbiol Ecol. Apr. 2001;35(2):189-196).*
Chow et al. (Identification and transcriptional analysis of trans-DCE-producing reductive dehalogenases in *Dehalococcoides* species, ISME J. Aug. 2010;4(8):1020-30. doi: 10.1038/ismej.2010.27. Epub Apr. 1, 2010).*
Hug et al. (Diversity of reductive dehalogenase genes from environmental samples and enrichment cultures identified with degenerate primer PCR screens, Front Microbiol. Nov. 19, 2013;4:341. doi: 10.3389/fmicb.2013.00341. eCollection 2013).*
Rhee et al. (Detection by PCR of reductive dehalogenase motifs in a sulfidogenic 2-bromophenol-degrading consortium enriched from estuarine sediment, FEMS Microbiology Ecology 43 (2003) 317-324, First published online Nov. 23, 2002).*
Behrens et al., (2008) Monitoring Abundance and Expression of "*Dehalococcoides*" Species Chloroethene-Reductive Dehalogenases in a Tetrachloroethene-Dechlorinating Flow Column. Appl. Environ. Microbiol. 74: 5695-5703.
Berggren et al., (2013) Effects of Sulfate Reduction on the Bacterial Community and Kinetic Parameters of a Dechlorinating Culture under Chemostat Growth Conditions. Environ. Sci. & Technol. 47: 1879-1886.
Bouwer et al., (1983) Transformations of Trace Halogenated Aliphatics in Anoxic Biofilm Columns. Appl. Environ. Microbiol. 45: 1286-1294.
Caccavo et al., (1994) *Geobacter sulfurreducens* sp. nov., a Hydrogen- and Acetate-Oxidizing Dissimilatory Metal-Reducing Microorganism. Appl. Environ. Microbiol. 60: 3752-3759.
Cupples & Spormann (2004) Vinyl Chloride and cis-Dichloroethene Dechlorination Kinetics and Microorganism Growth under Substrate Limiting Conditions. Environ. Sci. & Technol. 38: 1102-1107.
De Wildeman et al., (2003) Stereoselective Microbial Dehalorespiration with Vicinal Dichlorinated Alkanes. Appl. Environ. Microbiol. 69: 5643-5647.

(Continued)

*Primary Examiner* — Aaron Priest
(74) *Attorney, Agent, or Firm* — Thomas | Horstemeyer, LLP

(57) ABSTRACT

Combinations of reductive dehalogenase (rdh) genes are a distinguishing genomic feature of closely-related organohalogen-respiring bacteria. This feature can be used to deconvolute the population structure of organohalogen-respiring bacteria in complex environments and to identify relevant subpopulations, which is important for tracking interspecies dynamics needed for successful site remediation. The present disclosure encompasses embodiments of a nanoliter qPCR platform to identify organohalogen-respiring bacteria by quantitatively identifying major orthologous reductive dehalogenase gene groups.

13 Claims, 11 Drawing Sheets

(56) References Cited

OTHER PUBLICATIONS

DiStefano et al., (1991) Reductive Dechlorination of High Concentrations of Tetrachloroethene to Ethene by an Anaerobic Enrichment Culture in the Absence of Methanogenesis. Appl. Environ. Microbiol. 57: 2287-2292.

Grostern et al., (2009) Characterization of a Dehalobacter Coculture That Dechlorinates 1,2-Dichloroethane to Ethene and Identification of the Putative Reductive Dehalogenase Gene. Appl. Environ. Microbiol. 75: 2684-2693.

He et al. (2003) Complete Detoxification of Vinyl Chloride by an Anaerobic Enrichment Culture and Identification of the Reductively Dechlorinating Population as a *Dehalococcoides* Species. Appl. Environ. Microbiol. 65: 485-49.

He et al., (2003) Detoxification of vinyl chloride to ethene coupled to growth of an anaerobic bacterium. Nature 424: 62-65.

Heid et al., (1996) Real Time Quantitative PCR. Genome Res. 6: 986-994.

Hendrickson et al., (2002) Molecular Analysis of Dehalococcoides 16S Ribosomal DNA from Chloroethene Contaminated Sites throughout North America and Europe. Appl. Environ. Microbiol. 68: 485-495.

Hug et al., (2011) Molecular Analysis of Dehalococcoides 16S Ribosomal DNA from Chloroethene-Contaminated Sites throughout North America and Europe. Appl. Environ. Microbiol. 77, 5361-5369.

Hug et al., (2012) Comparative metagenomics of three Dehalococcoides-containing enrichment cultures: the role of the non-dechlorinating community. BMC Genomics 13, 327.

Hug et al., (2013) Overview of organohalide-respiring bacteria and a proposal for a classification system for reductive dehalogenases. Philo. Trans. Roy. Soc. B: Biol. Sci. 368: 20120322-20120322.

Kube et al., (2005) Genome sequence of the chlorinated compound—respiring bacterium *Dehalococcoides* species strain CBDB1. Nat Biotechnol. 23: 1269-1273.

Lee et al., (2012) Global Transcriptomic and Proteomic Responses of Dehalococcoides ethenogenes Strain 195 to Fixed Nitrogen Limitation. Appl. Environ. Microbiol. 78: 1424-1436.

Maphosa et al., (2010) Exploiting the ecogenomics toolbox for environmental diagnostics of organohalide-respiring bacteria. Trends Biotechnol. 28: 308-316.

Marshall et al., (2012) The Hydrogenase Chip: a tiling oligonucleotide DNA microarray technique for characterizing hydrogen-producing and -consuming microbes in microbial communities. ISME J. 6: 814-826.

Marshall et al., (2014) Inferring community dynamics of organohalide-respiring bacteria in chemostats by covariance of rdhA gene abundance. FEMS Microbiol Ecol. 86: 428-440.

Marzorati et al., (2007) A Novel Reductive Dehalogenase, Identified in a Contaminated Groundwater Enrichment Culture and in *Desulfitobacterium dichloroeliminans* Strain DCA1, Is Linked to Dehalogenation of 1,2-Dichloroethane. Appl. Environ. Microbiol. 73: 2990-2999.

McMurdie et al., (2009) Localized Plasticity in the Streamlined Genomes of Vinyl Chloride Respiring Dehalococcoides. PLoS Genet. 5, e1000714.

Men et al., (2013) Characterization of four TCE-dechlorinating microbial enrichments grown with different cobalamin stress and methanogenic conditions. Appl. Microbiol. Biotechnol. 97: 6439-6450.

Moe et al., (2009) *Dehalogenimonas lykanthroporepellens* gen. nov., sp. nov., a reductively dehalogenating bacterium isolated from chlorinated solvent-contaminated groundwater. Int. J. Syst. Evol. Microbiol. 59: 2692-2697.

Morrison et al., (2006) Nanoliter high throughput quantitative PCR. Nucl. Acids Res. 34: e123-e123.

Müller et al., (2004) Molecular Identification of the Catabolic Vinyl Chloride Reductase from *Dehalococcoides* sp. Strain VS and Its Environmental Distribution. Appl. Environ. Microbiol. 70: 4880-4888.

Punta et al., (2012) The Pfam protein families database. Nucl. Acids Res. 40: D290-D301.

Rice et al., (2000) EMBOSS: The European Molecular Biology Open Software Suite in Trends in Genetics 16: 276-277.

Rodriguez-Valera et al., (2009) Explaining microbial population genomics through phage predation. Nat. Rev. Microbiol. 7: 828-836.

Rowe et al., (2012) Methanospirillum Respiratory mRNA Biomarkers Correlate with Hydrogenotrophic Methanogenesis Rate during Growth and Competition for Hydrogen in an Organochlorine-Respiring Mixed Culture. Environ. Sci. & Technol. 46: 9388-9397.

Rozen & Skaletsky (2000) Primer3 on the WWW for General Users and for Biologist Programmers. Methods Mol. Biol. 132: 365-386.

Seshadri et al., (2005) Genome Sequence of the PCE-Dechlorinating Bacterium Dehalococcoides ethenogenes. Science 307: 105-108.

Sung et al., (2006) Quantitative PCR Confirms Purity of Strain GT, a Novel Trichloroethene-to-Ethene-Respiring Dehalococcoides Isolate. Appl. Environ. Microbiol. 72: 1980-1987.

Sung et al., (2006) *Geobacter lovleyi* sp. nov. Strain SZ, a Novel Metal-Reducing and Tetrachloroethene-Dechlorinating Bacterium. Appl. Environ. Microbiol. 72: 2775-2782.

Suyama et al., (2002) Molecular Characterization of the PceA Reductive Dehalogenase of *Desulfitobacterium* sp. Strain Y51. J. Bacteriol. 184: 3419-3425.

Wagner et al., (2012) Genomic determinants of organohalide-respiration in Geobacter lovleyi, an unusual member of the Geobacteraceae. BMC Genomics. 13: 200.

Ziv-El et al., (2012) Managing Methanogens and Homoacetogens to Promote Reductive Dechlorination of Trichloroethene With Direct Delivery of H2 in a Membrane Biofilm Reactor. Biotechnol. Bioeng. 109: 2200-2210.

\* cited by examiner

SEQUENCE LISTING

<160> NUMBER OF SEQ ID NOS: 366

<210> SEQ ID NO 1
<211> LENGTH: 20
<212> TYPE: DNA
<213> ORGANISM: Artificial sequence
<220> FEATURE:
<223> OTHER INFORMATION: Primer AAC60788.1_378_ext_F_1302

<400> SEQUENCE: 1
tggattcatg atggcgttga          20

```
<210> SEQ ID NO 2
<211> LENGTH: 20
<212> TYPE: DNA
<213> ORGANISM: Artificial sequence
<220> FEATURE:
<223> OTHER INFORMATION: Primer AAC60788.1_378_ext_R_1391

<400> SEQUENCE: 2
accatagccc aatgcatcat                                                     20

<210> SEQ ID NO 3
<211> LENGTH: 20
<212> TYPE: DNA
<213> ORGANISM: Artificial sequence
<220> FEATURE:
<223> OTHER INFORMATION: Primer AAC60788.1_624_ext_F_1302

<400> SEQUENCE: 3
tggattcatg atggcgttga                                                     20

<210> SEQ ID NO 4
<211> LENGTH: 21
<212> TYPE: DNA
<213> ORGANISM: Artificial sequence
<220> FEATURE:
<223> OTHER INFORMATION: Primer AAC60788.1_624_ext_R_1384

<400> SEQUENCE: 4
cccaatgcat catccatacc a                                                   21

<210> SEQ ID NO 5
<211> LENGTH: 20
<212> TYPE: DNA
<213> ORGANISM: Artificial sequence
<220> FEATURE:
<223> OTHER INFORMATION: Primer AAD44542.1_105_ext_F_984

<400> SEQUENCE: 5
ttctgccggg tatgcaaaaa                                                     20

<210> SEQ ID NO 6
<211> LENGTH: 20
<212> TYPE: DNA
<213> ORGANISM: Artificial sequence
<220> FEATURE:
<223> OTHER INFORMATION: Primer AAD44542.1_105_ext_R_1086

<400> SEQUENCE: 6
cactgttcca acgcaggtat                                                     20

<210> SEQ ID NO 7
<211> LENGTH: 20
<212> TYPE: DNA
<213> ORGANISM: Artificial sequence
<220> FEATURE:
<223> OTHER INFORMATION: Primer AAD44542.1_11_spec_F_1016

<400> SEQUENCE: 7
ttgtccaaac gacgcgatta                                                     20

<210> SEQ ID NO 8
<211> LENGTH: 20
<212> TYPE: DNA
<213> ORGANISM: Artificial sequence
<220> FEATURE:
```

<223> OTHER INFORMATION: Primer AAD44542.1_11_spec_R_1091

<400> SEQUENCE: 8
aaagtcactg ttccaacgca                                               20

<210> SEQ ID NO 9
<211> LENGTH: 20
<212> TYPE: DNA
<213> ORGANISM: Artificial sequence
<220> FEATURE:
<223> OTHER INFORMATION: Primer AAD44542.1_1304_ext_F_1067

<400> SEQUENCE: 9
atacctgcgt tggaacagtg                                               20

<210> SEQ ID NO 10
<211> LENGTH: 20
<212> TYPE: DNA
<213> ORGANISM: Artificial sequence
<220> FEATURE:
<223> OTHER INFORMATION: Primer AAD44542.1_1304_ext_R_1201

<400> SEQUENCE: 10
cctgctttat ggaaccagga                                               20

<210> SEQ ID NO 11
<211> LENGTH: 20
<212> TYPE: DNA
<213> ORGANISM: Artificial sequence
<220> FEATURE:
<223> OTHER INFORMATION: Primer AAD44542.1_14_spec_F_742

<400> SEQUENCE: 11
gctgcattgc cgtcattatg                                               20

<210> SEQ ID NO 12
<211> LENGTH: 20
<212> TYPE: DNA
<213> ORGANISM: Artificial sequence
<220> FEATURE:
<223> OTHER INFORMATION: Primer AAD44542.1_14_spec_R_868

<400> SEQUENCE: 12
gacaattctc ccagacctgc                                               20

<210> SEQ ID NO 13
<211> LENGTH: 20
<212> TYPE: DNA
<213> ORGANISM: Artificial sequence
<220> FEATURE:
<223> OTHER INFORMATION: Primer AAD44542.1_43_ext_F_849

<400> SEQUENCE: 13
gcaggtctgg gagaattgtc                                               20

<210> SEQ ID NO 14
<211> LENGTH: 20
<212> TYPE: DNA
<213> ORGANISM: Artificial sequence
<220> FEATURE:
<223> OTHER INFORMATION: Primer AAD44542.1_43_ext_R_934

<400> SEQUENCE: 14
gtcgttactg cggctacttt                                               20

<210> SEQ ID NO 15
<211> LENGTH: 20
<212> TYPE: DNA
<213> ORGANISM: Artificial sequence
<220> FEATURE:
<223> OTHER INFORMATION: Primer AAD44542.1_7_spec_F_572

<400> SEQUENCE: 15
tacagtcgga ctcatgagca                                               20

<210> SEQ ID NO 16
<211> LENGTH: 20
<212> TYPE: DNA
<213> ORGANISM: Artificial sequence
<220> FEATURE:
<223> OTHER INFORMATION: Primer AAD44542.1_7_spec_R_766

<400> SEQUENCE: 16
ttggccataa tgacggcaat                                               20

<210> SEQ ID NO 17
<211> LENGTH: 20
<212> TYPE: DNA
<213> ORGANISM: Artificial sequence
<220> FEATURE:
<223> OTHER INFORMATION: Primer AAQ54585.2_1_spec_F_576

<400> SEQUENCE: 17
gtgtttctgg cgggaatgta                                               20

<210> SEQ ID NO 18
<211> LENGTH: 20
<212> TYPE: DNA
<213> ORGANISM: Artificial sequence
<220> FEATURE:
<223> OTHER INFORMATION: Primer AAQ54585.2_1_spec_R_748

<400> SEQUENCE: 18
gtccagcgat cgtcataagg                                               20

<210> SEQ ID NO 19
<211> LENGTH: 20
<212> TYPE: DNA
<213> ORGANISM: Artificial sequence
<220> FEATURE:
<223> OTHER INFORMATION: Primer AAQ54585.2_1053_ext_F_1446

<400> SEQUENCE: 19
tgctcctgga acaaaatcga                                               20

<210> SEQ ID NO 20
<211> LENGTH: 20
<212> TYPE: DNA
<213> ORGANISM: Artificial sequence
<220> FEATURE:
<223> OTHER INFORMATION: Primer AAQ54585.2_1053_ext_R_1544

<400> SEQUENCE: 20
ccactcatcg aacttacggg                                               20

<210> SEQ ID NO 21
<211> LENGTH: 20
<212> TYPE: DNA
<213> ORGANISM: Artificial sequence
<220> FEATURE:
<223> OTHER INFORMATION: Primer AAQ54585.2_1536_ext_F_1292

```
<400> SEQUENCE: 21
ggcgatctcc catgtgaaag                                               20

<210> SEQ ID NO 22
<211> LENGTH: 20
<212> TYPE: DNA
<213> ORGANISM: Artificial sequence
<220> FEATURE:
<223> OTHER INFORMATION: Primer AAQ54585.2_1536_ext_R_1474

<400> SEQUENCE: 22
tgccaggcat cgattttgtt                                               20

<210> SEQ ID NO 23
<211> LENGTH: 20
<212> TYPE: DNA
<213> ORGANISM: Artificial sequence
<220> FEATURE:
<223> OTHER INFORMATION: Primer AAQ54585.2_3115_ext_F_1203

<400> SEQUENCE: 23
ttggaacttg ttccggacaa                                               20

<210> SEQ ID NO 24
<211> LENGTH: 20
<212> TYPE: DNA
<213> ORGANISM: Artificial sequence
<220> FEATURE:
<223> OTHER INFORMATION: Primer AAQ54585.2_3115_ext_R_1316

<400> SEQUENCE: 24
ggggtctttc acatgggaga                                               20

<210> SEQ ID NO 25
<211> LENGTH: 20
<212> TYPE: DNA
<213> ORGANISM: Artificial sequence
<220> FEATURE:
<223> OTHER INFORMATION: Primer AAR24308.1_0_spec_F_235

<400> SEQUENCE: 25
gcaaaacaga aagcagaccg                                               20

<210> SEQ ID NO 26
<211> LENGTH: 20
<212> TYPE: DNA
<213> ORGANISM: Artificial sequence
<220> FEATURE:
<223> OTHER INFORMATION: Primer AAR24308.1_0_spec_R_352

<400> SEQUENCE: 26
catgtgaaaa acctgcctgc                                               20

<210> SEQ ID NO 27
<211> LENGTH: 20
<212> TYPE: DNA
<213> ORGANISM: Artificial sequence
<220> FEATURE:
<223> OTHER INFORMATION: Primer AAR24308.1_4_spec_F_183

<400> SEQUENCE: 27
tcaagttgcg tatgccagtt                                               20

<210> SEQ ID NO 28
<211> LENGTH: 20
```

```
<212> TYPE: DNA
<213> ORGANISM: Artificial sequence
<220> FEATURE:
<223> OTHER INFORMATION: Primer AAR24308.1_4_spec_R_352

<400> SEQUENCE: 28
catgtgaaaa acctgcctgc                                               20

<210> SEQ ID NO 29
<211> LENGTH: 20
<212> TYPE: DNA
<213> ORGANISM: Artificial sequence
<220> FEATURE:
<223> OTHER INFORMATION: Primer AAR24308.1_9_spec_F_918

<400> SEQUENCE: 29
cacagatttg ccattggtgc                                               20

<210> SEQ ID NO 30
<211> LENGTH: 20
<212> TYPE: DNA
<213> ORGANISM: Artificial sequence
<220> FEATURE:
<223> OTHER INFORMATION: Primer AAR24308.1_9_spec_R_1042

<400> SEQUENCE: 30
aggaaggaac atcatccgga                                               20

<210> SEQ ID NO 31
<211> LENGTH: 20
<212> TYPE: DNA
<213> ORGANISM: Artificial sequence
<220> FEATURE:
<223> OTHER INFORMATION: Primer AAT64888.1_1_spec_F_983

<400> SEQUENCE: 31
taatggaggc cgagttcaga                                               20

<210> SEQ ID NO 32
<211> LENGTH: 20
<212> TYPE: DNA
<213> ORGANISM: Artificial sequence
<220> FEATURE:
<223> OTHER INFORMATION: Primer AAT64888.1_1_spec_R_1106

<400> SEQUENCE: 32
acgaccttgt tcggaaagac                                               20

<210> SEQ ID NO 33
<211> LENGTH: 20
<212> TYPE: DNA
<213> ORGANISM: Artificial sequence
<220> FEATURE:
<223> OTHER INFORMATION: Primer AAT64888.1_18_spec_F_922

<400> SEQUENCE: 33
aacgttctct agggtggtca                                               20

<210> SEQ ID NO 34
<211> LENGTH: 20
<212> TYPE: DNA
<213> ORGANISM: Artificial sequence
<220> FEATURE:
<223> OTHER INFORMATION: Primer AAT64888.1_18_spec_R_1002

<400> SEQUENCE: 34
```
tctgaactcg gcctccatta                                                     20

<210> SEQ ID NO 35
<211> LENGTH: 19
<212> TYPE: DNA
<213> ORGANISM: Artificial sequence
<220> FEATURE:
<223> OTHER INFORMATION: Primer AAW39060.1_1596_spec_F_1129

<400> SEQUENCE: 35
gagttgaagc ttggggtcc                                                      19

<210> SEQ ID NO 36
<211> LENGTH: 20
<212> TYPE: DNA
<213> ORGANISM: Artificial sequence
<220> FEATURE:
<223> OTHER INFORMATION: Primer AAW39060.1_1596_spec_R_1293

<400> SEQUENCE: 36
cggcatctat aggcttggtg                                                     20

<210> SEQ ID NO 37
<211> LENGTH: 20
<212> TYPE: DNA
<213> ORGANISM: Artificial sequence
<220> FEATURE:
<223> OTHER INFORMATION: Primer AAW39060.1_1629_spec_F_1025

<400> SEQUENCE: 37
acctatggac ccatgctctt                                                     20

<210> SEQ ID NO 38
<211> LENGTH: 19
<212> TYPE: DNA
<213> ORGANISM: Artificial sequence
<220> FEATURE:
<223> OTHER INFORMATION: Primer AAW39060.1_1629_spec_R_1146

<400> SEQUENCE: 38
gaccccaagc ttcaactcc                                                      19

<210> SEQ ID NO 39
<211> LENGTH: 19
<212> TYPE: DNA
<213> ORGANISM: Artificial sequence
<220> FEATURE:
<223> OTHER INFORMATION: Primer AAW39060.1_2131_spec_F_1129

<400> SEQUENCE: 39
gagttgaagc ttggggtcc                                                      19

<210> SEQ ID NO 40
<211> LENGTH: 20
<212> TYPE: DNA
<213> ORGANISM: Artificial sequence
<220> FEATURE:
<223> OTHER INFORMATION: Primer AAW39060.1_2131_spec_R_1289

<400> SEQUENCE: 40
atctataggc ttggtggggg                                                     20

<210> SEQ ID NO 41
<211> LENGTH: 20
<212> TYPE: DNA
<213> ORGANISM: Artificial sequence

```
<220> FEATURE:
<223> OTHER INFORMATION: Primer AAW39215.1_0_spec_F_793

<400> SEQUENCE: 41
tagcacagtg gcgtttacag                                                 20

<210> SEQ ID NO 42
<211> LENGTH: 20
<212> TYPE: DNA
<213> ORGANISM: Artificial sequence
<220> FEATURE:
<223> OTHER INFORMATION: Primer AAW39215.1_0_spec_R_898

<400> SEQUENCE: 42
ccagacataa caccccaacc                                                 20

<210> SEQ ID NO 43
<211> LENGTH: 20
<212> TYPE: DNA
<213> ORGANISM: Artificial sequence
<220> FEATURE:
<223> OTHER INFORMATION: Primer AAW39215.1_10_spec_F_879

<400> SEQUENCE: 43
ggttggggtg ttatgtctgg                                                 20

<210> SEQ ID NO 44
<211> LENGTH: 20
<212> TYPE: DNA
<213> ORGANISM: Artificial sequence
<220> FEATURE:
<223> OTHER INFORMATION: Primer AAW39215.1_10_spec_R_1034

<400> SEQUENCE: 44
acaaaacttt ctggcaccga                                                 20

<210> SEQ ID NO 45
<211> LENGTH: 20
<212> TYPE: DNA
<213> ORGANISM: Artificial sequence
<220> FEATURE:
<223> OTHER INFORMATION: Primer AAW39215.1_15_spec_F_801

<400> SEQUENCE: 45
tggcgtttac aggcatttct                                                 20

<210> SEQ ID NO 46
<211> LENGTH: 20
<212> TYPE: DNA
<213> ORGANISM: Artificial sequence
<220> FEATURE:
<223> OTHER INFORMATION: Primer AAW39215.1_15_spec_R_898

<400> SEQUENCE: 46
ccagacataa caccccaacc                                                 20

<210> SEQ ID NO 47
<211> LENGTH: 20
<212> TYPE: DNA
<213> ORGANISM: Artificial sequence
<220> FEATURE:
<223> OTHER INFORMATION: Primer AAW39215.1_7_spec_F_1052

<400> SEQUENCE: 47
tgctgatctt tgcccttctg                                                 20
```

```
<210> SEQ ID NO 48
<211> LENGTH: 20
<212> TYPE: DNA
<213> ORGANISM: Artificial sequence
<220> FEATURE:
<223> OTHER INFORMATION: Primer AAW39215.1_7_spec_R_1229

<400> SEQUENCE: 48
aacgccgcaa taggtatctg                                               20

<210> SEQ ID NO 49
<211> LENGTH: 20
<212> TYPE: DNA
<213> ORGANISM: Artificial sequence
<220> FEATURE:
<223> OTHER INFORMATION: Primer AAW39229.1_204_spec_F_1257

<400> SEQUENCE: 49
tgtaccggcg tttgtgtatt                                               20

<210> SEQ ID NO 50
<211> LENGTH: 20
<212> TYPE: DNA
<213> ORGANISM: Artificial sequence
<220> FEATURE:
<223> OTHER INFORMATION: Primer AAW39229.1_204_spec_R_1419

<400> SEQUENCE: 50
ggtcaagatc ccaccattcg                                               20

<210> SEQ ID NO 51
<211> LENGTH: 20
<212> TYPE: DNA
<213> ORGANISM: Artificial sequence
<220> FEATURE:
<223> OTHER INFORMATION: Primer AAW39240.1_1121_spec_F_889

<400> SEQUENCE: 51
aaagattccc ctttgtcggg                                               20

<210> SEQ ID NO 52
<211> LENGTH: 20
<212> TYPE: DNA
<213> ORGANISM: Artificial sequence
<220> FEATURE:
<223> OTHER INFORMATION: Primer AAW39240.1_1121_spec_R_1081

<400> SEQUENCE: 52
attacccaca tagcccggtt                                               20

<210> SEQ ID NO 53
<211> LENGTH: 21
<212> TYPE: DNA
<213> ORGANISM: Artificial sequence
<220> FEATURE:
<223> OTHER INFORMATION: Primer AAW39240.1_1506_spec_F_666

<400> SEQUENCE: 53
ggtgctcagg aaatggattc a                                             21

<210> SEQ ID NO 54
<211> LENGTH: 20
<212> TYPE: DNA
<213> ORGANISM: Artificial sequence
<220> FEATURE:
<223> OTHER INFORMATION: Primer AAW39240.1_1506_spec_R_819
```

<400> SEQUENCE: 54
gggcagtcca ctggagtata                                                     20

<210> SEQ ID NO 55
<211> LENGTH: 20
<212> TYPE: DNA
<213> ORGANISM: Artificial sequence
<220> FEATURE:
<223> OTHER INFORMATION: Primer AAW39240.1_2398_spec_F_946

<400> SEQUENCE: 55
ctgcggtttc cacccatatg                                                     20

<210> SEQ ID NO 56
<211> LENGTH: 20
<212> TYPE: DNA
<213> ORGANISM: Artificial sequence
<220> FEATURE:
<223> OTHER INFORMATION: Primer AAW39240.1_2398_spec_R_1081

<400> SEQUENCE: 56
attacccaca tagcccggtt                                                     20

<210> SEQ ID NO 57
<211> LENGTH: 19
<212> TYPE: DNA
<213> ORGANISM: Artificial sequence
<220> FEATURE:
<223> OTHER INFORMATION: Primer AAW39240.1_4451_spec_F_801

<400> SEQUENCE: 57
atactccagt ggactgccc                                                      19

<210> SEQ ID NO 58
<211> LENGTH: 20
<212> TYPE: DNA
<213> ORGANISM: Artificial sequence
<220> FEATURE:
<223> OTHER INFORMATION: Primer AAW39240.1_4451_spec_R_961

<400> SEQUENCE: 58
tgggtggaaa ccgcagtata                                                     20

<210> SEQ ID NO 59
<211> LENGTH: 22
<212> TYPE: DNA
<213> ORGANISM: Artificial sequence
<220> FEATURE:
<223> OTHER INFORMATION: Primer AAW39256.1_76_spec_F_1109

<400> SEQUENCE: 59
cggttcacat cttagaggac ag                                                  22

<210> SEQ ID NO 60
<211> LENGTH: 20
<212> TYPE: DNA
<213> ORGANISM: Artificial sequence
<220> FEATURE:
<223> OTHER INFORMATION: Primer AAW39256.1_76_spec_R_1192

<400> SEQUENCE: 60
cgttccatac cggcatctat                                                     20

<210> SEQ ID NO 61

<210> SEQ ID NO 61
<211> LENGTH: 22
<212> TYPE: DNA
<213> ORGANISM: Artificial sequence
<220> FEATURE:
<223> OTHER INFORMATION: Primer AAW39256.1_95_spec_F_1109

<400> SEQUENCE: 61
cggttcacat cttagaggac ag                                    22

<210> SEQ ID NO 62
<211> LENGTH: 19
<212> TYPE: DNA
<213> ORGANISM: Artificial sequence
<220> FEATURE:
<223> OTHER INFORMATION: Primer AAW39256.1_95_spec_R_1183

<400> SEQUENCE: 62
ccggcatcta tgggtttgg                                        19

<210> SEQ ID NO 63
<211> LENGTH: 22
<212> TYPE: DNA
<213> ORGANISM: Artificial sequence
<220> FEATURE:
<223> OTHER INFORMATION: Primer AAW39256.1_96_spec_F_1109

<400> SEQUENCE: 63
cggttcacat cttagaggac ag                                    22

<210> SEQ ID NO 64
<211> LENGTH: 19
<212> TYPE: DNA
<213> ORGANISM: Artificial sequence
<220> FEATURE:
<223> OTHER INFORMATION: Primer AAW39256.1_96_spec_R_1198

<400> SEQUENCE: 64
cagaagcgtt ccataccgg                                        19

<210> SEQ ID NO 65
<211> LENGTH: 20
<212> TYPE: DNA
<213> ORGANISM: Artificial sequence
<220> FEATURE:
<223> OTHER INFORMATION: Primer AAW39262.1_2442_spec_F_1050

<400> SEQUENCE: 65
atgtcttccc ctgccattca                                       20

<210> SEQ ID NO 66
<211> LENGTH: 20
<212> TYPE: DNA
<213> ORGANISM: Artificial sequence
<220> FEATURE:
<223> OTHER INFORMATION: Primer AAW39262.1_2442_spec_R_1200

<400> SEQUENCE: 66
aggcatcagc acaaataccg                                       20

<210> SEQ ID NO 67
<211> LENGTH: 20
<212> TYPE: DNA
<213> ORGANISM: Artificial sequence
<220> FEATURE:
<223> OTHER INFORMATION: Primer AAW39273.1_1218_spec_F_1259

<400> SEQUENCE: 67
caacctgttc agctgtgcat     20

<210> SEQ ID NO 68
<211> LENGTH: 20
<212> TYPE: DNA
<213> ORGANISM: Artificial sequence
<220> FEATURE:
<223> OTHER INFORMATION: Primer AAW39273.1_1218_spec_R_1416

<400> SEQUENCE: 68
caccctccat gctggtaaag     20

<210> SEQ ID NO 69
<211> LENGTH: 20
<212> TYPE: DNA
<213> ORGANISM: Artificial sequence
<220> FEATURE:
<223> OTHER INFORMATION: Primer AAW39273.1_2015_ext_F_1101

<400> SEQUENCE: 69
tgcggtatct gtgctgaaac     20

<210> SEQ ID NO 70
<211> LENGTH: 20
<212> TYPE: DNA
<213> ORGANISM: Artificial sequence
<220> FEATURE:
<223> OTHER INFORMATION: Primer AAW39273.1_2015_ext_R_1183

<400> SEQUENCE: 70
tggccgcaat tattatccca     20

<210> SEQ ID NO 71
<211> LENGTH: 20
<212> TYPE: DNA
<213> ORGANISM: Artificial sequence
<220> FEATURE:
<223> OTHER INFORMATION: Primer AAW39843.1_0_spec_F_1212

<400> SEQUENCE: 71
gaatttggct cagtttgcgg     20

<210> SEQ ID NO 72
<211> LENGTH: 20
<212> TYPE: DNA
<213> ORGANISM: Artificial sequence
<220> FEATURE:
<223> OTHER INFORMATION: Primer AAW39843.1_0_spec_R_1324

<400> SEQUENCE: 72
gcgcatttac ggcaagtatg     20

<210> SEQ ID NO 73
<211> LENGTH: 20
<212> TYPE: DNA
<213> ORGANISM: Artificial sequence
<220> FEATURE:
<223> OTHER INFORMATION: Primer AAW39843.1_13_spec_F_1169

<400> SEQUENCE: 73
tatagcagag atgggacgca     20

<210> SEQ ID NO 74
<211> LENGTH: 20
<212> TYPE: DNA

-continued

<213> ORGANISM: Artificial sequence
<220> FEATURE:
<223> OTHER INFORMATION: Primer AAW39843.1_13_spec_R_1300

<400> SEQUENCE: 74
aaacggaata tcccagcgtc                                               20

<210> SEQ ID NO 75
<211> LENGTH: 20
<212> TYPE: DNA
<213> ORGANISM: Artificial sequence
<220> FEATURE:
<223> OTHER INFORMATION: Primer AAW39843.1_19_spec_F_1249

<400> SEQUENCE: 75
ctgacttgcc tctaatgcca                                               20

<210> SEQ ID NO 76
<211> LENGTH: 20
<212> TYPE: DNA
<213> ORGANISM: Artificial sequence
<220> FEATURE:
<223> OTHER INFORMATION: Primer AAW39843.1_19_spec_R_1324

<400> SEQUENCE: 76
gcgcatttac ggcaagtatg                                               20

<210> SEQ ID NO 77
<211> LENGTH: 19
<212> TYPE: DNA
<213> ORGANISM: Artificial sequence
<220> FEATURE:
<223> OTHER INFORMATION: Primer AAW40581.1_4941_spec_F_202

<400> SEQUENCE: 77
gcactaccgc cgctttaaa                                                19

<210> SEQ ID NO 78
<211> LENGTH: 20
<212> TYPE: DNA
<213> ORGANISM: Artificial sequence
<220> FEATURE:
<223> OTHER INFORMATION: Primer AAW40581.1_4941_spec_R_276

<400> SEQUENCE: 78
ggagtatccg cccgttattc                                               20

<210> SEQ ID NO 79
<211> LENGTH: 20
<212> TYPE: DNA
<213> ORGANISM: Artificial sequence
<220> FEATURE:
<223> OTHER INFORMATION: Primer AAW40581.1_91_spec_F_957

<400> SEQUENCE: 79
ctgaacgagg taaccgaacc                                               20

<210> SEQ ID NO 80
<211> LENGTH: 20
<212> TYPE: DNA
<213> ORGANISM: Artificial sequence
<220> FEATURE:
<223> OTHER INFORMATION: Primer AAW40581.1_91_spec_R_1046

<400> SEQUENCE: 80
tacttcgtag ggagtgccat                                               20

<210> SEQ ID NO 81
<211> LENGTH: 20
<212> TYPE: DNA
<213> ORGANISM: Artificial sequence
<220> FEATURE:
<223> OTHER INFORMATION: Primer AAW40581.1_96_spec_F_1027

<400> SEQUENCE: 81
atggcactcc ctacgaagta                                               20

<210> SEQ ID NO 82
<211> LENGTH: 20
<212> TYPE: DNA
<213> ORGANISM: Artificial sequence
<220> FEATURE:
<223> OTHER INFORMATION: Primer AAW40581.1_96_spec_R_1216

<400> SEQUENCE: 82
accatttcgt cagccacaat                                               20

<210> SEQ ID NO 83
<211> LENGTH: 20
<212> TYPE: DNA
<213> ORGANISM: Artificial sequence
<220> FEATURE:
<223> OTHER INFORMATION: Primer AAW40581.1_98_spec_F_886

<400> SEQUENCE: 83
cctttgaccc cagcaagatt                                               20

<210> SEQ ID NO 84
<211> LENGTH: 20
<212> TYPE: DNA
<213> ORGANISM: Artificial sequence
<220> FEATURE:
<223> OTHER INFORMATION: Primer AAW40581.1_98_spec_R_1046

<400> SEQUENCE: 84
tacttcgtag ggagtgccat                                               20

<210> SEQ ID NO 85
<211> LENGTH: 20
<212> TYPE: DNA
<213> ORGANISM: Artificial sequence
<220> FEATURE:
<223> OTHER INFORMATION: Primer AAW40589.1_12_spec_F_1218

<400> SEQUENCE: 85
ggcagtgttc acggctattt                                               20

<210> SEQ ID NO 86
<211> LENGTH: 20
<212> TYPE: DNA
<213> ORGANISM: Artificial sequence
<220> FEATURE:
<223> OTHER INFORMATION: Primer AAW40589.1_12_spec_R_1344

<400> SEQUENCE: 86
atttggcagg gcattcatca                                               20

<210> SEQ ID NO 87
<211> LENGTH: 20
<212> TYPE: DNA
<213> ORGANISM: Artificial sequence
<220> FEATURE:

-continued

<223> OTHER INFORMATION: Primer AAW40589.1_5_spec_F_1186

<400> SEQUENCE: 87
gcaactcaaa cgtctgcatc                                           20

<210> SEQ ID NO 88
<211> LENGTH: 20
<212> TYPE: DNA
<213> ORGANISM: Artificial sequence
<220> FEATURE:
<223> OTHER INFORMATION: Primer AAW40589.1_5_spec_R_1312

<400> SEQUENCE: 88
caggtatggc agaaacggaa                                           20

<210> SEQ ID NO 89
<211> LENGTH: 21
<212> TYPE: DNA
<213> ORGANISM: Artificial sequence
<220> FEATURE:
<223> OTHER INFORMATION: Primer ABQ16695.1_3523_spec_F_1205

<400> SEQUENCE: 89
tgctaattcc aatcccacca a                                         21

<210> SEQ ID NO 90
<211> LENGTH: 20
<212> TYPE: DNA
<213> ORGANISM: Artificial sequence
<220> FEATURE:
<223> OTHER INFORMATION: Primer ABQ16695.1_3523_spec_R_1302

<400> SEQUENCE: 90
cccagaaatt gtgacaggca                                           20

<210> SEQ ID NO 91
<211> LENGTH: 20
<212> TYPE: DNA
<213> ORGANISM: Artificial sequence
<220> FEATURE:
<223> OTHER INFORMATION: Primer ABQ16695.1_627_spec_F_1209

<400> SEQUENCE: 91
aattccaatc ccaccaagct                                           20

<210> SEQ ID NO 92
<211> LENGTH: 20
<212> TYPE: DNA
<213> ORGANISM: Artificial sequence
<220> FEATURE:
<223> OTHER INFORMATION: Primer ABQ16695.1_627_spec_R_1302

<400> SEQUENCE: 92
cccagaaatt gtgacaggca                                           20

<210> SEQ ID NO 93
<211> LENGTH: 20
<212> TYPE: DNA
<213> ORGANISM: Artificial sequence
<220> FEATURE:
<223> OTHER INFORMATION: Primer ABQ16703.1_2_spec_F_1242

<400> SEQUENCE: 93
tcacggtgga gtggagtatt                                           20

```
<210> SEQ ID NO 94
<211> LENGTH: 20
<212> TYPE: DNA
<213> ORGANISM: Artificial sequence
<220> FEATURE:
<223> OTHER INFORMATION: Primer ABQ16703.1_2_spec_R_1331

<400> SEQUENCE: 94
ggtgggagct aaaggcaaat                                                 20

<210> SEQ ID NO 95
<211> LENGTH: 20
<212> TYPE: DNA
<213> ORGANISM: Artificial sequence
<220> FEATURE:
<223> OTHER INFORMATION: Primer ABQ16703.1_54_spec_F_1312

<400> SEQUENCE: 95
atttgccttt agctcccacc                                                 20

<210> SEQ ID NO 96
<211> LENGTH: 20
<212> TYPE: DNA
<213> ORGANISM: Artificial sequence
<220> FEATURE:
<223> OTHER INFORMATION: Primer ABQ16703.1_54_spec_R_1393

<400> SEQUENCE: 96
caagcatcgg cacaaatacc                                                 20

<210> SEQ ID NO 97
<211> LENGTH: 20
<212> TYPE: DNA
<213> ORGANISM: Artificial sequence
<220> FEATURE:
<223> OTHER INFORMATION: Primer ABY28312.1_3639_spec_F_842

<400> SEQUENCE: 97
cgctcacttg gctataccctg                                                20

<210> SEQ ID NO 98
<211> LENGTH: 21
<212> TYPE: DNA
<213> ORGANISM: Artificial sequence
<220> FEATURE:
<223> OTHER INFORMATION: Primer ABY28312.1_3639_spec_R_942

<400> SEQUENCE: 98
cggtttcctt ccgtaatacc g                                               21

<210> SEQ ID NO 99
<211> LENGTH: 20
<212> TYPE: DNA
<213> ORGANISM: Artificial sequence
<220> FEATURE:
<223> OTHER INFORMATION: Primer ACF24861.1_1091_spec_F_1344

<400> SEQUENCE: 99
tggcaggcgg ataaattctt                                                 20

<210> SEQ ID NO 100
<211> LENGTH: 20
<212> TYPE: DNA
<213> ORGANISM: Artificial sequence
<220> FEATURE:
<223> OTHER INFORMATION: Primer ACF24861.1_1091_spec_R_1437
```

```
<400> SEQUENCE: 100
cggcactgtc aaacccataa                                          20

<210> SEQ ID NO 101
<211> LENGTH: 20
<212> TYPE: DNA
<213> ORGANISM: Artificial sequence
<220> FEATURE:
<223> OTHER INFORMATION: Primer ACF24861.1_1415_ext_F_1342

<400> SEQUENCE: 101
tgtggcaggc ggataaattc                                          20

<210> SEQ ID NO 102
<211> LENGTH: 20
<212> TYPE: DNA
<213> ORGANISM: Artificial sequence
<220> FEATURE:
<223> OTHER INFORMATION: Primer ACF24861.1_1415_ext_R_1430

<400> SEQUENCE: 102
gtcaaaccca taaaccggca                                          20

<210> SEQ ID NO 103
<211> LENGTH: 21
<212> TYPE: DNA
<213> ORGANISM: Artificial sequence
<220> FEATURE:
<223> OTHER INFORMATION: Primer ACH87594.1_2227_ext_F_161

<400> SEQUENCE: 103
caaggtggat gcaaagtacc a                                        21

<210> SEQ ID NO 104
<211> LENGTH: 20
<212> TYPE: DNA
<213> ORGANISM: Artificial sequence
<220> FEATURE:
<223> OTHER INFORMATION: Primer ACH87594.1_2227_ext_R_340

<400> SEQUENCE: 104
ttgatcccaa gtctttccgc                                          20

<210> SEQ ID NO 105
<211> LENGTH: 21
<212> TYPE: DNA
<213> ORGANISM: Artificial sequence
<220> FEATURE:
<223> OTHER INFORMATION: Primer ACH87594.1_2865_ext_F_161

<400> SEQUENCE: 105
caaggtggat gcaaagtacc a                                        21

<210> SEQ ID NO 106
<211> LENGTH: 20
<212> TYPE: DNA
<213> ORGANISM: Artificial sequence
<220> FEATURE:
<223> OTHER INFORMATION: Primer ACH87594.1_2865_ext_R_299

<400> SEQUENCE: 106
ccccgtatct ttcttgcctg                                          20

<210> SEQ ID NO 107
<211> LENGTH: 20
```

```
<212> TYPE: DNA
<213> ORGANISM: Artificial sequence
<220> FEATURE:
<223> OTHER INFORMATION: Primer ACH87594.1_437_pr_F_407

<400> SEQUENCE: 107
aacccagcgc cataatgaaa                                           20

<210> SEQ ID NO 108
<211> LENGTH: 20
<212> TYPE: DNA
<213> ORGANISM: Artificial sequence
<220> FEATURE:
<223> OTHER INFORMATION: Primer ACH87594.1_437_pr_R_516

<400> SEQUENCE: 108
gaccaccact tacgcagtta                                           20

<210> SEQ ID NO 109
<211> LENGTH: 21
<212> TYPE: DNA
<213> ORGANISM: Artificial sequence
<220> FEATURE:
<223> OTHER INFORMATION: Primer ACH87594.1_4754_ext_F_138

<400> SEQUENCE: 109
acggaaacct cagaatttcc a                                         21

<210> SEQ ID NO 110
<211> LENGTH: 20
<212> TYPE: DNA
<213> ORGANISM: Artificial sequence
<220> FEATURE:
<223> OTHER INFORMATION: Primer ACH87594.1_4754_ext_R_299

<400> SEQUENCE: 110
ccccgtatct ttcttgcctg                                           20

<210> SEQ ID NO 111
<211> LENGTH: 20
<212> TYPE: DNA
<213> ORGANISM: Artificial sequence
<220> FEATURE:
<223> OTHER INFORMATION: Primer ACH87594.1_522_pr_F_353

<400> SEQUENCE: 111
gacaaatgca gaaacaggcg                                           20

<210> SEQ ID NO 112
<211> LENGTH: 20
<212> TYPE: DNA
<213> ORGANISM: Artificial sequence
<220> FEATURE:
<223> OTHER INFORMATION: Primer ACH87594.1_522_pr_R_516

<400> SEQUENCE: 112
gaccaccact tacgcagtta                                           20

<210> SEQ ID NO 113
<211> LENGTH: 20
<212> TYPE: DNA
<213> ORGANISM: Artificial sequence
<220> FEATURE:
<223> OTHER INFORMATION: Primer ACH87594.1_646_pr_F_401

<400> SEQUENCE: 113
```
catgttaacc cagcgccata                                           20

<210> SEQ ID NO 114
<211> LENGTH: 20
<212> TYPE: DNA
<213> ORGANISM: Artificial sequence
<220> FEATURE:
<223> OTHER INFORMATION: Primer ACH87594.1_646_pr_R_516

<400> SEQUENCE: 114
gaccaccact tacgcagtta                                           20

<210> SEQ ID NO 115
<211> LENGTH: 20
<212> TYPE: DNA
<213> ORGANISM: Artificial sequence
<220> FEATURE:
<223> OTHER INFORMATION: Primer ACH87598.1_3654_ext_F_690

<400> SEQUENCE: 115
ttttctgagg aagcttggct                                           20

<210> SEQ ID NO 116
<211> LENGTH: 19
<212> TYPE: DNA
<213> ORGANISM: Artificial sequence
<220> FEATURE:
<223> OTHER INFORMATION: Primer ACH87598.1_3654_ext_R_873

<400> SEQUENCE: 116
cttgtccgga gcaagttcc                                            19

<210> SEQ ID NO 117
<211> LENGTH: 20
<212> TYPE: DNA
<213> ORGANISM: Artificial sequence
<220> FEATURE:
<223> OTHER INFORMATION: Primer ACL18777.1_2120_ext_F_1011

<400> SEQUENCE: 117
gatttctgcc gggtatgcaa                                           20

<210> SEQ ID NO 118
<211> LENGTH: 20
<212> TYPE: DNA
<213> ORGANISM: Artificial sequence
<220> FEATURE:
<223> OTHER INFORMATION: Primer ACL18777.1_2120_ext_R_1117

<400> SEQUENCE: 118
tcactgttcc agcgcagata                                           20

<210> SEQ ID NO 119
<211> LENGTH: 20
<212> TYPE: DNA
<213> ORGANISM: Artificial sequence
<220> FEATURE:
<223> OTHER INFORMATION: Primer ACL18777.1_2126_ext_F_1016

<400> SEQUENCE: 119
ctgccgggta tgcaagaaat                                           20

<210> SEQ ID NO 120
<211> LENGTH: 20
<212> TYPE: DNA
<213> ORGANISM: Artificial sequence

```
<220> FEATURE:
<223> OTHER INFORMATION: Primer ACL18777.1_2126_ext_R_1117

<400> SEQUENCE: 120
tcactgttcc agcgcagata                                           20

<210> SEQ ID NO 121
<211> LENGTH: 20
<212> TYPE: DNA
<213> ORGANISM: Artificial sequence
<220> FEATURE:
<223> OTHER INFORMATION: Primer ACL18777.1_38_spec_F_248

<400> SEQUENCE: 121
taatgatcag tggctgggga                                           20

<210> SEQ ID NO 122
<211> LENGTH: 20
<212> TYPE: DNA
<213> ORGANISM: Artificial sequence
<220> FEATURE:
<223> OTHER INFORMATION: Primer ACL18777.1_38_spec_R_421

<400> SEQUENCE: 122
aaaataccca gcgctccatc                                           20

<210> SEQ ID NO 123
<211> LENGTH: 20
<212> TYPE: DNA
<213> ORGANISM: Artificial sequence
<220> FEATURE:
<223> OTHER INFORMATION: Primer ACL18777.1_77_spec_F_355

<400> SEQUENCE: 123
cacaggttgc catgtaccat                                           20

<210> SEQ ID NO 124
<211> LENGTH: 20
<212> TYPE: DNA
<213> ORGANISM: Artificial sequence
<220> FEATURE:
<223> OTHER INFORMATION: Primer ACL18777.1_77_spec_R_485

<400> SEQUENCE: 124
tatgggcagt ttctcctggt                                           20

<210> SEQ ID NO 125
<211> LENGTH: 20
<212> TYPE: DNA
<213> ORGANISM: Artificial sequence
<220> FEATURE:
<223> OTHER INFORMATION: Primer ACZ61261.1_113_spec_F_456

<400> SEQUENCE: 125
tctgctttac cggttgaacc                                           20

<210> SEQ ID NO 126
<211> LENGTH: 20
<212> TYPE: DNA
<213> ORGANISM: Artificial sequence
<220> FEATURE:
<223> OTHER INFORMATION: Primer ACZ61261.1_113_spec_R_568

<400> SEQUENCE: 126
acctgaggcg taccgaaata                                           20
```

<210> SEQ ID NO 127
<211> LENGTH: 20
<212> TYPE: DNA
<213> ORGANISM: Artificial sequence
<220> FEATURE:
<223> OTHER INFORMATION: Primer ACZ61261.1_36_spec_F_398

<400> SEQUENCE: 127
cacctcttcg tcatggatgg                                        20

<210> SEQ ID NO 128
<211> LENGTH: 20
<212> TYPE: DNA
<213> ORGANISM: Artificial sequence
<220> FEATURE:
<223> OTHER INFORMATION: Primer ACZ61261.1_36_spec_R_475

<400> SEQUENCE: 128
ggttcaaccg gtaaagcaga                                        20

<210> SEQ ID NO 129
<211> LENGTH: 20
<212> TYPE: DNA
<213> ORGANISM: Artificial sequence
<220> FEATURE:
<223> OTHER INFORMATION: Primer ACZ61261.1_94_spec_F_409

<400> SEQUENCE: 129
catggatggg gcttgatgtt                                        20

<210> SEQ ID NO 130
<211> LENGTH: 20
<212> TYPE: DNA
<213> ORGANISM: Artificial sequence
<220> FEATURE:
<223> OTHER INFORMATION: Primer ACZ61261.1_94_spec_R_568

<400> SEQUENCE: 130
acctgaggcg taccgaaata                                        20

<210> SEQ ID NO 131
<211> LENGTH: 20
<212> TYPE: DNA
<213> ORGANISM: Artificial sequence
<220> FEATURE:
<223> OTHER INFORMATION: Primer ACZ61261.1_98_spec_F_692

<400> SEQUENCE: 131
tccggttggt tttcaggatg                                        20

<210> SEQ ID NO 132
<211> LENGTH: 20
<212> TYPE: DNA
<213> ORGANISM: Artificial sequence
<220> FEATURE:
<223> OTHER INFORMATION: Primer ACZ61261.1_98_spec_R_785

<400> SEQUENCE: 132
cagtgcattt tctttggcgg                                        20

<210> SEQ ID NO 133
<211> LENGTH: 20
<212> TYPE: DNA
<213> ORGANISM: Artificial sequence
<220> FEATURE:
<223> OTHER INFORMATION: Primer ACZ61272.1_0_spec_F_1075

-continued

<400> SEQUENCE: 133
ccggtttgtg tgaatcagga                                               20

<210> SEQ ID NO 134
<211> LENGTH: 20
<212> TYPE: DNA
<213> ORGANISM: Artificial sequence
<220> FEATURE:
<223> OTHER INFORMATION: Primer ACZ61272.1_0_spec_R_1175

<400> SEQUENCE: 134
ggctagagga aggtcagtga                                               20

<210> SEQ ID NO 135
<211> LENGTH: 20
<212> TYPE: DNA
<213> ORGANISM: Artificial sequence
<220> FEATURE:
<223> OTHER INFORMATION: Primer ACZ61272.1_4_spec_F_1085

<400> SEQUENCE: 135
tgaatcagga cgtaccacct                                               20

<210> SEQ ID NO 136
<211> LENGTH: 20
<212> TYPE: DNA
<213> ORGANISM: Artificial sequence
<220> FEATURE:
<223> OTHER INFORMATION: Primer ACZ61272.1_4_spec_R_1175

<400> SEQUENCE: 136
ggctagagga aggtcagtga                                               20

<210> SEQ ID NO 137
<211> LENGTH: 20
<212> TYPE: DNA
<213> ORGANISM: Artificial sequence
<220> FEATURE:
<223> OTHER INFORMATION: Primer ACZ61272.1_8_spec_F_1156

<400> SEQUENCE: 137
tcactgacct tcctctagcc                                               20

<210> SEQ ID NO 138
<211> LENGTH: 20
<212> TYPE: DNA
<213> ORGANISM: Artificial sequence
<220> FEATURE:
<223> OTHER INFORMATION: Primer ACZ61272.1_8_spec_R_1261

<400> SEQUENCE: 138
ctgattgtgt tggaagggca                                               20

<210> SEQ ID NO 139
<211> LENGTH: 20
<212> TYPE: DNA
<213> ORGANISM: Artificial sequence
<220> FEATURE:
<223> OTHER INFORMATION: Primer ACZ61277.1_0_spec_F_741

<400> SEQUENCE: 139
gaaaagctgg tgattccgga                                               20

<210> SEQ ID NO 140

```
<211> LENGTH: 20
<212> TYPE: DNA
<213> ORGANISM: Artificial sequence
<220> FEATURE:
<223> OTHER INFORMATION: Primer ACZ61277.1_0_spec_R_886

<400> SEQUENCE: 140
gtttgccaaa cagatgccag                                               20

<210> SEQ ID NO 141
<211> LENGTH: 20
<212> TYPE: DNA
<213> ORGANISM: Artificial sequence
<220> FEATURE:
<223> OTHER INFORMATION: Primer ACZ61277.1_1673_ext_F_1317

<400> SEQUENCE: 141
ggtatctgca tgggttcctg                                               20

<210> SEQ ID NO 142
<211> LENGTH: 20
<212> TYPE: DNA
<213> ORGANISM: Artificial sequence
<220> FEATURE:
<223> OTHER INFORMATION: Primer ACZ61277.1_1673_ext_R_1445

<400> SEQUENCE: 142
accaaagaac ttgtcagcct                                               20

<210> SEQ ID NO 143
<211> LENGTH: 20
<212> TYPE: DNA
<213> ORGANISM: Artificial sequence
<220> FEATURE:
<223> OTHER INFORMATION: Primer ACZ61277.1_2882_ext_F_1317

<400> SEQUENCE: 143
ggtatctgca tgggttcctg                                               20

<210> SEQ ID NO 144
<211> LENGTH: 21
<212> TYPE: DNA
<213> ORGANISM: Artificial sequence
<220> FEATURE:
<223> OTHER INFORMATION: Primer ACZ61277.1_2882_ext_R_1446

<400> SEQUENCE: 144
aaccaaagaa cttgtcagcc t                                             21

<210> SEQ ID NO 145
<211> LENGTH: 20
<212> TYPE: DNA
<213> ORGANISM: Artificial sequence
<220> FEATURE:
<223> OTHER INFORMATION: Primer ACZ61277.1_3_spec_F_741

<400> SEQUENCE: 145
gaaaagctgg tgattccgga                                               20

<210> SEQ ID NO 146
<211> LENGTH: 20
<212> TYPE: DNA
<213> ORGANISM: Artificial sequence
<220> FEATURE:
<223> OTHER INFORMATION: Primer ACZ61277.1_3_spec_R_841

<400> SEQUENCE: 146
```
actctcaaat tgccgctacc                      20

<210> SEQ ID NO 147
<211> LENGTH: 20
<212> TYPE: DNA
<213> ORGANISM: Artificial sequence
<220> FEATURE:
<223> OTHER INFORMATION: Primer ACZ61277.1_7_spec_F_1244

<400> SEQUENCE: 147
tccgggcaaa aaggttttct                      20

<210> SEQ ID NO 148
<211> LENGTH: 20
<212> TYPE: DNA
<213> ORGANISM: Artificial sequence
<220> FEATURE:
<223> OTHER INFORMATION: Primer ACZ61277.1_7_spec_R_1357

<400> SEQUENCE: 148
gcattgtcca cgttgaacac                      20

<210> SEQ ID NO 149
<211> LENGTH: 20
<212> TYPE: DNA
<213> ORGANISM: Artificial sequence
<220> FEATURE:
<223> OTHER INFORMATION: Primer ACZ61293.1_101_spec_F_876

<400> SEQUENCE: 149
aaactccgca cctttgatcc                      20

<210> SEQ ID NO 150
<211> LENGTH: 20
<212> TYPE: DNA
<213> ORGANISM: Artificial sequence
<220> FEATURE:
<223> OTHER INFORMATION: Primer ACZ61293.1_101_spec_R_993

<400> SEQUENCE: 150
ccggcttggt aaattcaggt                      20

<210> SEQ ID NO 151
<211> LENGTH: 20
<212> TYPE: DNA
<213> ORGANISM: Artificial sequence
<220> FEATURE:
<223> OTHER INFORMATION: Primer ACZ61293.1_61_spec_F_931

<400> SEQUENCE: 151
tcagcggtga aaccaatgaa                      20

<210> SEQ ID NO 152
<211> LENGTH: 20
<212> TYPE: DNA
<213> ORGANISM: Artificial sequence
<220> FEATURE:
<223> OTHER INFORMATION: Primer ACZ61293.1_61_spec_R_1038

<400> SEQUENCE: 152 aggggggtatt ctcgtatcgg                      20

<210> SEQ ID NO 153
<211> LENGTH: 20
<212> TYPE: DNA

```
<213> ORGANISM: Artificial sequence
<220> FEATURE:
<223> OTHER INFORMATION: Primer ACZ61293.1_764_spec_F_955

<400> SEQUENCE: 153
ccctgaacga agtaaccgaa                                                     20

<210> SEQ ID NO 154
<211> LENGTH: 20
<212> TYPE: DNA
<213> ORGANISM: Artificial sequence
<220> FEATURE:
<223> OTHER INFORMATION: Primer ACZ61293.1_764_spec_R_1038

<400> SEQUENCE: 154 aggggggtatt ctcgtatcgg                                                    20

<210> SEQ ID NO 155
<211> LENGTH: 20
<212> TYPE: DNA
<213> ORGANISM: Artificial sequence
<220> FEATURE:
<223> OTHER INFORMATION: Primer ACZ61341.1_1883_spec_F_437

<400> SEQUENCE: 155
ggacaggtgg catattaccc                                                     20

<210> SEQ ID NO 156
<211> LENGTH: 20
<212> TYPE: DNA
<213> ORGANISM: Artificial sequence
<220> FEATURE:
<223> OTHER INFORMATION: Primer ACZ61341.1_1883_spec_R_517

<400> SEQUENCE: 156
tcgggagaaa gctcaacctt                                                     20

<210> SEQ ID NO 157
<211> LENGTH: 20
<212> TYPE: DNA
<213> ORGANISM: Artificial sequence
<220> FEATURE:
<223> OTHER INFORMATION: Primer ACZ61341.1_2104_spec_F_270

<400> SEQUENCE: 157
ttttcccaga tagtcaggcg                                                     20

<210> SEQ ID NO 158
<211> LENGTH: 20
<212> TYPE: DNA
<213> ORGANISM: Artificial sequence
<220> FEATURE:
<223> OTHER INFORMATION: Primer ACZ61341.1_2104_spec_R_456

<400> SEQUENCE: 158
gggtaatatg ccacctgtcc                                                     20

<210> SEQ ID NO 159
<211> LENGTH: 19
<212> TYPE: DNA
<213> ORGANISM: Artificial sequence
<220> FEATURE:
<223> OTHER INFORMATION: Primer ACZ61341.1_4924_spec_F_258

<400> SEQUENCE: 159
cgcgaacatg gttttcccc                                                      19
```

<210> SEQ ID NO 160
<211> LENGTH: 20
<212> TYPE: DNA
<213> ORGANISM: Artificial sequence
<220> FEATURE:
<223> OTHER INFORMATION: Primer ACZ61341.1_4924_spec_R_456

<400> SEQUENCE: 160
gggtaatatg ccacctgtcc        20

<210> SEQ ID NO 161
<211> LENGTH: 20
<212> TYPE: DNA
<213> ORGANISM: Artificial sequence
<220> FEATURE:
<223> OTHER INFORMATION: Primer ACZ61341.1_589_spec_F_259

<400> SEQUENCE: 161
gcgaacatgg tttttcccag        20

<210> SEQ ID NO 162
<211> LENGTH: 20
<212> TYPE: DNA
<213> ORGANISM: Artificial sequence
<220> FEATURE:
<223> OTHER INFORMATION: Primer ACZ61341.1_589_spec_R_456

<400> SEQUENCE: 162
gggtaatatg ccacctgtcc        20

<210> SEQ ID NO 163
<211> LENGTH: 20
<212> TYPE: DNA
<213> ORGANISM: Artificial sequence
<220> FEATURE:
<223> OTHER INFORMATION: Primer ACZ62362.1_1266_ext_F_957

<400> SEQUENCE: 163
tttatccgcg gtttgggtta        20

<210> SEQ ID NO 164
<211> LENGTH: 20
<212> TYPE: DNA
<213> ORGANISM: Artificial sequence
<220> FEATURE:
<223> OTHER INFORMATION: Primer ACZ62362.1_1266_ext_R_1097

<400> SEQUENCE: 164
gttggttgtg ccgtatttgg        20

<210> SEQ ID NO 165
<211> LENGTH: 20
<212> TYPE: DNA
<213> ORGANISM: Artificial sequence
<220> FEATURE:
<223> OTHER INFORMATION: Primer ACZ62362.1_137_spec_F_178

<400> SEQUENCE: 165
ttaacaagaa cccgtggtgg        20

<210> SEQ ID NO 166
<211> LENGTH: 20
<212> TYPE: DNA
<213> ORGANISM: Artificial sequence
<220> FEATURE:

<223> OTHER INFORMATION: Primer ACZ62362.1_137_spec_R_304

<400> SEQUENCE: 166
aagtcagcta cagtgggtct                                            20

<210> SEQ ID NO 167
<211> LENGTH: 20
<212> TYPE: DNA
<213> ORGANISM: Artificial sequence
<220> FEATURE:
<223> OTHER INFORMATION: Primer ACZ62362.1_3471_ext_F_957

<400> SEQUENCE: 167
tttatccgcg gtttgggtta                                            20

<210> SEQ ID NO 168
<211> LENGTH: 20
<212> TYPE: DNA
<213> ORGANISM: Artificial sequence
<220> FEATURE:
<223> OTHER INFORMATION: Primer ACZ62362.1_3471_ext_R_1063

<400> SEQUENCE: 168
gaagacatac gcccgtgttc                                            20

<210> SEQ ID NO 169
<211> LENGTH: 20
<212> TYPE: DNA
<213> ORGANISM: Artificial sequence
<220> FEATURE:
<223> OTHER INFORMATION: Primer ACZ62362.1_361_spec_F_48

<400> SEQUENCE: 169
tttcattcca cactctcgcg                                            20

<210> SEQ ID NO 170
<211> LENGTH: 20
<212> TYPE: DNA
<213> ORGANISM: Artificial sequence
<220> FEATURE:
<223> OTHER INFORMATION: Primer ACZ62362.1_361_spec_R_197

<400> SEQUENCE: 170
ccaccacggg ttcttgttaa                                            20

<210> SEQ ID NO 171
<211> LENGTH: 20
<212> TYPE: DNA
<213> ORGANISM: Artificial sequence
<220> FEATURE:
<223> OTHER INFORMATION: Primer ACZ62362.1_37_spec_F_105

<400> SEQUENCE: 171
ggtttaggga ctatgagcgc                                            20

<210> SEQ ID NO 172
<211> LENGTH: 20
<212> TYPE: DNA
<213> ORGANISM: Artificial sequence
<220> FEATURE:
<223> OTHER INFORMATION: Primer ACZ62362.1_37_spec_R_197

<400> SEQUENCE: 172
ccaccacggg ttcttgttaa                                            20

```
<210> SEQ ID NO 173
<211> LENGTH: 20
<212> TYPE: DNA
<213> ORGANISM: Artificial sequence
<220> FEATURE:
<223> OTHER INFORMATION: Primer ACZ62362.1_389_spec_F_94

<400> SEQUENCE: 173
tagtcggagc aggtttaggg                                               20

<210> SEQ ID NO 174
<211> LENGTH: 20
<212> TYPE: DNA
<213> ORGANISM: Artificial sequence
<220> FEATURE:
<223> OTHER INFORMATION: Primer ACZ62362.1_389_spec_R_197

<400> SEQUENCE: 174
ccaccacggg ttcttgttaa                                               20

<210> SEQ ID NO 175
<211> LENGTH: 20
<212> TYPE: DNA
<213> ORGANISM: Artificial sequence
<220> FEATURE:
<223> OTHER INFORMATION: Primer ACZ62362.1_67_spec_F_178

<400> SEQUENCE: 175
ttaacaagaa cccgtggtgg                                               20

<210> SEQ ID NO 176
<211> LENGTH: 20
<212> TYPE: DNA
<213> ORGANISM: Artificial sequence
<220> FEATURE:
<223> OTHER INFORMATION: Primer ACZ62362.1_67_spec_R_358

<400> SEQUENCE: 176
atttcggggg tttcaaggtc                                               20

<210> SEQ ID NO 177
<211> LENGTH: 20
<212> TYPE: DNA
<213> ORGANISM: Artificial sequence
<220> FEATURE:
<223> OTHER INFORMATION: Primer ACZ62391.1_11_ext_F_550

<400> SEQUENCE: 177
atgggagcgt accaaaatgg                                               20

<210> SEQ ID NO 178
<211> LENGTH: 20
<212> TYPE: DNA
<213> ORGANISM: Artificial sequence
<220> FEATURE:
<223> OTHER INFORMATION: Primer ACZ62391.1_11_ext_R_707

<400> SEQUENCE: 178
tagagtcatc ggctgagctt                                               20

<210> SEQ ID NO 179
<211> LENGTH: 20
<212> TYPE: DNA
<213> ORGANISM: Artificial sequence
<220> FEATURE:
<223> OTHER INFORMATION: Primer ACZ62391.1_13_ext_F_550
```

<400> SEQUENCE: 179
atgggagcgt accaaaatgg                                               20

<210> SEQ ID NO 180
<211> LENGTH: 20
<212> TYPE: DNA
<213> ORGANISM: Artificial sequence
<220> FEATURE:
<223> OTHER INFORMATION: Primer ACZ62391.1_13_ext_R_703

<400> SEQUENCE: 180
gtcatcggct gagctttctt                                               20

<210> SEQ ID NO 181
<211> LENGTH: 20
<212> TYPE: DNA
<213> ORGANISM: Artificial sequence
<220> FEATURE:
<223> OTHER INFORMATION: Primer ACZ62391.1_3_ext_F_550

<400> SEQUENCE: 181
atgggagcgt accaaaatgg                                               20

<210> SEQ ID NO 182
<211> LENGTH: 20
<212> TYPE: DNA
<213> ORGANISM: Artificial sequence
<220> FEATURE:
<223> OTHER INFORMATION: Primer ACZ62391.1_3_ext_R_667

<400> SEQUENCE: 182
catttgggat ctgccaggtt                                               20

<210> SEQ ID NO 183
<211> LENGTH: 20
<212> TYPE: DNA
<213> ORGANISM: Artificial sequence
<220> FEATURE:
<223> OTHER INFORMATION: Primer ACZ62391.1_6_ext_F_479

<400> SEQUENCE: 183
tcctgatcaa cccggtaagt                                               20

<210> SEQ ID NO 184
<211> LENGTH: 20
<212> TYPE: DNA
<213> ORGANISM: Artificial sequence
<220> FEATURE:
<223> OTHER INFORMATION: Primer ACZ62391.1_6_ext_R_667

<400> SEQUENCE: 184
catttgggat ctgccaggtt                                               20

<210> SEQ ID NO 185
<211> LENGTH: 20
<212> TYPE: DNA
<213> ORGANISM: Artificial sequence
<220> FEATURE:
<223> OTHER INFORMATION: Primer ACZ62413.1_0_spec_F_1196

<400> SEQUENCE: 185
acccaccacg cctatagatt                                               20

<210> SEQ ID NO 186
<211> LENGTH: 20

```
<212> TYPE: DNA
<213> ORGANISM: Artificial sequence
<220> FEATURE:
<223> OTHER INFORMATION: Primer ACZ62413.1_0_spec_R_1274

<400> SEQUENCE: 186
ctgagtcgga caggtttgag                                              20

<210> SEQ ID NO 187
<211> LENGTH: 20
<212> TYPE: DNA
<213> ORGANISM: Artificial sequence
<220> FEATURE:
<223> OTHER INFORMATION: Primer ACZ62419.1_0_spec_F_1235

<400> SEQUENCE: 187
tcttcctcta gcgcctactc                                              20

<210> SEQ ID NO 188
<211> LENGTH: 20
<212> TYPE: DNA
<213> ORGANISM: Artificial sequence
<220> FEATURE:
<223> OTHER INFORMATION: Primer ACZ62419.1_0_spec_R_1312

<400> SEQUENCE: 188
gcttcggcac atataccaca                                              20

<210> SEQ ID NO 189
<211> LENGTH: 19
<212> TYPE: DNA
<213> ORGANISM: Artificial sequence
<220> FEATURE:
<223> OTHER INFORMATION: Primer ACZ62419.1_30_spec_F_1150

<400> SEQUENCE: 189
taggtgagca cagccgtat                                               19

<210> SEQ ID NO 190
<211> LENGTH: 20
<212> TYPE: DNA
<213> ORGANISM: Artificial sequence
<220> FEATURE:
<223> OTHER INFORMATION: Primer ACZ62419.1_30_spec_R_1254

<400> SEQUENCE: 190
gagtaggcgc tagaggaaga                                              20

<210> SEQ ID NO 191
<211> LENGTH: 20
<212> TYPE: DNA
<213> ORGANISM: Artificial sequence
<220> FEATURE:
<223> OTHER INFORMATION: Primer ACZ62419.1_5_spec_F_1208

<400> SEQUENCE: 191
gcggactcat gctgtctttt                                              20

<210> SEQ ID NO 192
<211> LENGTH: 20
<212> TYPE: DNA
<213> ORGANISM: Artificial sequence
<220> FEATURE:
<223> OTHER INFORMATION: Primer ACZ62419.1_5_spec_R_1308

<400> SEQUENCE: 192
```
cggcacatat accacaggtc                                              20

<210> SEQ ID NO 193
<211> LENGTH: 20
<212> TYPE: DNA
<213> ORGANISM: Artificial sequence
<220> FEATURE:
<223> OTHER INFORMATION: Primer ACZ62441.1_2_spec_F_1111

<400> SEQUENCE: 193
gggctgccat gactattgag                                              20

<210> SEQ ID NO 194
<211> LENGTH: 20
<212> TYPE: DNA
<213> ORGANISM: Artificial sequence
<220> FEATURE:
<223> OTHER INFORMATION: Primer ACZ62441.1_2_spec_R_1237

<400> SEQUENCE: 194
cagttgtgac aaaagcgacg                                              20

<210> SEQ ID NO 195
<211> LENGTH: 20
<212> TYPE: DNA
<213> ORGANISM: Artificial sequence
<220> FEATURE:
<223> OTHER INFORMATION: Primer ACZ62459.1_179_spec_F_1518

<400> SEQUENCE: 195
ggtgtttacg aacctccgaa                                              20

<210> SEQ ID NO 196
<211> LENGTH: 20
<212> TYPE: DNA
<213> ORGANISM: Artificial sequence
<220> FEATURE:
<223> OTHER INFORMATION: Primer ACZ62459.1_179_spec_R_1594

<400> SEQUENCE: 196
ttcaccccca tcggagtatt                                              20

<210> SEQ ID NO 197
<211> LENGTH: 20
<212> TYPE: DNA
<213> ORGANISM: Artificial sequence
<220> FEATURE:
<223> OTHER INFORMATION: Primer ACZ62459.1_430_spec_F_112

<400> SEQUENCE: 197
cattctccat gcagggtcag                                              20

<210> SEQ ID NO 198
<211> LENGTH: 20
<212> TYPE: DNA
<213> ORGANISM: Artificial sequence
<220> FEATURE:
<223> OTHER INFORMATION: Primer ACZ62459.1_430_spec_R_206

<400> SEQUENCE: 198
ttcccagctg aaagggtaa                                               20

<210> SEQ ID NO 199
<211> LENGTH: 20
<212> TYPE: DNA
<213> ORGANISM: Artificial sequence -continued

```
<220> FEATURE:
<223> OTHER INFORMATION: Primer ACZ62477.1_52_ext_F_809

<400> SEQUENCE: 199
tgccataccc aacaaatgca                                           20

<210> SEQ ID NO 200
<211> LENGTH: 20
<212> TYPE: DNA
<213> ORGANISM: Artificial sequence
<220> FEATURE:
<223> OTHER INFORMATION: Primer ACZ62477.1_52_ext_R_913

<400> SEQUENCE: 200
taccagaccg caaaaccttc                                           20

<210> SEQ ID NO 201
<211> LENGTH: 20
<212> TYPE: DNA
<213> ORGANISM: Artificial sequence
<220> FEATURE:
<223> OTHER INFORMATION: Primer ACZ62477.1_760_ext_F_809

<400> SEQUENCE: 201
tgccataccc aacaaatgca                                           20

<210> SEQ ID NO 202
<211> LENGTH: 20
<212> TYPE: DNA
<213> ORGANISM: Artificial sequence
<220> FEATURE:
<223> OTHER INFORMATION: Primer ACZ62477.1_760_ext_R_927

<400> SEQUENCE: 202
agcgggcata agaataccag                                           20

<210> SEQ ID NO 203
<211> LENGTH: 20
<212> TYPE: DNA
<213> ORGANISM: Artificial sequence
<220> FEATURE:
<223> OTHER INFORMATION: Primer ACZ62477.1_782_spec_F_809

<400> SEQUENCE: 203
tgccataccc aacaaatgca                                           20

<210> SEQ ID NO 204
<211> LENGTH: 20
<212> TYPE: DNA
<213> ORGANISM: Artificial sequence
<220> FEATURE:
<223> OTHER INFORMATION: Primer ACZ62477.1_782_spec_R_914

<400> SEQUENCE: 204
ataccagacc gcaaaacctt                                           20

<210> SEQ ID NO 205
<211> LENGTH: 20
<212> TYPE: DNA
<213> ORGANISM: Artificial sequence
<220> FEATURE:
<223> OTHER INFORMATION: Primer ACZ62486.1_0_ext_F_1024

<400> SEQUENCE: 205
gcggtgttat gactcccaaa                                           20
```

```
<210> SEQ ID NO 206
<211> LENGTH: 20
<212> TYPE: DNA
<213> ORGANISM: Artificial sequence
<220> FEATURE:
<223> OTHER INFORMATION: Primer ACZ62486.1_0_ext_R_1187

<400> SEQUENCE: 206
cttgctgata gctcccatcg                                          20

<210> SEQ ID NO 207
<211> LENGTH: 21
<212> TYPE: DNA
<213> ORGANISM: Artificial sequence
<220> FEATURE:
<223> OTHER INFORMATION: Primer ACZ62486.1_1038_spec_F_926

<400> SEQUENCE: 207
gggtctggga tatatctcgc t                                        21

<210> SEQ ID NO 208
<211> LENGTH: 20
<212> TYPE: DNA
<213> ORGANISM: Artificial sequence
<220> FEATURE:
<223> OTHER INFORMATION: Primer ACZ62486.1_1038_spec_R_1071

<400> SEQUENCE: 208
cgtgcattac ccgtacagag                                          20

<210> SEQ ID NO 209
<211> LENGTH: 20
<212> TYPE: DNA
<213> ORGANISM: Artificial sequence
<220> FEATURE:
<223> OTHER INFORMATION: Primer ACZ62486.1_319_spec_F_920

<400> SEQUENCE: 209
cctgtggggt ctgggatata                                          20

<210> SEQ ID NO 210
<211> LENGTH: 20
<212> TYPE: DNA
<213> ORGANISM: Artificial sequence
<220> FEATURE:
<223> OTHER INFORMATION: Primer ACZ62486.1_319_spec_R_1071

<400> SEQUENCE: 210
cgtgcattac ccgtacagag                                          20

<210> SEQ ID NO 211
<211> LENGTH: 20
<212> TYPE: DNA
<213> ORGANISM: Artificial sequence
<220> FEATURE:
<223> OTHER INFORMATION: Primer ACZ62486.1_47_spec_F_1024

<400> SEQUENCE: 211
gcggtgttat gactcccaaa                                          20

<210> SEQ ID NO 212
<211> LENGTH: 20
<212> TYPE: DNA
<213> ORGANISM: Artificial sequence
<220> FEATURE:
<223> OTHER INFORMATION: Primer ACZ62486.1_47_spec_R_1195
```

```
<400> SEQUENCE: 212
ggctcatcct tgctgatagc                                               20

<210> SEQ ID NO 213
<211> LENGTH: 21
<212> TYPE: DNA
<213> ORGANISM: Artificial sequence
<220> FEATURE:
<223> OTHER INFORMATION: Primer ACZ62486.1_970_ext_F_931

<400> SEQUENCE: 213
tgggatatat ctcgctggac a                                             21

<210> SEQ ID NO 214
<211> LENGTH: 20
<212> TYPE: DNA
<213> ORGANISM: Artificial sequence
<220> FEATURE:
<223> OTHER INFORMATION: Primer ACZ62486.1_970_ext_R_1043

<400> SEQUENCE: 214
tttgggagtc ataacaccgc                                               20

<210> SEQ ID NO 215
<211> LENGTH: 19
<212> TYPE: DNA
<213> ORGANISM: Artificial sequence
<220> FEATURE:
<223> OTHER INFORMATION: Primer ACZ62486.1_983_spec_F_113

<400> SEQUENCE: 215
tgaaatggct tcagcaccc                                                19

<210> SEQ ID NO 216
<211> LENGTH: 20
<212> TYPE: DNA
<213> ORGANISM: Artificial sequence
<220> FEATURE:
<223> OTHER INFORMATION: Primer ACZ62486.1_983_spec_R_245

<400> SEQUENCE: 216
cataggggga gggcctttat                                               20

<210> SEQ ID NO 217
<211> LENGTH: 20
<212> TYPE: DNA
<213> ORGANISM: Artificial sequence
<220> FEATURE:
<223> OTHER INFORMATION: Primer ACZ62492.1_147_spec_F_814

<400> SEQUENCE: 217
ggactatgcg tcagccatac                                               20

<210> SEQ ID NO 218
<211> LENGTH: 20
<212> TYPE: DNA
<213> ORGANISM: Artificial sequence
<220> FEATURE:
<223> OTHER INFORMATION: Primer ACZ62492.1_147_spec_R_916

<400> SEQUENCE: 218
tgggctttgg tattgtaggc                                               20

<210> SEQ ID NO 219
```

```
<211> LENGTH: 20
<212> TYPE: DNA
<213> ORGANISM: Artificial sequence
<220> FEATURE:
<223> OTHER INFORMATION: Primer ACZ62492.1_799_spec_F_814

<400> SEQUENCE: 219
ggactatgcg tcagccatac                                                    20

<210> SEQ ID NO 220
<211> LENGTH: 20
<212> TYPE: DNA
<213> ORGANISM: Artificial sequence
<220> FEATURE:
<223> OTHER INFORMATION: Primer ACZ62492.1_799_spec_R_923

<400> SEQUENCE: 220
ctggaagtgg gctttggtat                                                    20

<210> SEQ ID NO 221
<211> LENGTH: 20
<212> TYPE: DNA
<213> ORGANISM: Artificial sequence
<220> FEATURE:
<223> OTHER INFORMATION: Primer ACZ62501.1_1067_spec_F_1077

<400> SEQUENCE: 221
atgtggcgtt tctgccatac                                                    20

<210> SEQ ID NO 222
<211> LENGTH: 20
<212> TYPE: DNA
<213> ORGANISM: Artificial sequence
<220> FEATURE:
<223> OTHER INFORMATION: Primer ACZ62501.1_1067_spec_R_1219

<400> SEQUENCE: 222
aactgtttct tgccgggtac                                                    20

<210> SEQ ID NO 223
<211> LENGTH: 20
<212> TYPE: DNA
<213> ORGANISM: Artificial sequence
<220> FEATURE:
<223> OTHER INFORMATION: Primer ACZ62501.1_2033_spec_F_1084

<400> SEQUENCE: 223
gtttctgcca tacctgcacc                                                    20

<210> SEQ ID NO 224
<211> LENGTH: 20
<212> TYPE: DNA
<213> ORGANISM: Artificial sequence
<220> FEATURE:
<223> OTHER INFORMATION: Primer ACZ62501.1_2033_spec_R_1219

<400> SEQUENCE: 224
aactgtttct tgccgggtac                                                    20

<210> SEQ ID NO 225
<211> LENGTH: 20
<212> TYPE: DNA
<213> ORGANISM: Artificial sequence
<220> FEATURE:
<223> OTHER INFORMATION: Primer ACZ62520.1_209_spec_F_874

<400> SEQUENCE: 225
```
ctgctaccct taccggtttg                                          20

<210> SEQ ID NO 226
<211> LENGTH: 20
<212> TYPE: DNA
<213> ORGANISM: Artificial sequence
<220> FEATURE:
<223> OTHER INFORMATION: Primer ACZ62520.1_209_spec_R_1013

<400> SEQUENCE: 226
cataccggca tcaatgggag                                          20

<210> SEQ ID NO 227
<211> LENGTH: 20
<212> TYPE: DNA
<213> ORGANISM: Artificial sequence
<220> FEATURE:
<223> OTHER INFORMATION: Primer ACZ62520.1_3576_ext_F_994

<400> SEQUENCE: 227
ctcccattga tgccggtatg                                          20

<210> SEQ ID NO 228
<211> LENGTH: 19
<212> TYPE: DNA
<213> ORGANISM: Artificial sequence
<220> FEATURE:
<223> OTHER INFORMATION: Primer ACZ62520.1_3576_ext_R_1095

<400> SEQUENCE: 228
cccaggttgg ttcatgctc                                           19

<210> SEQ ID NO 229
<211> LENGTH: 19
<212> TYPE: DNA
<213> ORGANISM: Artificial sequence
<220> FEATURE:
<223> OTHER INFORMATION: Primer ACZ62520.1_3979_ext_F_882

<400> SEQUENCE: 229
cttaccggtt tgggtgagg                                           19

<210> SEQ ID NO 230
<211> LENGTH: 20
<212> TYPE: DNA
<213> ORGANISM: Artificial sequence
<220> FEATURE:
<223> OTHER INFORMATION: Primer ACZ62520.1_3979_ext_R_1006

<400> SEQUENCE: 230
gcatcaatgg gaggtgtagg                                          20

<210> SEQ ID NO 231
<211> LENGTH: 20
<212> TYPE: DNA
<213> ORGANISM: Artificial sequence
<220> FEATURE:
<223> OTHER INFORMATION: Primer ACZ62520.1_768_spec_F_866

<400> SEQUENCE: 231
cattgccact gctaccctta                                          20

<210> SEQ ID NO 232
<211> LENGTH: 20
<212> TYPE: DNA

-continued

```
<213> ORGANISM: Artificial sequence
<220> FEATURE:
<223> OTHER INFORMATION: Primer ACZ62520.1_768_spec_R_1006

<400> SEQUENCE: 232
gcatcaatgg gaggtgtagg                                                20

<210> SEQ ID NO 233
<211> LENGTH: 19
<212> TYPE: DNA
<213> ORGANISM: Artificial sequence
<220> FEATURE:
<223> OTHER INFORMATION: Primer ACZ62529.1_1422_spec_F_1329

<400> SEQUENCE: 233
accaccggca ttttcaaca                                                 19

<210> SEQ ID NO 234
<211> LENGTH: 20
<212> TYPE: DNA
<213> ORGANISM: Artificial sequence
<220> FEATURE:
<223> OTHER INFORMATION: Primer ACZ62529.1_1422_spec_R_1418

<400> SEQUENCE: 234
gtcaagatcc caccattcgg                                                20

<210> SEQ ID NO 235
<211> LENGTH: 19
<212> TYPE: DNA
<213> ORGANISM: Artificial sequence
<220> FEATURE:
<223> OTHER INFORMATION: Primer ACZ62529.1_1912_spec_F_1073

<400> SEQUENCE: 235
tttccgcttc tgccatagc                                                 19

<210> SEQ ID NO 236
<211> LENGTH: 20
<212> TYPE: DNA
<213> ORGANISM: Artificial sequence
<220> FEATURE:
<223> OTHER INFORMATION: Primer ACZ62529.1_1912_spec_R_1223

<400> SEQUENCE: 236
cagcttgcac tcaggttcat                                                20

<210> SEQ ID NO 237
<211> LENGTH: 20
<212> TYPE: DNA
<213> ORGANISM: Artificial sequence
<220> FEATURE:
<223> OTHER INFORMATION: Primer ACZ62529.1_3935_ext_F_1257

<400> SEQUENCE: 237
tgtaccggcg tttgtgtatt                                                20

<210> SEQ ID NO 238
<211> LENGTH: 19
<212> TYPE: DNA
<213> ORGANISM: Artificial sequence
<220> FEATURE:
<223> OTHER INFORMATION: Primer ACZ62529.1_3935_ext_R_1416

<400> SEQUENCE: 238
caagatccca ccattcggc                                                 19
```

<210> SEQ ID NO 239
<211> LENGTH: 20
<212> TYPE: DNA
<213> ORGANISM: Artificial sequence
<220> FEATURE:
<223> OTHER INFORMATION: Primer ACZ62529.1_746_spec_F_796

<400> SEQUENCE: 239
gtgtttgtta tgccgccaat                                               20

<210> SEQ ID NO 240
<211> LENGTH: 20
<212> TYPE: DNA
<213> ORGANISM: Artificial sequence
<220> FEATURE:
<223> OTHER INFORMATION: Primer ACZ62529.1_746_spec_R_901

<400> SEQUENCE: 240
gcagactgca aaccctgata                                               20

<210> SEQ ID NO 241
<211> LENGTH: 19
<212> TYPE: DNA
<213> ORGANISM: Artificial sequence
<220> FEATURE:
<223> OTHER INFORMATION: Primer ACZ62535.1_2901_spec_F_978

<400> SEQUENCE: 241
cgttatgtgg gttccgagg                                                19

<210> SEQ ID NO 242
<211> LENGTH: 20
<212> TYPE: DNA
<213> ORGANISM: Artificial sequence
<220> FEATURE:
<223> OTHER INFORMATION: Primer ACZ62535.1_2901_spec_R_1152

<400> SEQUENCE: 242
agaaacggta aatgcctgca                                               20

<210> SEQ ID NO 243
<211> LENGTH: 19
<212> TYPE: DNA
<213> ORGANISM: Artificial sequence
<220> FEATURE:
<223> OTHER INFORMATION: Primer ACZ62535.1_2902_spec_F_977

<400> SEQUENCE: 243
ccgttatgtg ggttccgag                                                19

<210> SEQ ID NO 244
<211> LENGTH: 20
<212> TYPE: DNA
<213> ORGANISM: Artificial sequence
<220> FEATURE:
<223> OTHER INFORMATION: Primer ACZ62535.1_2902_spec_R_1152

<400> SEQUENCE: 244
agaaacggta aatgcctgca                                               20

<210> SEQ ID NO 245
<211> LENGTH: 20
<212> TYPE: DNA
<213> ORGANISM: Artificial sequence
<220> FEATURE:

<223> OTHER INFORMATION: Primer ACZ62535.1_325_spec_F_1133

<400> SEQUENCE: 245
tgcaggcatt taccgtttct                     20

<210> SEQ ID NO 246
<211> LENGTH: 20
<212> TYPE: DNA
<213> ORGANISM: Artificial sequence
<220> FEATURE:
<223> OTHER INFORMATION: Primer ACZ62535.1_325_spec_R_1323

<400> SEQUENCE: 246
tttcgttgga atactggcgg                     20

<210> SEQ ID NO 247
<211> LENGTH: 20
<212> TYPE: DNA
<213> ORGANISM: Artificial sequence
<220> FEATURE:
<223> OTHER INFORMATION: Primer ACZ62535.1_4389_spec_F_1133

<400> SEQUENCE: 247
tgcaggcatt taccgtttct                     20

<210> SEQ ID NO 248
<211> LENGTH: 19
<212> TYPE: DNA
<213> ORGANISM: Artificial sequence
<220> FEATURE:
<223> OTHER INFORMATION: Primer ACZ62535.1_4389_spec_R_1315

<400> SEQUENCE: 248
gaatactggc ggcagagag                      19

<210> SEQ ID NO 249
<211> LENGTH: 20
<212> TYPE: DNA
<213> ORGANISM: Artificial sequence
<220> FEATURE:
<223> OTHER INFORMATION: Primer ADC73508.1_197_ext_F_106

<400> SEQUENCE: 249
tgttccgcgg ctttgaaata                     20

<210> SEQ ID NO 250
<211> LENGTH: 20
<212> TYPE: DNA
<213> ORGANISM: Artificial sequence
<220> FEATURE:
<223> OTHER INFORMATION: Primer ADC73508.1_197_ext_R_275

<400> SEQUENCE: 250
gagtatccgc ccgttattcg                     20

<210> SEQ ID NO 251
<211> LENGTH: 20
<212> TYPE: DNA
<213> ORGANISM: Artificial sequence
<220> FEATURE:
<223> OTHER INFORMATION: Primer ADC73508.1_20_spec_F_1019

<400> SEQUENCE: 251
ccgctatgaa aacaccccctt                    20

-continued

```
<210> SEQ ID NO 252
<211> LENGTH: 20
<212> TYPE: DNA
<213> ORGANISM: Artificial sequence
<220> FEATURE:
<223> OTHER INFORMATION: Primer ADC73508.1_20_spec_R_1205

<400> SEQUENCE: 252
agccacaatc ttgcattcca                                               20

<210> SEQ ID NO 253
<211> LENGTH: 20
<212> TYPE: DNA
<213> ORGANISM: Artificial sequence
<220> FEATURE:
<223> OTHER INFORMATION: Primer ADC73508.1_202_spec_F_916

<400> SEQUENCE: 253
tcaagtacgg ctggttcaag                                               20

<210> SEQ ID NO 254
<211> LENGTH: 20
<212> TYPE: DNA
<213> ORGANISM: Artificial sequence
<220> FEATURE:
<223> OTHER INFORMATION: Primer ADC73508.1_202_spec_R_1038

<400> SEQUENCE: 254
aaggggtgtt ttcatagcgg                                               20

<210> SEQ ID NO 255
<211> LENGTH: 20
<212> TYPE: DNA
<213> ORGANISM: Artificial sequence
<220> FEATURE:
<223> OTHER INFORMATION: Primer ADC73508.1_3_spec_F_877

<400> SEQUENCE: 255
cactccacac ctttgatccc                                               20

<210> SEQ ID NO 256
<211> LENGTH: 20
<212> TYPE: DNA
<213> ORGANISM: Artificial sequence
<220> FEATURE:
<223> OTHER INFORMATION: Primer ADC73508.1_3_spec_R_1038

<400> SEQUENCE: 256
aaggggtgtt ttcatagcgg                                               20

<210> SEQ ID NO 257
<211> LENGTH: 20
<212> TYPE: DNA
<213> ORGANISM: Artificial sequence
<220> FEATURE:
<223> OTHER INFORMATION: Primer ADC73508.1_338_ext_F_49

<400> SEQUENCE: 257
aaatcgaagc caccgtagac                                               20

<210> SEQ ID NO 258
<211> LENGTH: 20
<212> TYPE: DNA
<213> ORGANISM: Artificial sequence
<220> FEATURE:
<223> OTHER INFORMATION: Primer ADC73508.1_338_ext_R_125
```

<400> SEQUENCE: 258
tatttcaaag ccgcggaaca                                               20

<210> SEQ ID NO 259
<211> LENGTH: 20
<212> TYPE: DNA
<213> ORGANISM: Artificial sequence
<220> FEATURE:
<223> OTHER INFORMATION: Primer ADC74627.1_1_spec_F_757

<400> SEQUENCE: 259
cggcagtaaa tcccaccaat                                               20

<210> SEQ ID NO 260
<211> LENGTH: 20
<212> TYPE: DNA
<213> ORGANISM: Artificial sequence
<220> FEATURE:
<223> OTHER INFORMATION: Primer ADC74627.1_1_spec_R_876

<400> SEQUENCE: 260
gtgcagcgtt ctgagtagtt                                               20

<210> SEQ ID NO 261
<211> LENGTH: 20
<212> TYPE: DNA
<213> ORGANISM: Artificial sequence
<220> FEATURE:
<223> OTHER INFORMATION: Primer ADC74627.1_2_spec_F_757

<400> SEQUENCE: 261
cggcagtaaa tcccaccaat                                               20

<210> SEQ ID NO 262
<211> LENGTH: 20
<212> TYPE: DNA
<213> ORGANISM: Artificial sequence
<220> FEATURE:
<223> OTHER INFORMATION: Primer ADC74627.1_2_spec_R_875

<400> SEQUENCE: 262
tgcagcgttc tgagtagttg                                               20

<210> SEQ ID NO 263
<211> LENGTH: 20
<212> TYPE: DNA
<213> ORGANISM: Artificial sequence
<220> FEATURE:
<223> OTHER INFORMATION: Primer ADC74627.1_9_spec_F_741

<400> SEQUENCE: 263
gattttgtat gcacaccggc                                               20

<210> SEQ ID NO 264
<211> LENGTH: 20
<212> TYPE: DNA
<213> ORGANISM: Artificial sequence
<220> FEATURE:
<223> OTHER INFORMATION: Primer ADC74627.1_9_spec_R_876

<400> SEQUENCE: 264
gtgcagcgtt ctgagtagtt                                               20

<210> SEQ ID NO 265
<211> LENGTH: 20

-continued

<212> TYPE: DNA
<213> ORGANISM: Artificial sequence
<220> FEATURE:
<223> OTHER INFORMATION: Primer ADC74655.1_1033_spec_F_656

<400> SEQUENCE: 265
atccgttcca ggcaataagc                                        20

<210> SEQ ID NO 266
<211> LENGTH: 20
<212> TYPE: DNA
<213> ORGANISM: Artificial sequence
<220> FEATURE:
<223> OTHER INFORMATION: Primer ADC74655.1_1033_spec_R_792

<400> SEQUENCE: 266
gcagaaaccc gtcacatgaa                                        20

<210> SEQ ID NO 267
<211> LENGTH: 20
<212> TYPE: DNA
<213> ORGANISM: Artificial sequence
<220> FEATURE:
<223> OTHER INFORMATION: Primer ADC74655.1_1058_spec_F_656

<400> SEQUENCE: 267
atccgttcca ggcaataagc                                        20

<210> SEQ ID NO 268
<211> LENGTH: 20
<212> TYPE: DNA
<213> ORGANISM: Artificial sequence
<220> FEATURE:
<223> OTHER INFORMATION: Primer ADC74655.1_1058_spec_R_749

<400> SEQUENCE: 268
cttttgcgaa gtggggatgt                                        20

<210> SEQ ID NO 269
<211> LENGTH: 20
<212> TYPE: DNA
<213> ORGANISM: Artificial sequence
<220> FEATURE:
<223> OTHER INFORMATION: Primer ADC74655.1_161_ext_F_876

<400> SEQUENCE: 269
cagtttatcc gcgggttagg                                        20

<210> SEQ ID NO 270
<211> LENGTH: 20
<212> TYPE: DNA
<213> ORGANISM: Artificial sequence
<220> FEATURE:
<223> OTHER INFORMATION: Primer ADC74655.1_161_ext_R_983

<400> SEQUENCE: 270
ctgacccata cggcaatgtt                                        20

<210> SEQ ID NO 271
<211> LENGTH: 20
<212> TYPE: DNA
<213> ORGANISM: Artificial sequence
<220> FEATURE:
<223> OTHER INFORMATION: Primer ADC74655.1_166_ext_F_876

<400> SEQUENCE: 271

-continued cagtttatcc gcgggttagg                                        20

<210> SEQ ID NO 272
<211> LENGTH: 20
<212> TYPE: DNA
<213> ORGANISM: Artificial sequence
<220> FEATURE:
<223> OTHER INFORMATION: Primer ADC74655.1_166_ext_R_982

<400> SEQUENCE: 272
tgacccatac ggcaatgttc                                        20

<210> SEQ ID NO 273
<211> LENGTH: 20
<212> TYPE: DNA
<213> ORGANISM: Artificial sequence
<220> FEATURE:
<223> OTHER INFORMATION: Primer ADC74655.1_2926_ext_F_950

<400> SEQUENCE: 273
gagcggtgtt ggtgaacatt                                        20

<210> SEQ ID NO 274
<211> LENGTH: 20
<212> TYPE: DNA
<213> ORGANISM: Artificial sequence
<220> FEATURE:
<223> OTHER INFORMATION: Primer ADC74655.1_2926_ext_R_1120

<400> SEQUENCE: 274
gtttcagcac agataccgca                                        20

<210> SEQ ID NO 275
<211> LENGTH: 20
<212> TYPE: DNA
<213> ORGANISM: Artificial sequence
<220> FEATURE:
<223> OTHER INFORMATION: Primer BAE84628.1_1113_spec_F_317

<400> SEQUENCE: 275
aaatgcggaa agacttggga                                        20

<210> SEQ ID NO 276
<211> LENGTH: 20
<212> TYPE: DNA
<213> ORGANISM: Artificial sequence
<220> FEATURE:
<223> OTHER INFORMATION: Primer BAE84628.1_1113_spec_R_411

<400> SEQUENCE: 276
gggttaacat ggcacccaaa                                        20

<210> SEQ ID NO 277
<211> LENGTH: 20
<212> TYPE: DNA
<213> ORGANISM: Artificial sequence
<220> FEATURE:
<223> OTHER INFORMATION: Primer BAE84628.1_3406_ext_F_1459

<400> SEQUENCE: 277
ggaacaaagt cgagacctgg                                        20

<210> SEQ ID NO 278
<211> LENGTH: 19
<212> TYPE: DNA
<213> ORGANISM: Artificial sequence

```
<220> FEATURE:
<223> OTHER INFORMATION: Primer BAE84628.1_3406_ext_R_1546

<400> SEQUENCE: 278
tcatcaaact tgcgggctg                                                 19

<210> SEQ ID NO 279
<211> LENGTH: 20
<212> TYPE: DNA
<213> ORGANISM: Artificial sequence
<220> FEATURE:
<223> OTHER INFORMATION: Primer BAE84628.1_400_spec_F_317

<400> SEQUENCE: 279
aaatgcggaa agacttggga                                                20

<210> SEQ ID NO 280
<211> LENGTH: 20
<212> TYPE: DNA
<213> ORGANISM: Artificial sequence
<220> FEATURE:
<223> OTHER INFORMATION: Primer BAE84628.1_400_spec_R_405

<400> SEQUENCE: 280
acatggcacc caaatgttga                                                20

<210> SEQ ID NO 281
<211> LENGTH: 20
<212> TYPE: DNA
<213> ORGANISM: Artificial sequence
<220> FEATURE:
<223> OTHER INFORMATION: Primer BAE84628.1_4184_ext_F_1102

<400> SEQUENCE: 281
gtgttcctat ggccgttcag                                                20

<210> SEQ ID NO 282
<211> LENGTH: 19
<212> TYPE: DNA
<213> ORGANISM: Artificial sequence
<220> FEATURE:
<223> OTHER INFORMATION: Primer BAE84628.1_4184_ext_R_1229

<400> SEQUENCE: 282
cttgtccgga gcaagttcc                                                 19

<210> SEQ ID NO 283
<211> LENGTH: 20
<212> TYPE: DNA
<213> ORGANISM: Artificial sequence
<220> FEATURE:
<223> OTHER INFORMATION: Primer BAF34982.1_9_spec_F_1138

<400> SEQUENCE: 283
gggaacaatc acgcgtatca                                                20

<210> SEQ ID NO 284
<211> LENGTH: 20
<212> TYPE: DNA
<213> ORGANISM: Artificial sequence
<220> FEATURE:
<223> OTHER INFORMATION: Primer BAF34982.1_9_spec_R_1251

<400> SEQUENCE: 284
cggcatctat aggcttggtg                                                20
```

<210> SEQ ID NO 285
<211> LENGTH: 20
<212> TYPE: DNA
<213> ORGANISM: Artificial sequence
<220> FEATURE:
<223> OTHER INFORMATION: Primer BAG72170.1_2661_spec_F_1104

<400> SEQUENCE: 285
cctgcaagaa gtgtgcagat                                              20

<210> SEQ ID NO 286
<211> LENGTH: 19
<212> TYPE: DNA
<213> ORGANISM: Artificial sequence
<220> FEATURE:
<223> OTHER INFORMATION: Primer BAG72170.1_2661_spec_R_1200

<400> SEQUENCE: 286
actctgggtt tgccgtcta                                               19

<210> SEQ ID NO 287
<211> LENGTH: 20
<212> TYPE: DNA
<213> ORGANISM: Artificial sequence
<220> FEATURE:
<223> OTHER INFORMATION: Primer BAG72170.1_2758_spec_F_1001

<400> SEQUENCE: 287
actcctgaaa ccggtcctaa                                              20

<210> SEQ ID NO 288
<211> LENGTH: 19
<212> TYPE: DNA
<213> ORGANISM: Artificial sequence
<220> FEATURE:
<223> OTHER INFORMATION: Primer BAG72170.1_2758_spec_R_1111

<400> SEQUENCE: 288
cttgcaggag tggcagaag                                               19

<210> SEQ ID NO 289
<211> LENGTH: 20
<212> TYPE: DNA
<213> ORGANISM: Artificial sequence
<220> FEATURE:
<223> OTHER INFORMATION: Primer BAG72170.1_283_spec_F_1001

<400> SEQUENCE: 289
actcctgaaa ccggtcctaa                                              20

<210> SEQ ID NO 290
<211> LENGTH: 20
<212> TYPE: DNA
<213> ORGANISM: Artificial sequence
<220> FEATURE:
<223> OTHER INFORMATION: Primer BAG72170.1_283_spec_R_1123

<400> SEQUENCE: 290
atctgcacac ttcttgcagg                                              20

<210> SEQ ID NO 291
<211> LENGTH: 20
<212> TYPE: DNA
<213> ORGANISM: Artificial sequence
<220> FEATURE:
<223> OTHER INFORMATION: Primer BAG72170.1_866_spec_F_1029

<400> SEQUENCE: 291
cctttaccat gctgaccgat                                              20

<210> SEQ ID NO 292
<211> LENGTH: 20
<212> TYPE: DNA
<213> ORGANISM: Artificial sequence
<220> FEATURE:
<223> OTHER INFORMATION: Primer BAG72170.1_866_spec_R_1123

<400> SEQUENCE: 292
atctgcacac ttcttgcagg                                              20

<210> SEQ ID NO 293
<211> LENGTH: 20
<212> TYPE: DNA
<213> ORGANISM: Artificial sequence
<220> FEATURE:
<223> OTHER INFORMATION: Primer BAI47830.1_259_spec_F_251

<400> SEQUENCE: 293
agtgagcggc atttacaagg                                              20

<210> SEQ ID NO 294
<211> LENGTH: 20
<212> TYPE: DNA
<213> ORGANISM: Artificial sequence
<220> FEATURE:
<223> OTHER INFORMATION: Primer BAI47830.1_259_spec_R_348

<400> SEQUENCE: 294
gtagagccat agttgccacc                                              20

<210> SEQ ID NO 295
<211> LENGTH: 20
<212> TYPE: DNA
<213> ORGANISM: Artificial sequence
<220> FEATURE:
<223> OTHER INFORMATION: Primer BAI47830.1_561_spec_F_193

<400> SEQUENCE: 295
aatgcctggt ttccgtgaag                                              20

<210> SEQ ID NO 296
<211> LENGTH: 20
<212> TYPE: DNA
<213> ORGANISM: Artificial sequence
<220> FEATURE:
<223> OTHER INFORMATION: Primer BAI47830.1_561_spec_R_348

<400> SEQUENCE: 296
gtagagccat agttgccacc                                              20

<210> SEQ ID NO 297
<211> LENGTH: 20
<212> TYPE: DNA
<213> ORGANISM: Artificial sequence
<220> FEATURE:
<223> OTHER INFORMATION: Primer BAI70453.1_0_spec_F_309

<400> SEQUENCE: 297
tcttggttgg gtcctcagaa                                              20

<210> SEQ ID NO 298

```
<211> LENGTH: 20
<212> TYPE: DNA
<213> ORGANISM: Artificial sequence
<220> FEATURE:
<223> OTHER INFORMATION: Primer BAI70453.1_0_spec_R_459

<400> SEQUENCE: 298
cgttttcatc cagctccagt                                               20

<210> SEQ ID NO 299
<211> LENGTH: 20
<212> TYPE: DNA
<213> ORGANISM: Artificial sequence
<220> FEATURE:
<223> OTHER INFORMATION: Primer BAI70453.1_10_spec_F_718

<400> SEQUENCE: 299
tgggttatca ggctatggct                                               20

<210> SEQ ID NO 300
<211> LENGTH: 20
<212> TYPE: DNA
<213> ORGANISM: Artificial sequence
<220> FEATURE:
<223> OTHER INFORMATION: Primer BAI70453.1_10_spec_R_908

<400> SEQUENCE: 300
accggcatca ataggtttgg                                               20

<210> SEQ ID NO 301
<211> LENGTH: 20
<212> TYPE: DNA
<213> ORGANISM: Artificial sequence
<220> FEATURE:
<223> OTHER INFORMATION: Primer BAI70453.1_14_spec_F_182

<400> SEQUENCE: 301
acagaaaatt gcggcggata                                               20

<210> SEQ ID NO 302
<211> LENGTH: 20
<212> TYPE: DNA
<213> ORGANISM: Artificial sequence
<220> FEATURE:
<223> OTHER INFORMATION: Primer BAI70453.1_14_spec_R_342

<400> SEQUENCE: 302
cgggggtagg agatttctga                                               20

<210> SEQ ID NO 303
<211> LENGTH: 20
<212> TYPE: DNA
<213> ORGANISM: Artificial sequence
<220> FEATURE:
<223> OTHER INFORMATION: Primer BAI70453.1_28_ext_F_1104

<400> SEQUENCE: 303
gcctgtgtgt acaccaagaa                                               20

<210> SEQ ID NO 304
<211> LENGTH: 20
<212> TYPE: DNA
<213> ORGANISM: Artificial sequence
<220> FEATURE:
<223> OTHER INFORMATION: Primer BAI70453.1_28_ext_R_1289

<400> SEQUENCE: 304
```
ccagaaatct tcggcacctt                              20

<210> SEQ ID NO 305
<211> LENGTH: 20
<212> TYPE: DNA
<213> ORGANISM: Artificial sequence
<220> FEATURE:
<223> OTHER INFORMATION: Primer BAI70453.1_44_ext_F_1046

<400> SEQUENCE: 305
ggtgaaatgc cagagtaccc                              20

<210> SEQ ID NO 306
<211> LENGTH: 20
<212> TYPE: DNA
<213> ORGANISM: Artificial sequence
<220> FEATURE:
<223> OTHER INFORMATION: Primer BAI70453.1_44_ext_R_1241

<400> SEQUENCE: 306
gtcaggcccg aattcagtac                              20

<210> SEQ ID NO 307
<211> LENGTH: 20
<212> TYPE: DNA
<213> ORGANISM: Artificial sequence
<220> FEATURE:
<223> OTHER INFORMATION: Primer BAI70453.1_45_ext_F_927

<400> SEQUENCE: 307
gactgcgcta aatgctctga                              20

<210> SEQ ID NO 308
<211> LENGTH: 20
<212> TYPE: DNA
<213> ORGANISM: Artificial sequence
<220> FEATURE:
<223> OTHER INFORMATION: Primer BAI70453.1_45_ext_R_1065

<400> SEQUENCE: 308
gggtactctg gcatttcacc                              20

<210> SEQ ID NO 309
<211> LENGTH: 20
<212> TYPE: DNA
<213> ORGANISM: Artificial sequence
<220> FEATURE:
<223> OTHER INFORMATION: Primer BAI70453.1_6_spec_F_16

<400> SEQUENCE: 309
tgataacttc tggtgctgcg                              20

<210> SEQ ID NO 310
<211> LENGTH: 20
<212> TYPE: DNA
<213> ORGANISM: Artificial sequence
<220> FEATURE:
<223> OTHER INFORMATION: Primer BAI70453.1_6_spec_R_126

<400> SEQUENCE: 310
taaccttacg ggcgtcaaac                              20

<210> SEQ ID NO 311
<211> LENGTH: 20
<212> TYPE: DNA

```
<213> ORGANISM: Artificial sequence
<220> FEATURE:
<223> OTHER INFORMATION: Primer CAD28790.2_81_pr_F_209

<400> SEQUENCE: 311
tgaaaagact ttcgacccgg                                                  20

<210> SEQ ID NO 312
<211> LENGTH: 20
<212> TYPE: DNA
<213> ORGANISM: Artificial sequence
<220> FEATURE:
<223> OTHER INFORMATION: Primer CAD28790.2_81_pr_R_403

<400> SEQUENCE: 312
atggcaccca aatgttgagt                                                  20

<210> SEQ ID NO 313
<211> LENGTH: 20
<212> TYPE: DNA
<213> ORGANISM: Artificial sequence
<220> FEATURE:
<223> OTHER INFORMATION: Primer CAD28790.2_953_pr_F_385

<400> SEQUENCE: 313
ctcaacattt gggtgccatg                                                  20

<210> SEQ ID NO 314
<211> LENGTH: 20
<212> TYPE: DNA
<213> ORGANISM: Artificial sequence
<220> FEATURE:
<223> OTHER INFORMATION: Primer CAD28790.2_953_pr_R_484

<400> SEQUENCE: 314
tcaaattcta cagcccaggc                                                  20

<210> SEQ ID NO 315
<211> LENGTH: 19
<212> TYPE: DNA
<213> ORGANISM: Artificial sequence
<220> FEATURE:
<223> OTHER INFORMATION: Primer CAI83519.1_2479_spec_F_141

<400> SEQUENCE: 315
aacaaaaggc catggtggg                                                   19

<210> SEQ ID NO 316
<211> LENGTH: 20
<212> TYPE: DNA
<213> ORGANISM: Artificial sequence
<220> FEATURE:
<223> OTHER INFORMATION: Primer CAI83519.1_2479_spec_R_252

<400> SEQUENCE: 316
gagcagtcat gggataagcc                                                  20

<210> SEQ ID NO 317
<211> LENGTH: 20
<212> TYPE: DNA
<213> ORGANISM: Artificial sequence
<220> FEATURE:
<223> OTHER INFORMATION: Primer CAI83531.1_104_spec_F_1181

<400> SEQUENCE: 317
caccgattta cctctctcgc                                                  20
```

```
<210> SEQ ID NO 318
<211> LENGTH: 19
<212> TYPE: DNA
<213> ORGANISM: Artificial sequence
<220> FEATURE:
<223> OTHER INFORMATION: Primer CAI83531.1_104_spec_R_1267

<400> SEQUENCE: 318
caagcctcgg cacagatac                                               19

<210> SEQ ID NO 319
<211> LENGTH: 20
<212> TYPE: DNA
<213> ORGANISM: Artificial sequence
<220> FEATURE:
<223> OTHER INFORMATION: Primer CAI83566.1_1_spec_F_314

<400> SEQUENCE: 319
acaacgcatg caagatggta                                              20

<210> SEQ ID NO 320
<211> LENGTH: 20
<212> TYPE: DNA
<213> ORGANISM: Artificial sequence
<220> FEATURE:
<223> OTHER INFORMATION: Primer CAI83566.1_1_spec_R_464

<400> SEQUENCE: 320
gggaagtcct tgttcttcgg                                              20

<210> SEQ ID NO 321
<211> LENGTH: 20
<212> TYPE: DNA
<213> ORGANISM: Artificial sequence
<220> FEATURE:
<223> OTHER INFORMATION: Primer CAI83566.1_10_spec_F_444

<400> SEQUENCE: 321
cccgaagaac aaggacttcc                                              20

<210> SEQ ID NO 322
<211> LENGTH: 20
<212> TYPE: DNA
<213> ORGANISM: Artificial sequence
<220> FEATURE:
<223> OTHER INFORMATION: Primer CAI83566.1_10_spec_R_539

<400> SEQUENCE: 322
tacttgccct gcaccaaaaa                                              20

<210> SEQ ID NO 323
<211> LENGTH: 20
<212> TYPE: DNA
<213> ORGANISM: Artificial sequence
<220> FEATURE:
<223> OTHER INFORMATION: Primer CAI83566.1_14_spec_F_1161

<400> SEQUENCE: 323
cctggacaca aggcattctt                                              20

<210> SEQ ID NO 324
<211> LENGTH: 20
<212> TYPE: DNA
<213> ORGANISM: Artificial sequence
<220> FEATURE:
```

<223> OTHER INFORMATION: Primer CAI83566.1_14_spec_R_1247

<400> SEQUENCE: 324
catacagata ccgcagcctg                                                                  20

<210> SEQ ID NO 325
<211> LENGTH: 20
<212> TYPE: DNA
<213> ORGANISM: Artificial sequence
<220> FEATURE:
<223> OTHER INFORMATION: Primer CAI83566.1_4_spec_F_1134

<400> SEQUENCE: 325
aaatgggatt gtgcgcctta                                                                  20

<210> SEQ ID NO 326
<211> LENGTH: 20
<212> TYPE: DNA
<213> ORGANISM: Artificial sequence
<220> FEATURE:
<223> OTHER INFORMATION: Primer CAI83566.1_4_spec_R_1247

<400> SEQUENCE: 326
catacagata ccgcagcctg                                                                  20

<210> SEQ ID NO 327
<211> LENGTH: 20
<212> TYPE: DNA
<213> ORGANISM: Artificial sequence
<220> FEATURE:
<223> OTHER INFORMATION: Primer CAI83566.1_6_spec_F_445

<400> SEQUENCE: 327
ccgaagaaca aggacttccc                                                                  20

<210> SEQ ID NO 328
<211> LENGTH: 20
<212> TYPE: DNA
<213> ORGANISM: Artificial sequence
<220> FEATURE:
<223> OTHER INFORMATION: Primer CAI83566.1_6_spec_R_640

<400> SEQUENCE: 328
caagatgagc cgtacgtacc                                                                  20

<210> SEQ ID NO 329
<211> LENGTH: 20
<212> TYPE: DNA
<213> ORGANISM: Artificial sequence
<220> FEATURE:
<223> OTHER INFORMATION: Primer CAJ75430.1_2099_pr_F_321

<400> SEQUENCE: 329
gcggaaagac ttgggatcaa                                                                  20

<210> SEQ ID NO 330
<211> LENGTH: 19
<212> TYPE: DNA
<213> ORGANISM: Artificial sequence
<220> FEATURE:
<223> OTHER INFORMATION: Primer CAJ75430.1_2099_pr_R_408

<400> SEQUENCE: 330
gtggcatgac acccgtatg                                                                   19

-continued

```
<210> SEQ ID NO 331
<211> LENGTH: 20
<212> TYPE: DNA
<213> ORGANISM: Artificial sequence
<220> FEATURE:
<223> OTHER INFORMATION: Primer CAJ75430.1_2693_pr_F_280

<400> SEQUENCE: 331
caggcaagaa agatacgggg                                            20

<210> SEQ ID NO 332
<211> LENGTH: 19
<212> TYPE: DNA
<213> ORGANISM: Artificial sequence
<220> FEATURE:
<223> OTHER INFORMATION: Primer CAJ75430.1_2693_pr_R_408

<400> SEQUENCE: 332
gtggcatgac acccgtatg                                             19

<210> SEQ ID NO 333
<211> LENGTH: 20
<212> TYPE: DNA
<213> ORGANISM: Artificial sequence
<220> FEATURE:
<223> OTHER INFORMATION: Primer CAR57931.1_1638_pr_F_298

<400> SEQUENCE: 333
ggaaagacct gcccatactt                                            20

<210> SEQ ID NO 334
<211> LENGTH: 20
<212> TYPE: DNA
<213> ORGANISM: Artificial sequence
<220> FEATURE:
<223> OTHER INFORMATION: Primer CAR57931.1_1638_pr_R_372

<400> SEQUENCE: 334
cgcctgtttc tgcatttgtc                                            20

<210> SEQ ID NO 335
<211> LENGTH: 20
<212> TYPE: DNA
<213> ORGANISM: Artificial sequence
<220> FEATURE:
<223> OTHER INFORMATION: Primer CAR57931.1_2137_pr_F_298

<400> SEQUENCE: 335
ggaaagacct gcccatactt                                            20

<210> SEQ ID NO 336
<211> LENGTH: 20
<212> TYPE: DNA
<213> ORGANISM: Artificial sequence
<220> FEATURE:
<223> OTHER INFORMATION: Primer CAR57931.1_2137_pr_R_376

<400> SEQUENCE: 336
agaacgcctg tttctgcatt                                            20

<210> SEQ ID NO 337
<211> LENGTH: 22
<212> TYPE: DNA
<213> ORGANISM: Artificial sequence
<220> FEATURE:
<223> OTHER INFORMATION: Dehalobacter 16S Forward Primer
```

<400> SEQUENCE: 337
gttagggaag aacggcatct gt                                    22

<210> SEQ ID NO 338
<211> LENGTH: 22
<212> TYPE: DNA
<213> ORGANISM: Artificial sequence
<220> FEATURE:
<223> OTHER INFORMATION: Dehalobacter 16S RNA reverse primer

<400> SEQUENCE: 338
cctctcctgt cctcaagcca ta                                    22

<210> SEQ ID NO 339
<211> LENGTH: 17
<212> TYPE: DNA
<213> ORGANISM: Artificial sequence
<220> FEATURE:
<223> OTHER INFORMATION: Dehalococcoides/Dehalogimonas 16S RNA Forward
      Primer

<400> SEQUENCE: 339
gaggcagcag caaggaa                                          17

<210> SEQ ID NO 340
<211> LENGTH: 18
<212> TYPE: DNA
<213> ORGANISM: Artificial sequence
<220> FEATURE:
<223> OTHER INFORMATION: Dehalococcoides/Dehalogimonas 16S RNA Reverse
      Primer

<400> SEQUENCE: 340
ggcgggacac ttaaagcg                                         18

<210> SEQ ID NO 341
<211> LENGTH: 22
<212> TYPE: DNA
<213> ORGANISM: Artificial sequence
<220> FEATURE:
<223> OTHER INFORMATION: Dehalobacter 16S RNA Forward Primer

<400> SEQUENCE: 341
gcacaagcgg tggagcatgt gg                                    22

<210> SEQ ID NO 342
<211> LENGTH: 19
<212> TYPE: DNA
<213> ORGANISM: Artificial sequence
<220> FEATURE:
<223> OTHER INFORMATION: Dehalobacter 16S RNA Reverse Primer

<400> SEQUENCE: 342
acaatccgaa ctgagaacg                                        19

<210> SEQ ID NO 343
<211> LENGTH: 21
<212> TYPE: DNA
<213> ORGANISM: Artificial sequence
<220> FEATURE:
<223> OTHER INFORMATION: Dehalobacter 16S RNA Forward Primer

<400> SEQUENCE: 343
gattgacggt acctaacgag g                                     21

```
<210> SEQ ID NO 344
<211> LENGTH: 22
<212> TYPE: DNA
<213> ORGANISM: Artificial sequence
<220> FEATURE:
<223> OTHER INFORMATION: Dehalobacter 16S RNA Reverse Primer

<400> SEQUENCE: 344
tacagtttcc aatgctttac gg                                              22

<210> SEQ ID NO 345
<211> LENGTH: 18
<212> TYPE: DNA
<213> ORGANISM: Artificial sequence
<220> FEATURE:
<223> OTHER INFORMATION: Dehalococcoides 16S RNA Forwrd Primer

<400> SEQUENCE: 345
ggcgtaaagt gagcgtag                                                   18

<210> SEQ ID NO 346
<211> LENGTH: 18
<212> TYPE: DNA
<213> ORGANISM: Artificial sequence
<220> FEATURE:
<223> OTHER INFORMATION: Dehalococcoides 16S RNA Reverse Primer

<400> SEQUENCE: 346
gacaacctag aaaaccgc                                                   18

<210> SEQ ID NO 347
<211> LENGTH: 17
<212> TYPE: DNA
<213> ORGANISM: Artificial sequence
<220> FEATURE:
<223> OTHER INFORMATION: Dehalococcoides 16S RNA Forwrd Primer

<400> SEQUENCE: 347
gatgaacgct agcggcg                                                    17

<210> SEQ ID NO 348
<211> LENGTH: 20
<212> TYPE: DNA
<213> ORGANISM: Artificial sequence
<220> FEATURE:
<223> OTHER INFORMATION: Dehalococcoides 16S RNA Reverse Primer

<400> SEQUENCE: 348
cagaccagct accgatcgaa                                                 20

<210> SEQ ID NO 349
<211> LENGTH: 19
<212> TYPE: DNA
<213> ORGANISM: Artificial sequence
<220> FEATURE:
<223> OTHER INFORMATION: Dehalococcoides 16S RNA Forwrd Primer

<400> SEQUENCE: 349
gaagtagtga accgaaagg                                                  19

<210> SEQ ID NO 350
<211> LENGTH: 18
<212> TYPE: DNA
<213> ORGANISM: Artificial sequence
<220> FEATURE:
<223> OTHER INFORMATION: Dehalococcoides 16S RNA Reverse Primer
```

<400> SEQUENCE: 350
tctgtccatt gtagcgtg                                              18

<210> SEQ ID NO 351
<211> LENGTH: 23
<212> TYPE: DNA
<213> ORGANISM: Artificial sequence
<220> FEATURE:
<223> OTHER INFORMATION: Dehalococcoides 16S RNA Forwrd Primer

<400> SEQUENCE: 351
aaggcggttt tctaggttgt cac                                        23

<210> SEQ ID NO 352
<211> LENGTH: 17
<212> TYPE: DNA
<213> ORGANISM: Artificial sequence
<220> FEATURE:
<223> OTHER INFORMATION: Dehalococcoides 16S RNA Reverse Primer

<400> SEQUENCE: 352
cttcatgcat gtcaaat                                               17

<210> SEQ ID NO 353
<211> LENGTH: 25
<212> TYPE: DNA
<213> ORGANISM: Artificial sequence
<220> FEATURE:
<223> OTHER INFORMATION: Dehalogenimonas 16S RNA Forward Primer

<400> SEQUENCE: 353
ggtcatctga tactgttgga cttga                                      25

<210> SEQ ID NO 354
<211> LENGTH: 24
<212> TYPE: DNA
<213> ORGANISM: Artificial sequence
<220> FEATURE:
<223> OTHER INFORMATION: Dehalogenimonas 16S RNA Reverse Primer

<400> SEQUENCE: 354
acccagtgtt tagggcgtgg acta                                       24

<210> SEQ ID NO 355
<211> LENGTH: 21
<212> TYPE: DNA
<213> ORGANISM: Artificial sequence
<220> FEATURE:
<223> OTHER INFORMATION: Desulfitobacterium 16S RNA Forward primer

<400> SEQUENCE: 355
gtacgacgaa ggccttcggg t                                          21

<210> SEQ ID NO 356
<211> LENGTH: 20
<212> TYPE: DNA
<213> ORGANISM: Artificial sequence
<220> FEATURE:
<223> OTHER INFORMATION: Desulfitobacterium 16S RNA Forward primer

<400> SEQUENCE: 356
cccagggttg agccctaggt                                            20

<210> SEQ ID NO 357
<211> LENGTH: 22

```
<212> TYPE: DNA
<213> ORGANISM: Artificial sequence
<220> FEATURE:
<223> OTHER INFORMATION: Desulfitobacterium 16S RNA Forward primer

<400> SEQUENCE: 357
gcacaagcgg tggagcatgt gg                                            22

<210> SEQ ID NO 358
<211> LENGTH: 18
<212> TYPE: DNA
<213> ORGANISM: Artificial sequence
<220> FEATURE:
<223> OTHER INFORMATION: Desulfitobacterium 16S RNA Reverse primer,
      R = A or G

<400> SEQUENCE: 358
tatctagagt gctcracc                                                 18

<210> SEQ ID NO 359
<211> LENGTH: 17
<212> TYPE: DNA
<213> ORGANISM: Artificial sequence
<220> FEATURE:
<223> OTHER INFORMATION: Eubacterium 16S RNA Forward Primer

<400> SEQUENCE: 359
cctacgggag gcagcag                                                  17

<210> SEQ ID NO 360
<211> LENGTH: 18
<212> TYPE: DNA
<213> ORGANISM: Artificial sequence
<220> FEATURE:
<223> OTHER INFORMATION: Eubacterium 16S RNA Reverse Primer

<400> SEQUENCE: 360
attaccgcgg ctgctggc                                                 18

<210> SEQ ID NO 361
<211> LENGTH: 19
<212> TYPE: DNA
<213> ORGANISM: Artificial sequence
<220> FEATURE:
<223> OTHER INFORMATION: Geobacter 16S RNA Forward primer, W = A or T

<400> SEQUENCE: 361
aagcgttgtt cggawttat                                                19

<210> SEQ ID NO 362
<211> LENGTH: 19
<212> TYPE: DNA
<213> ORGANISM: Artificial sequence
<220> FEATURE:
<223> OTHER INFORMATION: Geobacter 16S RNA Reverse Primer

<400> SEQUENCE: 362
ggcactgcag gggtcaata                                                19

<210> SEQ ID NO 363
<211> LENGTH: 20
<212> TYPE: DNA
<213> ORGANISM: Artificial sequence
<220> FEATURE:
<223> OTHER INFORMATION: Geobacter 16S RNA Forward Primer

<400> SEQUENCE: 363
```

```
aggaagcacc ggctaactcc                                              20

<210> SEQ ID NO 364
<211> LENGTH: 17
<212> TYPE: DNA
<213> ORGANISM: Artificial sequence
<220> FEATURE:
<223> OTHER INFORMATION: Geobacter 16S RNA Reverse Primer, R = A or G

<400> SEQUENCE: 364
tacccgcrac acctagt                                                 17

<210> SEQ ID NO 365
<211> LENGTH: 18
<212> TYPE: DNA
<213> ORGANISM: Artificial sequence
<220> FEATURE:
<223> OTHER INFORMATION: Dehalococcoides 16S RNA Forward Primer

<400> SEQUENCE: 365
gggagtatcg accctctc                                                18

<210> SEQ ID NO 366
<211> LENGTH: 21
<212> TYPE: DNA
<213> ORGANISM: Artificial sequence
<220> FEATURE:
<223> OTHER INFORMATION: Dehalococcoides 16S RNA Reverse Primer

<400> SEQUENCE: 366
ggattagctc cagttcacac t                                            21
```

NANOLITER QPCR PLATFORM FOR PARALLEL QUANTITATIVE ASSESSMENT OF REDUCTIVE DEHALOGENASE GENES

CROSS-REFERENCE TO RELATED APPLICATION

This application claims priority to U.S. Provisional Application No. 61/968,578, entitled "A NANOLITER QPCR PLATFORM FOR PARALLEL, QUANTITATIVE ASSESSMENT OF REDUCTIVE DEHALOGENASE GENES AND POPULATIONS OF DEHALOGENATING MICROORGANISMS IN COMPLEX ENVIRONMENTS" filed on Mar. 21, 2014, the entirety of which is herein incorporated by reference.

STATEMENT REGARDING FEDERALLY SPONSORED RESEARCH OR DEVELOPMENT

This invention was made with government support under Grant No. MCB-1330832 awarded by the National Science Foundation. The government has certain rights in the invention.

FIELD OF THE DISCLOSURE

The present disclosure relates to methods of identifying reductive dehalogenase genes and populations of dehalogenating microorganisms in complex environments.

SEQUENCE LISTING

The present disclosure includes a sequence listing incorporated herein by reference in its entirety.

BACKGROUND

The bioremediation of groundwater aquifers and sediments contaminated with chlorinated aliphatic hydrocarbons (CAHs) depends on the activities of reductive dehalogenases that are present in some anaerobic microorganisms (Bouwer et al., (1983) *Appl. Environ. Microbiol.* 45: 1286-1294; DiStefano et al., (1991) *Appl. Environ. Microbiol.* 57: 2287-2292). Of particular importance are organohalogen-respiring bacteria, such as *Dehalococcoides* or *Dehalogenimonas* sp., because reductive dehalogenation is the only known mode of metabolic energy conservation in these microorganisms, and each group can carry up to 36 different non-redundant rdh genes (Seshadri et al., (2005) *Science* 307: 105-108; McMurdie et al., (2009) *PLoS Genet.* 5, e1000714; Moe et al., (2009) *Int. J. Syst. Evol. Microbiol.* 59: 2692-2697).

While organohalogen-respiring bacteria have been key for decontaminating polluted sites via biostimulation and bioaugmentation (bioremediation), there are many instances where such treatments have been hindered by the absence of key microorganisms and genes, enzymatic inhibition, hydrological complications, or incomplete management of microbial competition and associated biogeochemistry. Remediation of common groundwater contaminants such as tetrachloroethene (PCE), trichloroethene (TCE), 1,1,2-trichloroethane (1,1,2-TCA), and 1,2-dichloroethane (1,2-DCA) poses additional challenges since an appropriate assemblage of organohalogen-respiring bacteria, plus their supporting microbial communities, is required for complete dechlorination of these compounds to a harmless end product. Furthermore, it is unclear whether faithful representatives of the well-studied laboratory isolates are dominant organohalogen-respiring bacteria in sediments and groundwater, and to what extent their laboratory-studied phenotypes are relevant in the field.

Given this uncertainty, managing bioremediation of CAHs requires (i) gauging the structure of the microbial community, in particular the organohalogen-respiring bacteria; and (ii) being able to identify and differentiate between closely related but functionally distinct subpopulations. Such information is crucial for predicting and controlling the ecological responses of the microbial communities to natural or engineered perturbations during bioremediation. To be useful for both lab and field applications, any such molecular diagnostic for comprehensively quantifying organohalogen-respiring microorganisms and their complex rdh gene inventories should be simple, cost-effective, and require the minimum possible biological input material (Ziv-El et al., (2012) *Biotechnol. Bioeng.* 109: 2200-2210; Maphosa et al., (2010) *Trends Biotechnol.* 28: 308-316).

Metagenomics (Hug et al., (2012) *BMC Genomics* 13, 327), transcriptomics (Lee et al., (2012) *Appl. Environ. Microbiol.* 78: 1424-1436), proteomics (Rowe et al., (2012) *Environ. Sci. & Technol.* 46: 9388-9397), pan-genome-microarrays (Hug et al., (2011) *Appl. Environ. Microbiol.* 77, 5361-5369; Men et al., (2013) *Appl. Microbiol. Biotechnol.* 97: 6439-6450) and functional-gene tiling microarrays (Marshall et al., (2012) *ISME J.* 6: 814-826; Marshall et al., (2014) *FEMS Microbiol Ecol.* 86: 428-440) have been used to study the eco-physiology of organohalogen-respiring bacteria. However, these approaches have not been widely applied as tools in full-scale field studies due to the requirement of large amounts of DNA as input, bioinformatic complexity, cost constraints, and inadequate sensitivity of the assay primer pairs for detecting low-abundance genes in complex genomic backgrounds. A number of single quantitative PCR (qPCR) assay primer pairs targeting a few of the best understood rdh genes have been shown capable of overcoming these obstacles and are employed regularly in the remediation industry.

SUMMARY

Combinations of reductive dehalogenase (rdh) genes are a distinguishing genomic feature of closely-related organohalogen-respiring bacteria. This feature can be used to deconvolute the population structure of organohalogen-respiring bacteria in complex environments and to identify relevant subpopulations, which is important for tracking interspecies dynamics needed for successful site remediation. The present disclosure encompasses embodiments of a nanoliter qPCR platform to identify organohalogen-respiring bacteria by quantitatively identifying major orthologous reductive dehalogenase gene groups.

One aspect of the disclosure encompasses embodiments of a method for identifying a dechlorinating microbial organism, or a plurality of said microbial organisms, in a sample comprising: (a) obtaining a sample suspected of having a population of at least one microbial strain having at least one species of a reductive dehalogenase enzyme; (b) isolating nucleic acid from the sample; (c) applying the isolated nucleic acid to a microfluidic device configured for quantitative real-time PCR and comprising a panel of reductive dehalogenase (rdh)-specific PCR primer pairs, wherein each primer pair of the panel is selected to allow amplification of a specific target nucleotide sequence under a common PCR protocol; (d) simultaneously performing quantitative real-time PCR on the isolated nucleic acid in the microfluidic device with each rdh-specific PCR primer pair of said panel and under conditions wherein the presence of a microbial reductive dehalogenase (rdh)-related nucleic acid sequence results in at least one detectable amplicon encoding a region of a reductive dehalogenase (rdh); (e) detecting the at least one amplicon of step (d); (f) identifying the reductive dehalogenase enzyme encoded by the at least one amplicon; and (g) identifying the microbial strain or strains in the sample of step (a) that has at least one reductive dehalogenase enzyme.

In embodiments of this aspect of the disclosure, the method can further comprise the step of quantitatively determining the population(s) of microbial strains in the sample of step (a) that have a reductive dehalogenase enzyme.

In embodiments of this aspect of the disclosure, the method can further comprise the step of classifying the identified reductive dehalogenase enzyme(s) encoded by the at least one amplified PCR product according to their respective reductive dehalogenase (rdh) orthologous groups.

Another aspect of the disclosure encompasses embodiments of a microfluidic nanoliter-quantitative PCR device configured for quantitative real-time PCR and comprising a panel of reductive dehalogenase (rdh)-specific PCR primer pairs.

BRIEF DESCRIPTION OF THE DRAWINGS

Many aspects of the disclosure can be better understood with reference to the following drawings.

FIGS. 2A-2C are graphs illustrating 1,2-dichloroethane concentrations in replicate pore waters. Pore-water samples from wells BPR011, PC008, and PC031 amended with 2 mM mineral salt control (∇), sodium-lactate (X), sodium-formate (+), or sodium-acetate (♦).

FIG. 2D illustrates the measured abundance of 16S rRNA gene, hupL and reductive dehalogenase orthologue groups (RD-OG). In some cases, roughly stoichiometric increases between a 16S marker genes and RD-OG estimates suggest a potential linkage between genes to a specific genus.

FIG. 3A illustrates the hierarchical clustering of RD-OG and rdh based on time-series correlation.

FIG. 3B illustrates the median gene counts for each RD-OG and rdh at each sampled time point. Lines represent unique RD-OG, rdh, or hupL sequence types, with colors indicating assignment to a hypothesized strain based on hierarchical clustering. Unique shapes in the figure legend emphasize hupL types and biochemically characterized RD-OG.

FIGS. 4A and 4B illustrate reductive dehalogenase nl-qPCR suite validation.

FIG. 4A illustrates a network displaying sequences in Dehalogenase Pfam PF13486 v26.0 as nodes. Edges represent pairwise percent identity greater than 90% spanning at least half the length of the shorter sequence.

FIG. 4B illustrates accuracy and quantitative estimates achieved when amplifying rdh genes from four isolates representing the three major *Dehalococcoides mccartyi* subgroups: Victoria (VS), Cornell (195), and Pinellas (CBDB1, GT). Classification of results as true positive (TP), true negative (TN), false positive (FP), and false negative (FN) were based on the majority result for all assays associated with each target group.

DETAILED DESCRIPTION

Figure 1:
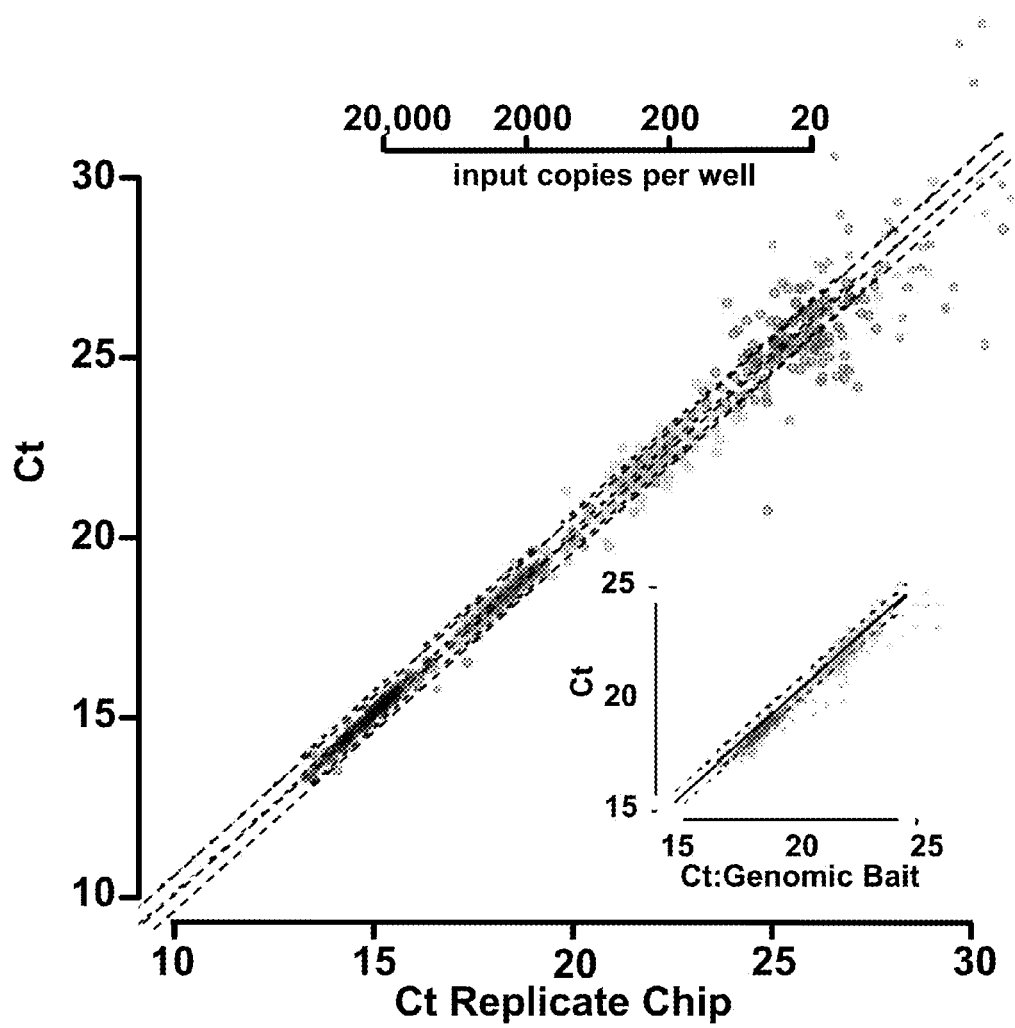
FIG. 1 is a graph illustrating the assay calibration results across two chips with DNA standards applied in a ten-fold dilution series show sensitivity of the assays. Proximity to the 45-degree line reflects replicability across duplicate chips. The addition of genomic bait from 8 non-organohalogen respiring bacteria at 10 to 100 times the copy ratio of the target did not cause a loss of sensitivity.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations

CAH, Chlorinated Aliphatic Hydrocarbon; hupL, gene name abbreviation for nickel-containing uptake hydrogenase; NCBI, National Center for Biotechnology Information; HRB, Organohalogen-Respiring Bacteria; PCR, Polymerase Chain Reaction; PID, Percent Pairwise Identity between aligned sequences; Rdh, reductive dehalogenase enzyme; rdh, reductive dehalogenase gene; RD-OG, Reductive Dehalogenase Orthologue Group; 16S rRNA, 16S small subunit ribosomal ribonucleic acid Definitions In describing and claiming the disclosed subject matter, the following terminology will be used in accordance with the definitions set forth below.

The term "sample" as used herein refers to any water-based sample that may be obtained from an environmental source including, but not limited to, rivers, pools, drainage, sewage, standing puddles, industrial effluent, and the like. A sample may further refer to a water-based extract derived from a solid such as soil.

The term "isolating nucleic acid from a sample" as used herein refers to any method known to one of skill in the art that results in an aqueous solution of microbial nucleic acid. for example, but not intended to be limiting, the microbial population of a collected sample may be concentrated by centrifugation or filtration, the microbial organisms may be resuspended in a suitable aqueous medium, lysed by such as sonication or enzyme, the nucleic acid precipitated by ethanol, dried and resuspended in an aqueous medium for application to a microfluidic device of the disclosure. It is contemplated that the nucleic acid of a microbial population is so isolated that each reaction chamber of the microfluidic device receives an identical aliquot of the isolated nucleic acid, thereby allowing comparisons between the amounts amplification products of each chamber.

The term "common PCR protocol" as used herein refers to each reaction site of a microfluidic device according to the disclosure being exposed to the same PCR conditions of buffer, nucleotide concentrations, enzyme amounts, etc. to allow comparisons between the amounts of the amplification products of each chamber.

The term "orthologs" as used herein refers to genes in different species that evolved from a common ancestral gene by specification. Normally, orthologs retain the same function in the course of evolution.

The terms "digital PCR" and "quantitative PCR (qPCR)" as used herein refer to a method of quantifying the amount of specific nucleic acids in a sample by counting amplification from a number of single molecules. Digital PCR (polymerase chain reaction) is achieved by capturing or isolating each individual nucleic acid molecule present in a sample within many separate chambers, zones or regions that are able to localize and concentrate the amplification product to detectable levels. After PCR amplification, a count of chambers, zones or regions containing PCR end product is a direct measure of the absolute nucleic acids quantity.

The term "microfluidic digital PCR" as used herein refers to a method of digital (quantitative) PCR that uses a microfluidic system. A microfluidic system comprises a number of fluidic elements, such as passages, chambers, conduit, valves, etc. configured to carry out or permit fluid handling and treatment operations, such as introduction of reagents, heating, cooling, etc. The system will generally have an internal cross-sectional dimension, e.g., depth or width, of between about 10 nm and 500 µm. Microfluidic digital PCR devices can typically include a number of microscale channels, and preferably from at least 50 to the order of hundreds of separate reaction chambers for individual PCR reactions to be carried out in parallel. The body structure of the microfluidic device may comprise a single component, or an aggregation of separate parts, e.g., capillaries, joints, chambers, layers, etc., which when appropriately mated or joined together, form the microfluidic device. It is contemplated that any microfluidic device known to one of skill in the art that allows the simultaneous PCR detection of the amplicon products using the primer pairs of the disclosure under a common PCR protocol may be suitably adapted for use in the methods herein disclosed.

Microfluidic devices advantageous for use in the methods of the disclosure can comprise, but are not limited to, a top portion, a bottom portion, and an interior portion, wherein the interior portion substantially defines the channels and chambers of the device. The bottom portion can comprise a solid substrate that is substantially planar in structure, and which has at least one substantially flat upper surface, although one or more of these surfaces is generally provided with valve and other deformable structures. A variety of substrate materials may be employed. The substrate materials will generally be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and other reaction conditions needed for the amplification of a single nucleic acid. In some embodiments, the substrate material may include materials normally associated with the semiconductor industry in which such microfabrication techniques are regularly employed, including, e.g., silica based substrates such as glass, quartz, silicon or polysilicon, as well as other substrate materials, such as gallium arsenide and the like. In the case of semiconductive materials, it will often be advantageous to provide an insulating coating or layer, e.g., silicon oxide, over the substrate material. Details on the construction of suitable microfluidic device for use in the methods of the disclosure, while not intending to be limiting, may be found, for example, in U.S. Pat. No. 6,899,137, U.S. Pat. No. 6,911,345, U.S. Pat. No. 7,118,910, and U.S. Pat. No. 7,833,709.

The term "quantitative real-Time PCR" as used herein, used interchangeably with the term "quantitative PCR" (abbreviated "qPCR"), refers to a method for simultaneous amplification, detection, and quantification of a target polynucleotide using double dye-labeled fluorogenic oligodeoxyribonucleotide probes during PCR and includes such methods as TaqMan, SYBR Green assays, and the like.

The term "propene" as used herein refers to $H_2C=CH—CH_3$.

The term "1,2-dichloropropane" as used herein refers to $CH_3—ClCH—CH_2Cl$.

The term "reductive dechlorination" as used herein refers to a subset of dehalorespiration. Reductive dechlorination refers to the process in which a chloro-organic compound as terminal electron acceptor and a chloride atom is removed from a chloro-organic compound. "Dehalorespiration" is a process whereby an organism uses a halo-organic compound as an electron acceptor for energy and growth. More specifically, hydrogen is used as the electron donor, the halo-organic compound is the electron acceptor, and hydrogen halide (i.e., HBr, HCl or HF) is produced. Several anaerobic bacteria are able to reductively dechlorinate chlorinated hydrocarbons and to gain energy from this dehalorespiration process.

The term "reductive dehalogenase" (abbreviated as "rdh") as used herein refers to an enzyme system that is capable of dehalogenating a halogenated straight chain (aliphatic)—or ring (aromatic or cycloaliphatic)—containing organic compound that contains at least one halogen atom. Examples of halogenated organic compounds that may be dehalogenated by a reductive dehalogenase include, but are not limited to, 1,2-dichloropropane, perchloroethylene ($Cl_2C=CCl_2$), trichloroethylene ($Cl_2C=CH—Cl$), dichloroethylene ($Cl—HC=CH—Cl$) and vinyl chloride ($H_2C=CH—Cl$).

The term "dechlorinating bacteria" refers to a bacterial species or organism population that has the ability to remove at least one chlorine atom from a chlorinated organic compound. Examples of dechlorinating bacteria include, but are not limited to, strains of *Dehalococcoides mccartyi*, *Dehalogenimonas lycanthroporepellens*, *Dehalobacter restrictus*, *Sulfurospirillum multivorans*, *Desulfitobacterium dehalogenans*, *Geobacter lovleyi*, *Desulfuromonas chloroethenica*, and *Desulfuromonas michiganensis*. The methods and compositions of the disclosure are most advantageously applied to members of the *Dehalococcoides*, *Dehalogenimonas*, and *Dehalobacter* genera, and most advantageously to the *Dehalococcoides* genus.

The term "sequence similarity" as used herein refers to the extent to which nucleotide or protein sequences are related. The extent of similarity between two sequences can be based on percent sequence identity and/or conservation. With regard to proteins, "sequence identity" is a comparison of exact amino acid matches, whereas sequence similarity refers to amino acids at a position that have the same physical-chemical properties (i.e. charge, hydrophobicity). Amino acids other than those indicated as conserved may differ in a protein or enzyme so that the percent protein or amino acid sequence similarity between any two proteins of similar function may vary.

With regard to polynucleotides, "sequence identity" is a quantitative comparison of exact nucleotide matches. The sequence identity is at least 80%, at least 85%, at least 90%, at least 95%, at least 97%, and at least 99%, as determined by an alignment scheme.

The term "sequence alignment" as used herein refers to the process of lining up two or more sequences to achieve maximal levels of sequence identity (and, in the case of amino acid sequences, conservation), e.g., for the purpose of assessing the degree of sequence similarity or the degree of sequence identity. Methods for aligning sequences and assessing similarity and/or identity are well known in the art. Such methods include for example, the MEGALIGN software Clustal Method, wherein similarity is based on the MEGALIGN Clustal algorithm, ClustalW and ClustalX (Thompson et al. (1997) *Nucleic Acid Res.* 25: 4876-4882) as well as BLASTN, BLASTP, and FASTA (Pearson et al. (1988) *Proc. Natl. Acad. Sci. USA.* 85: 2444-2448). When using these programs, the preferred settings are those that result in the highest sequence similarity or identity.

The term "primer" as used herein refers to an oligonucleotide complementary to a DNA segment to be amplified or replicated. Typically primers are used in PCR. A primer hybridizes with (or "anneals" to) the template DNA and is used by the polymerase enzyme as the starting point for the replication/amplification process. By "complementary" it is meant that the primer sequence can form a stable hydrogen bond complex with the template.

The term "detectably labeled" as used herein refers to an oligonucleotide labeled with a fluorophore, or other molecular species that elicits a physical or chemical response that can be detected by eye or by an instrument.

The term "fluorophore" as used herein refers to any reporter group whose presence can be detected by its light emitting properties.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the primers of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.,), HiLyte™ Fluors (AnaSpec), and DyLite™ Fluors (Pierce, Inc).

The term "DNA" as used herein refers to the polymeric form of deoxyribonucleotides (adenine, guanine, thymine, or cytosine) in a single or double-stranded state and includes linear or circular DNA molecules. In discussing DNA molecules, sequences may be described by the convention of giving only the sequence in the 5' to 3' direction.

The term "DNA amplification" as used herein refers to any process that increases the number of copies of a specific DNA sequence by enzymatically amplifying the nucleic acid sequence. A variety of processes are known. One of the most commonly used is the polymerase chain reaction (PCR), which is defined and described in later sections below. The PCR process of Mullis is described in U.S. Pat. Nos. 4,683,195 and 4,683,202. PCR involves the use of a thermostable DNA polymerase, known sequences as primers, and heating cycles, which separate the replicating deoxyribonucleic acid (DNA) strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves an enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

The term "amplification product" and "amplicon" as used herein simultaneously refer to portions of nucleic acid fragments that are produced during a primer directed amplification reaction. A typical method of primer directed amplification includes polymerase chain reaction (PCR). In PCR, the replication composition would include for example, nucleotide triphosphates, two primers with appropriate sequences, DNA or RNA polymerase and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.), the contents of which are hereby incorporated by reference herein.

The terms "enzymatically amplify" or "amplify" as used herein refer to DNA amplification. Currently the most common method is the polymerase chain reaction (PCR). Other amplification methods include LCR (ligase chain reaction), strand displacement amplification (SDA); Qβ replicase amplification (QβRA); self-sustained replication (3SR); and NASBA (nucleic acid sequence-based amplification), which can be performed on both RNA and DNA.

The terms "nucleic acid," "nucleic acid sequence," or "oligonucleotide" that also encompass a polynucleotide, refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone.

The term "oligonucleotide" as used herein refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

The term "polymerase" as used herein refers to an enzyme that catalyzes the sequential addition of monomeric units to a polymeric chain. In advantageous embodiments of this disclosure, the "polymerase" will work by adding monomeric units whose identity is determined by a complementary template of a specific sequence. DNA polymerases such as DNA pol 1 and Taq polymerase add deoxyribonucleotides to the 3' end of a polynucleotide chain in a template-dependent manner, thereby synthesizing a complementary nucleic acid. Polymerases may extend a primer once or may repetitively amplify two complementary strands using two primers.

The term "polynucleotide" as used herein refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

DESCRIPTION

PCR Based Detection of Dechlorinating Bacteria:

The oligonucleotides having the sequences SEQ ID NO: 1-336 of the present invention may be used as primers in primer-directed nucleic acid amplification, i.e., PCR or qPCR, to detect the presence of the target gene(s) in dechlorinating wild-type or cultured bacterial strains. Methods of PCR primer design are well known in the art (see, e.g., Sambrook, et al. 2001; Herndon, Va. and Rychlik, W. (1993 In White, B. A. (ed.), Methods in Molecular Biology, Vol. 15, pp 31-39, PCR Protocols: Current Methods and Applications. Humania Press, Inc., Totowa, N.J.; see also, U.S. Pat. Nos. 4,683,195; 4,683,202; 4,965,188; and 4,800,159, which are hereby incorporated by reference). Methods for selecting the oligonucleotides of the present disclosure are herein fully disclosed.

Detection of dechlorinating bacteria, such as *Dehalococcoides* strains including *Dehalococcoides* (Dhc) *mccartyi* strains using PCR involves the amplification of DNA obtained from a sample suspected of having microbial dechlorinating activity. The isolated DNA is amplified using a pair, or pairs, of oligonucleotide primers, wherein one primer (a forward primer) binds to the coding strand of the template and the other primer (a reverse primer) binds to the complementary strand of the template, thus creating two copies of the target region in each PCR cycle. A primer refers to an oligonucleotide that can be extended with a DNA polymerase using monodeoxyribonucleoside triphosphates and a nucleic acid that is used as a template. This primer preferably has a 3' hydroxyl group on an end that is facing the 5' end of the template nucleic acid when it is hybridized with the template.

A set of primers refers to a combination or mixture of at least a first (forward) and a second (reverse) primer. The first primer can be extended using the template nucleic acid while forming an extension product in such a way that the second primer can hybridize with this extension product in a region of the extension product that lies in the 3' direction of the extendable end of the first primer. The extendable end of the second primer points in the 5' direction of the extension product of the first primer. Primer pairs that are suitable for performing the polymerase chain reactions (PCR) and identifying the species or strain of dehalogenating bacteria by the methods of the disclosure are provided in Table 2, wherein odd numbered SEQ ID NO: designations refer to forward primers and even SEQ ID NO: designations refer to reverse primers. Typical amplicons (i.e. the DNA product of a PCR reaction) range in size from 300 by to about 800 base pairs.

The primers of the present disclosure are designed to be specific to regions of the rdh genes identified herein and to allow amplification of rdh-specific sequences under a common PCR condition applied to the microfluidic device used in the analysis. Advantageous primers include, but are not limited to, those having the nucleotide sequence according to SEQ ID NOS: 1-336. Primer pairs suitable for a PCR reaction can be SEQ ID NOs: 1 and 2, 3 and 4, 5 and 6, etc. as disclosed in Table 3.

Quantitative Real-Time PCR Based Enumeration of Dechlorinating Bacteria:

The present disclosure encompasses embodiments of a method of detecting and enumerating dechlorinating bacteria using Quantitative Real-Time PCR ("qPCR"). Quantitative Real-Time PCR allows contemporaneous quantification of a sample of interest, for example a bacteria population having a polynucleotide sequence of interest.

In qPCR, a fluorogenically-labeled oligonucleotide probe can be used in addition to the primer sets which are employed in standard PCR. In qPCR, the probe anneals to a sequence on the target DNA found between a first (forward, 5' primer) and second (reverse, 3' primer) PCR primer binding sites and consists of an oligonucleotide with a 5'-reporter dye (e.g., FAM, 6-carboxyfluorescein) and a quencher dye [e.g., TAMRA, 6-carboxytetramethylrhodamine, black hole quencher (BHQ)] which quenches the emission spectra of the reporter dye as long as both dyes are attached to the probe. The probe signals the formation of PCR amplicons by a process involving the polymerase-induced nucleolytic degradation of the double-labeled fluorogenic probe that anneals to the target template at a site between the two primer recognition sequences (see, e.g., U.S. Pat. No. 6,387,652).

The measurement of the released fluorescent emission following each round of PCR amplification (Heid et al., (1996) *Genome Res.* 6: 986-994) thus forms the basis for quantifying the amount of target nucleic acid present in a sample at the initiation of the PCR reaction. Since the exponential accumulation of the fluorescent signal directly reflects the exponential accumulation of the PCR amplification product, this reaction is monitored in real time. From the output data of the qPCR, quantification from a reliable back calculation to the input target DNA sequence is possible using standard curves generated with known amounts of template DNA.

Quantitative Real-Time PCR may be used to identify and quantify a population of dechlorinating bacteria having a polynucleotide sequence of interest by first isolating DNA from a sample suspected of having dechlorinating activity using any one of the methods known in the art (see e.g., He et al. (2003) *Appl. Environ. Microbiol.* 65: 485-495) or otherwise herein disclosed. The isolated DNA may be amplified using qPCR by contacting the sample with any one of the primer pairs described above. The isolated DNA sample is subjected to qPCR using any one of the qPCR protocols known in the art or as herein disclosed. During the course of PCR the fluorescent signal generated by the reaction may be continuously monitored using detection hardware known in the art.

The amount of dechlorinating bacteria containing the rdh-specific nucleotide sequence of interest and present in the sample may be determined, using qPCR, by comparing the results of the qPCR assay to a calibration curve. A calibration curve (log DNA concentration versus arbitrarily set cycle threshold value, $C_T$) may be obtained using serial dilutions of DNA of known concentration or gene copy numbers. The $C_T$ values obtained for each sample may be compared with the standard curve to determine the abundance of such as *Dehalococcoides* gene targets.

Idiosyncratic combinations of reductive dehalogenase (rdh) genes are a distinguishing genomic feature of closely related organohalogen-respiring bacteria. This feature can be used to deconvolute the population structure of organohalogen-respiring bacteria in complex environments and to identify relevant subpopulations, which is important for tracking interspecies dynamics needed for successful site remediation. The present disclosure encompasses embodiments of a nanoliter qPCR platform to identify organohalogen-respiring bacteria by quantifying major orthologous reductive dehalogenase gene groups. The qPCR assay primer pairs of the disclosure have been selected as particularly advantageous for use at a single annealing temperature and buffer condition and can be operated in parallel within, for example, a 5184-well nl-qPCR chip. A robust bioinformatics approach was developed to select from thousands of computationally-designed primer pairs those that are specific to individual rdh gene groups and compatible with a single PCR assay condition. The most selective qPCR assay primer pairs were validated and their performance examined in two pilot applications: (i) the quantitative analysis of biostimulated aquifer pore water microcosms from a 1,2-dichloroethane-contaminated site and (ii) a trichloroethene-degrading bioreactor. Both revealed sub-population abundance shifts and unexpected community dynamics.

The number of uncharacterized rdh genes continues to expand rapidly (Hug et al., (2013) *Philo. Trans. Roy. Soc. B: Biol. Sci.* 368: 20120322-20120322). More than 690 non-redundant Rdh protein sequences are currently in the NCBI database. Given the constraints of existing molecular tools, a microfluidics-based, massively parallel qPCR approach was explored for targeting known rdh orthologue groups to: quantitatively track sub-populations of organohalide-respiring microorganisms, identify geographically-specific bacterial taxons, and observe interspecies population dynamics. The usefulness of this parallel nl-qPCR platform was demonstrated as a tool for the quantitative analysis of rdh gene repertoires and microbial communities, which collectively dehalogenate CAHs. It has now been shown that (i) with a biostimulated aquifer pore-water from a contaminated site and (ii) with a lab-scale bioreactor that the embodiments of the platform of the disclosure translates well to engineering applications. Quantitative data is achieved economically and rapidly from very modest DNA input quantities without bias introduced by DNA pre-amplification.

Reductive dehalogenases (Rdh) enzymes contain two 4Fe-4S clusters and one corrinoid co-factor per catalytic subunit (Müller et al., (2004) *Appl. Environ. Microbiol.* 70: 4880-4888). Rdhs are identified by the presence of amino acid sequence motifs for binding these cofactors as well as by pairwise amino acid sequence identity to biochemically characterized Rdh enzymes. A sequence-identity-based naming system for Rdhs exists wherein the protein family is divided into orthologue groups (Hug et al., (2013) *Philo. Trans. Roy. Soc. B: Biol. Sci.* 368: 20120322-20120322). 'Reductive Dehalogenase Orthologue Groups' (RD-OGs) are sets of two or more distinct Rdh sequences where all members share at least 90% amino acid identity with another member. RD-OG membership is limited to sequences in known microorganisms. RD-OG sequence similarity does not guarantee shared substrate specificity, however, and members of distinct orthologue groups can have a biochemical activity for a common substrate.

A suite of novel qPCR primers was designed as suitable for the detection of, and distinguishing between, different orthologue groups of reductive dehalogenase (rdh) genes in the Dehalogenase protein family (Pfam) PF13486 (Hug et al., (2013) *Philo. Trans. Roy. Soc. B: Biol. Sci.* 368: 20120322-20120322). The Pfam database included sequences obtained from both microbial isolates and environmental samples, which were incorporated into the RD-OG framework. Because qPCR primers cannot accommodate degenerate base positions, it was sometimes found necessary to rely on multiple primer sets to encompass an RD-OG.

Assay primer pairs were initially designed for the detection of 54 primary rdh references sequences, where each assay was complementary to at least two additional sequences sharing high percentage pairwise identity (>90%) to the reference. A computational pipeline for the automated primer selection was developed because nl-qPCR requires running PCR reactions with many distinct primer pairs at a single stringent annealing temperature and buffer composition. Unique assay primer pairs were further designed for those rdh genes in *Dehalococcoides mccartyi* sp. that are not assigned to an orthologue group but have been identified by previous tiling-microarrays.[21] The computational pipeline also enabled the design of primers that could differentiate among three closely-related nucleotide sequence types of the important HupL uptake hydrogenase (hupL) in *Dehalococcoides mccartyi* sp. Assay Specificity: Given high sequence similarity among rdh homologues (Hug et al., (2013) *Philo. Trans. Roy. Soc. B: Biol. Sci.* 368: 20120322-20120322) it was necessary to test whether the candidate assay primer pairs were specific to their intended target. This specificity was predicted via a bioinformatics search for conserved nucleic acid signatures that were distinguishable among groups of closely-related rdh genes.

Experimentally, assay primer pair specificity were tested in two ways. First, assay primer pair specificity was tested by attempting to amplify dilute linear rdh gene standards in the presence of a concentrated mixture of total genomic DNA isolated from eight non-target anaerobic archaea and bacteria. Genes for rdh are absent in these eight anaerobic microorganisms, but these microbes contain iron-sulfur-cluster and corrinoid-containing enzymes that share motifs similar to regions conserved in Rdh proteins. Second, assay primer pairs were tested against four distinct *Dehalococcoides mccartyi* cultures for which there was a priori knowledge of their rdh and hupL gene composition. DNA from *Dehalococcoides* strains isolated from contaminated and wastewater treatment sites was used: VS (Victoria, Tex., USA), *ethenogenes* 195 (Ithaca, N.Y.), GT (Cottage Grove, Wis., USA), and CBDB1 (Jena, Germany). The isolates (Seshadri et al., (2005) *Science* 307: 105-108; McMurdie et al., (2009) *PLoS Genet.* 5, e1000714; Kube et al., (2005) *Nat Biotechnol.* 23: 1269-1273) represent all three known *Dehalococcoides* subgroups as defined by 16S rRNA differences: Cornell, Victoria, and Pinellas (Hendrickson et al., (2002) *Appl. Environ. Microbiol.* 68: 485-495).

Amplification was observed across target DNA concentrations ranging from 25 pg to 0.1 pg per 100 nL reaction. The assay primer pairs were sensitive at the lowest target-DNA inputs tested. In the presence of more concentrated non-target genomic DNA (50 pg per well) from 8 non-organohalogen-respiring anaerobic bacteria, selectivity and sensitivity remained.

Figure 4A:
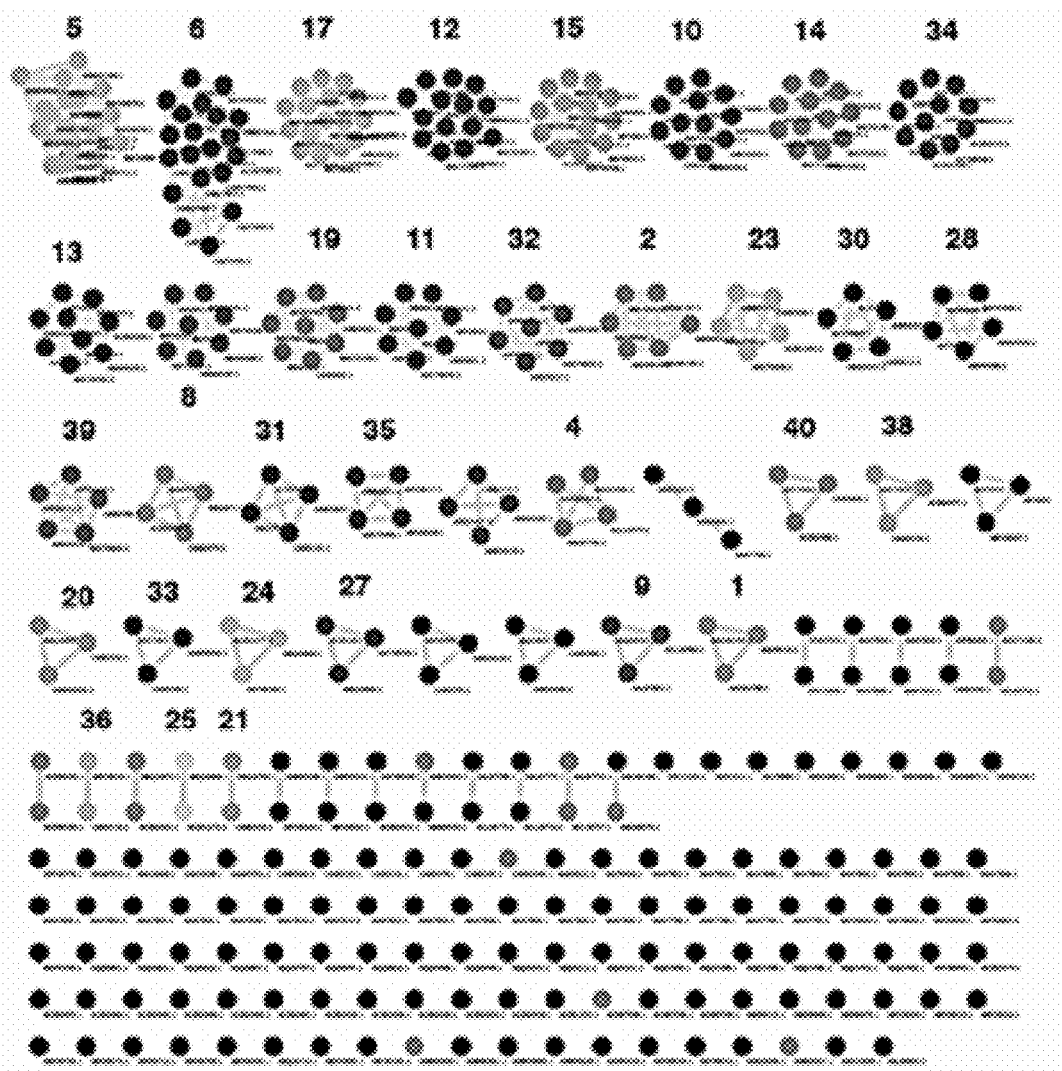
Figure 4B:
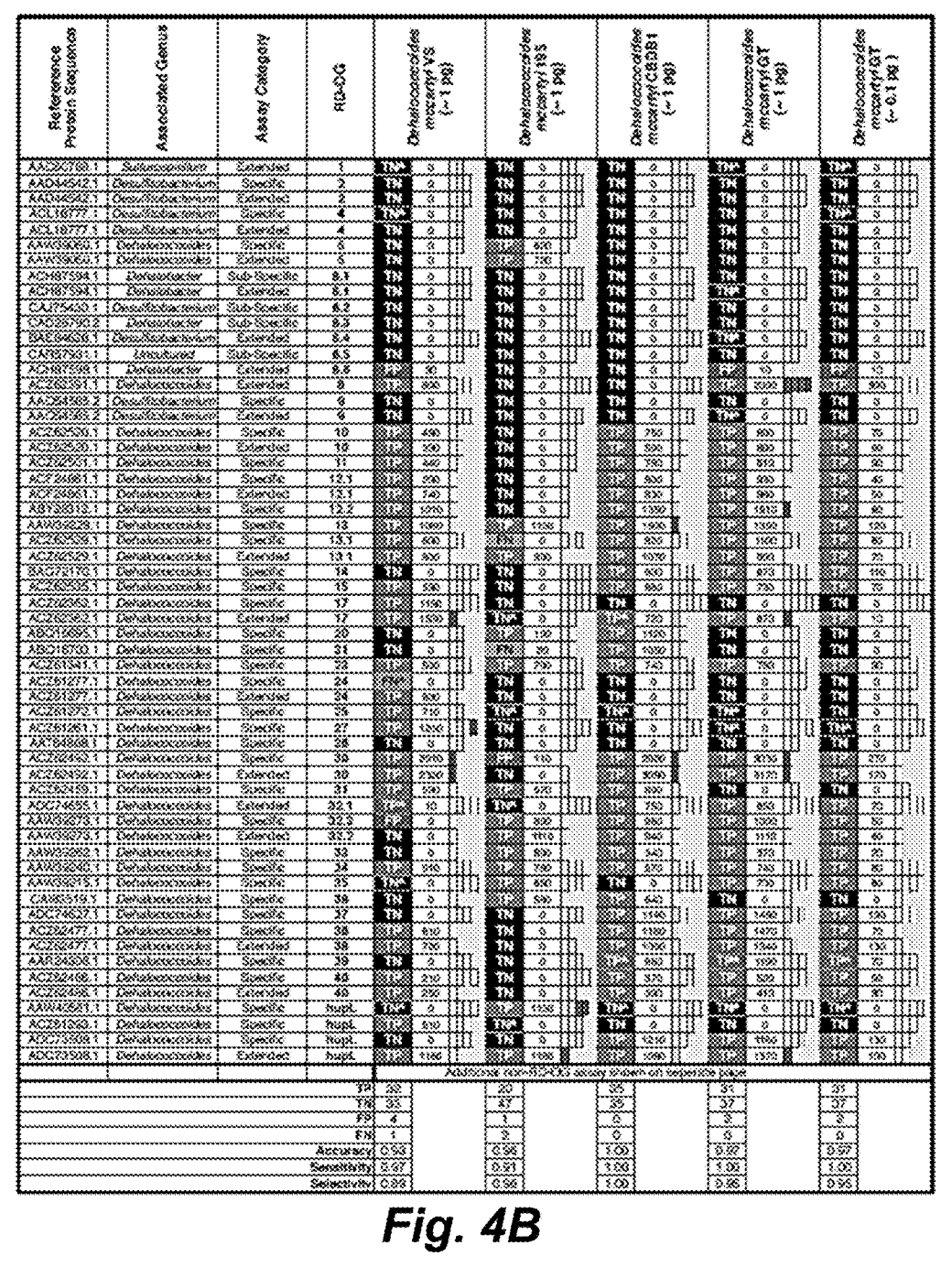
Figure 4B:
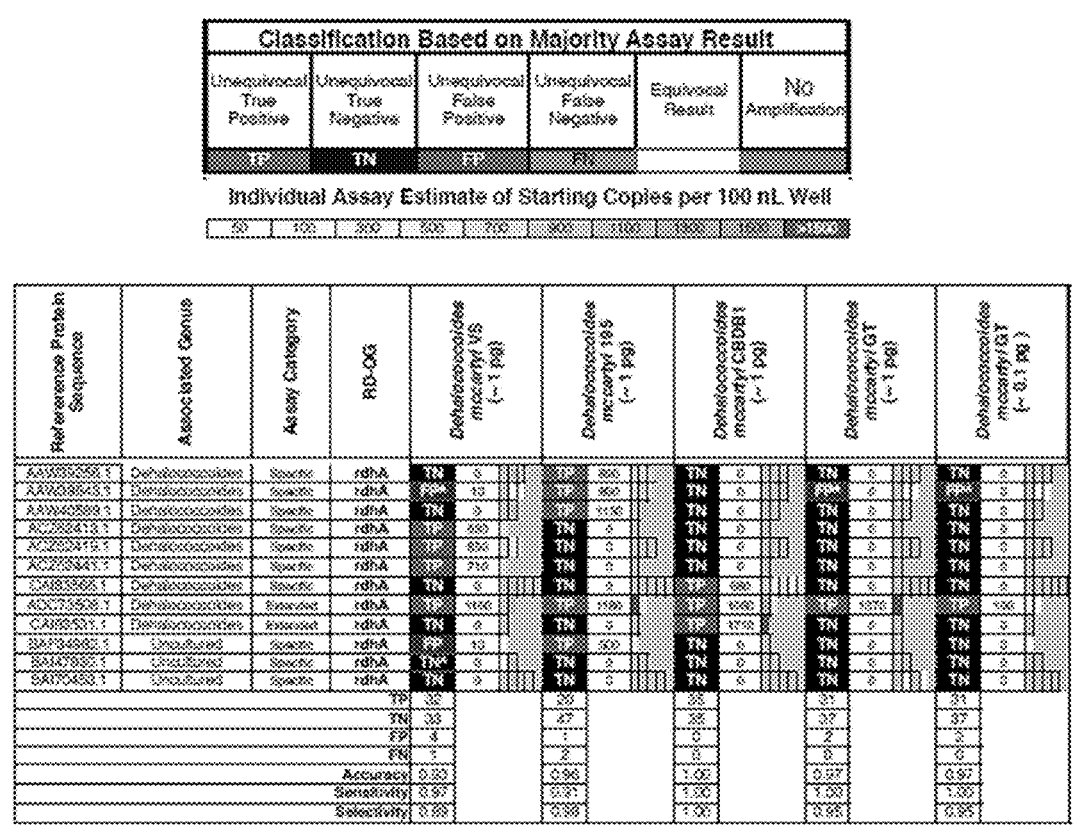

For PCR assay primer pairs selected to be included in the final nl-qPCR platform, each assay had to (i) amplify its target with a PCR efficiency greater than 85% (most were >90%), (ii) not amplify negative control DNA prior to thermal cycle 28, and (iii) not exhibit self-dimerization as evidenced by a melt curve analysis. Of 600 candidate rdh assay primer pairs tested, 168 fulfilled these criteria, and absence/presence classification was >93% accurate against the four *Dehalococcoides* isolates tested (as shown in FIG. 4B).

False-positive amplification could arise from permissive primer binding conditions. There were instances in which an individual assay produced a false-positive result, usually manifested as a delayed amplification for an orthologue group not expected in a given *Dehalococcoides* isolate. The resulting gene count estimates were 2 to 3 orders of magnitude lower than the gene count estimates for the true-positives, suggesting that partial complementarity between primer and non-target sequences carries the risk of producing a delayed Ct. A delayed amplification could not be distinguished as a false positive by the slope of the amplification curve alone; however, the partial redundancy we designed in the form of multiple assay primer pairs targeting different nucleotide positions on each target reference rdh sequence allowed us to improve detection accuracy.

Across the isolates tested, 15 of the 168 assay primer pairs produced delayed Ct false positive results. In 66% of these cases, the other assay primer pairs for the same target sequence yielded a correct negative result. FIG. 4B reveals these individual false-positive events, as well as the majority result from multiple assay primer pairs to improve the classification of true negatives vs. false positives at the target level. Absence/presence classification accuracy on the target is recorded rather than the individual assay level.

Assay primer pairs for every known RD-OG were not developed but it is contemplated that the primer selection method may be usefully employed to similarly identify new and useful primers for incorporation into the microfluidic devices of the disclosure for the quantitative detection of other bacterial strains later identified. Space on the nl-qPCR chip was selected for those assay primer pairs with support from three or more unique sequences in the database. For some orthologue groups, none of the candidate assay primer pairs passed all the above-mentioned quality control requirements and thus were not included. One particularly useful assay suite, while not intended to be limiting, encompassed 30 orthologue groups, 12 reductive dehalogenase types not-yet assigned an orthologue group, and 3 hydrogenase gene types found in *Dehalococcoides mccartyi*. It is, however, contemplated that other primer pairs may be devised and selected by the methods of the disclosure to detect rdh gene variants as and when identified. To those assay primer pairs developed here, were added four 16S rRNA marker gene assay primer pairs developed in previous studies[32-34] that tested compatible with our nl-qPCR reaction conditions.

Sensitivity:

The sensitivities of the qPCR assay primer pairs were tested against linear DNA standards in ten-fold dilution series. FIG. 1 shows the technical replicates across two separate chips at four dilutions, spanning approximately 20,000, 2,000, 200, and 20 linear gene copies per 100 nl-reaction volume. Proximity to the 45-degree line reflects replicability across chips. The dynamic range of most nl-qPCR assay primer pairs spanned over six orders of magnitude, as has been shown in another study of the technology (Morrison et al., (2006) *Nucl. Acids Res.* 34: e123-e123).

Figure 5:
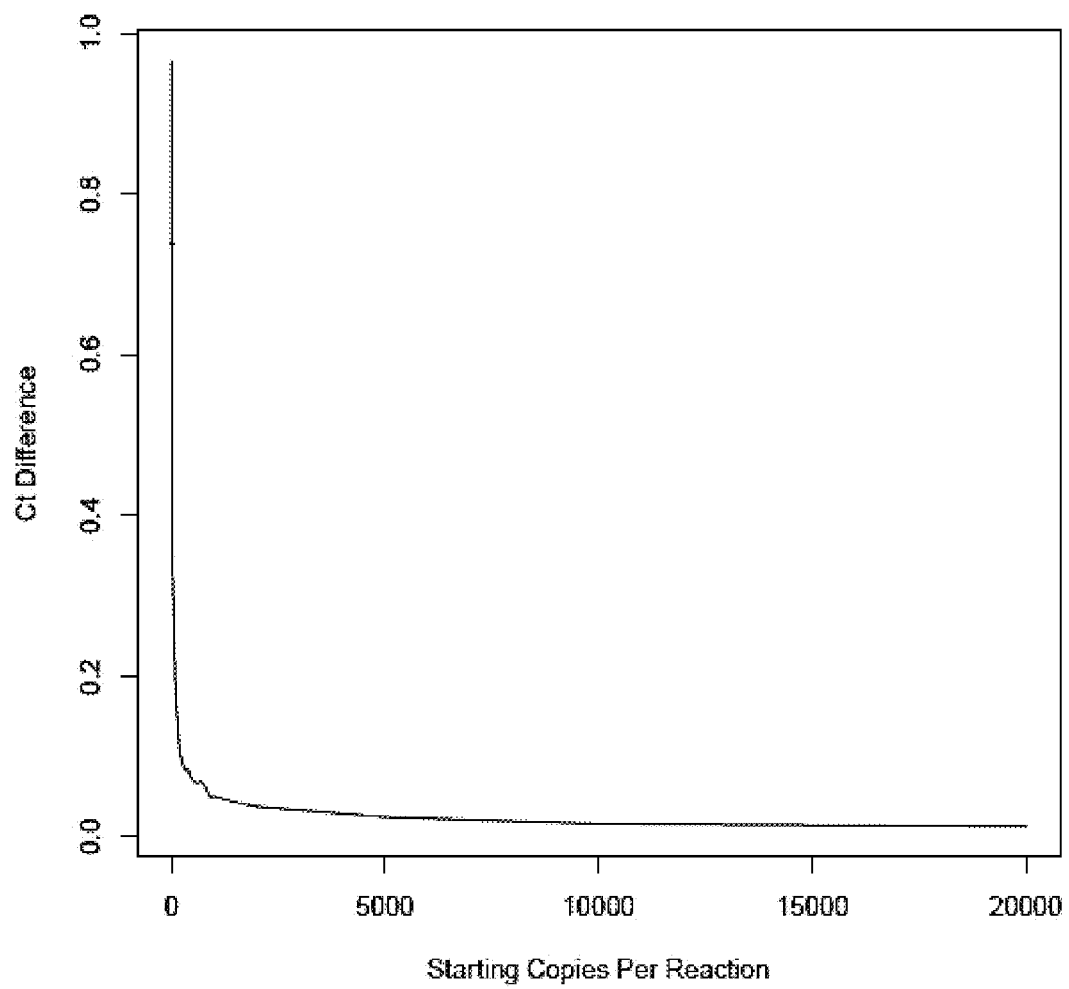
FIG. 5 is a graph illustrating the Ct difference between technical duplicates. Solid points are mean Ct difference between technical duplicates at 20, 200, 2000, and 20000 starting copies (n=116). Solid line shows the expected difference due to Poisson noise.
Figure 6:
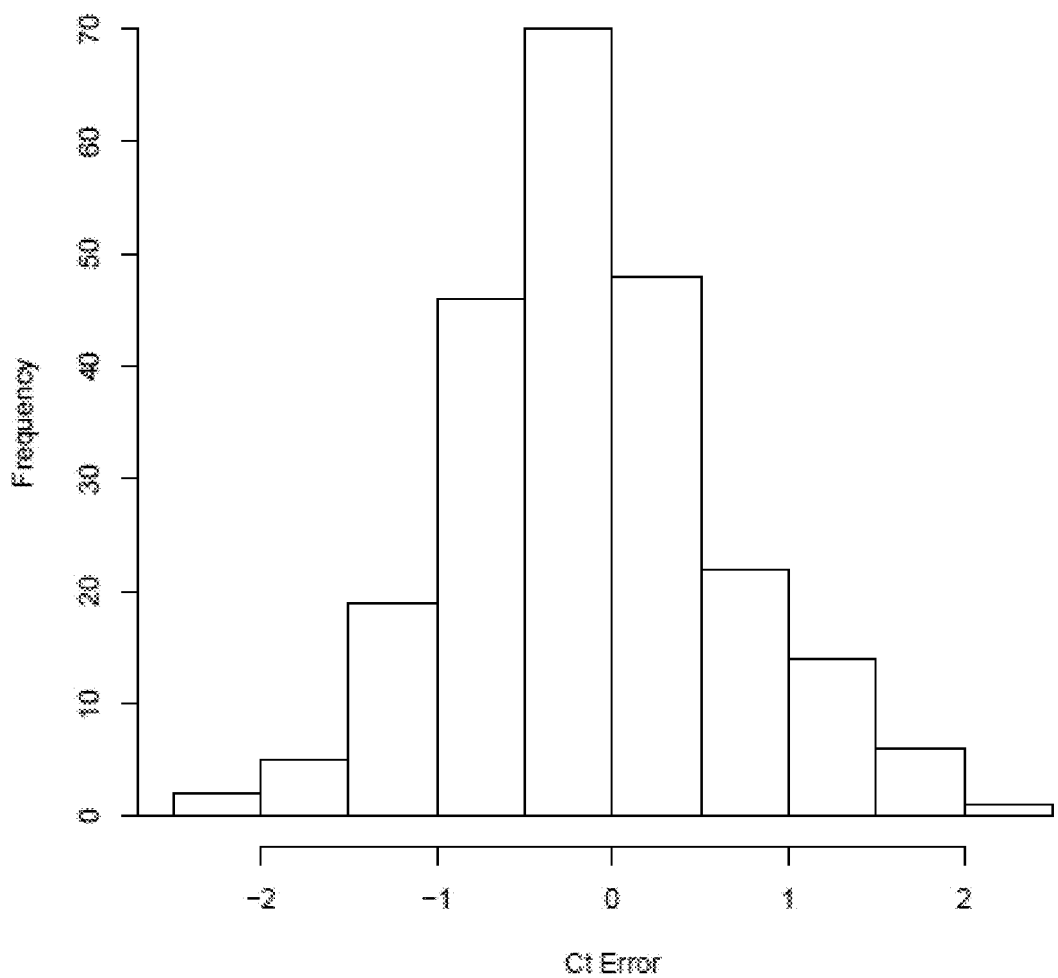
FIG. 6 is a histogram of the Ct errors between the observed result at 20 copies per reaction and the predicted Ct by linear regression from a 3-point calibration curve. A strong bias in the errors was not seen.

The sensitivity of the assay primer pairs of the disclosure against low starting gene copy numbers likely to be found in mixed microbial populations were tested. When the assay primer pairs were calibrated against DNA standards, the amplification Ct values were reproducible across duplicate chips at 20,000, 2000 and 200 starting copies per reaction. At higher dilution, the technical variability increased, and at 20 copies per reaction the mean absolute Ct difference between cross-chip replicate samples was 0.73, compared to 0.33, 0.16, and 0.13 at the respective higher concentrations (FIG. 1). The statistically unbiased nature of the errors, as well as results from counting simulations, indicated that an increased Ct difference at low copy numbers was to be expected, as shown in FIGS. 5 and 6.

Accuracy:

Typically, a single qPCR assay can be used to estimate the abundance of a target gene. Despite strong technical reproducibility, such estimates are not necessarily accurate in environmental samples when an unanticipated mismatch between target and primers causes systematic and reproducible shifts in measured Ct. With the large number of parallel reaction wells available to the nl-qPCR approach, it is possible to estimate the abundance of a target gene based on the combined results of multiple unique assays. While the measurement variability from such an approach will be greater than that for an estimate based on a single set of primers, it is a potentially more robust option for probing previously unsequenced bacterial communities.

This multi-assay-per-target approach was explored with well-characterized samples by examining the mean rdh gene counts in *Dehalococcoides mccartyi*. The median gene count from multiple distinct assay primer pairs targeting the same reference group was calculated. The mean value of these group counts was used to estimate the mean number of rdh copies per sample, which likely had come from a near-clonal *Dehalococcoides mccartyi* population. For example, when DNA from *Dehalococcoides mccartyi* CBDB1 was supplied at 1 pg, 10 pg, and 25 pg per well, the mean estimates—and 95% confidence intervals—of rdh gene abundance were 960+/−200, 9800+/−1800, and 22000+/−4600, respectively. These estimates are consistent with theoretical expectations for single copy genes in an organism with a 1.39 Mb genome (approximately 670 copies per pg DNA).

The range of estimates for individual rdh genes within a single *Dehalococcoides* strains were unexpected, with some estimates greater than double the median estimate possible due to gene duplications, a common evolutionary process in bacteria. Within a near-clonal population, duplicated genes exist in some portion of the population, resulting in total population level DNA that may contain some genes in higher copy numbers than others. In the genome of *Dehalococcoides mccartyi* VS, there are two instances of near identical rdh genes. *Dehalococcoides* cultures are maintained through years of serial transfer, whereupon gene duplication may occur.

Another likely cause for the range of estimates in rdh gene abundance is the lack of perfect complementarity between the primers and intended target sequences. All primers were based on the reference nucleic acid sequences published in the NCBI database, as shown in Table 1.

TABLE 1

NCBI Accession numbers, NCBI Description, Source Organism, and Associated RD-OG of Reference Sequences Used for nL-qPCR Primer Suite Design

| NCBI Protein Accession No. | NCBI Description | Genome | RD-OG |
|---|---|---|---|
| AAC60788.1 | tetrachloroethene reductive dehalogenase catalytically active subunit | *Sulfurospirillum multivorans* | 1 |
| AAD44542.1 | ortho-chlorophenol reductive dehalogenase catalytically active subunit precursor | *Desulfitobacterium dehalogenans* ATCC51507 | 2 |
| ACL18777.1 | reductive dehalogenase | *Desulfitobacterium hafniense* DCB-2 | 4 |
| AAW39060.1 | trichloroethene reductive dehalogenase | *Dehalococcoides mccartyi* 195 | 5 |
| ACH87594.1 | putative 1,2-dichloroethane reductive dehalogenase | *Dehalobacter* sp. WL | 6.1 |
| CAJ75430.1 | dichloroethane reductive dehalogenase | *Desulfitobacterium dichloroeliminans* LMG P-21439 | 6.2 |
| CAD28790.2 | tetrachloroethene reductive dehalogenase | *Dehalobacter restrictus* | 6.3 |
| BAE84628.1 | tetrachloroethene dehalogenase | *Desulfitobacterium hafniense* Y51 | 6.4 |

TABLE 1-continued

NCBI Accession numbers, NCBI Description, Source Organism, and Associated RD-OG of Reference Sequences Used for nL-qPCR Primer Suite Design

| NCBI Protein Accession No. | NCBI Description | Genome | RD-OG |
|---|---|---|---|
| CAR57931.1 | reductive dehalogenase subunit A | uncultured bacterium | 6.5 |
| ACH87598.1 | putative reductive dehalogenase RdhA1 | *Dehalobacter* sp. MS | 6.6 |
| ACZ62391.1 | vinyl chloride reductive dehalogenase | *Dehalococcoides mccartyi* VS | 8 |
| AAQ54585.2 | 3,5-dichlorophenol reductive dehalogenase | *Desulfitobacterium hafniense* | 9 |
| ACZ62520.1 | reductive dehalogenase | *Dehalococcoides mccartyi* VS | 10 |
| ACZ62501.1 | reductive dehalogenase | *Dehalococcoides mccartyi* VS | 11 |
| ACF24861.1 | putative reductive dehalogenase | *Dehalococcoides* sp. MB | 12.1 |
| ABY28312.1 | putative reductive dehalogenase | *Dehalococcoides* sp. enrichment culture clone KS22(KSRdA03) | 12.2 |
| AAW39229.1 | putative reductive dehalogenase | *Dehalococcoides mccartyi* 195 | 13 |
| ACZ62529.1 | reductive dehalogenase | *Dehalococcoides mccartyi* VS | 13.1 |
| BAG72170.1 | reductive dehalogenase homolog | uncultured bacterium | 14 |
| ACZ62535.1 | reductive dehalogenase | *Dehalococcoides mccartyi* VS | 15 |
| ACZ62362.1 | reductive dehalogenase | *Dehalococcoides mccartyi* VS | 17 |
| ACZ62482.1 | reductive dehalogenase | *Dehalococcoides mccartyi* VS | 19 |
| ABQ16695.1 | reductive dehalogenase | *Dehalococcoides mccartyi* BAV1 | 20 |
| ABQ16703.1 | reductive dehalogenase | *Dehalococcoides mccartyi* BAV1 | 21 |
| ACZ61341.1 | reductive dehalogenase | *Dehalococcoides mccartyi* VS | 23 |
| ACZ61277.1 | reductive dehalogenase | *Dehalococcoides mccartyi* VS | 24 |
| ACZ61272.1 | reductive dehalogenase | *Dehalococcoides mccartyi* VS | 25 |
| ACZ61261.1 | reductive dehalogenase | *Dehalococcoides mccartyi* VS | 27 |
| AAT64888.1 | putative vinyl chloride reductive dehalogenase bvcA | *Dehalococcoides mccartyi* BAV1 | 28 |
| ACZ62492.1 | reductive dehalogenase | *Dehalococcoides mccartyi* VS | 30 |
| ACZ62459.1 | reductive dehalogenase | *Dehalococcoides mccartyi* VS | 31 |
| ADC74655.1 | reductive dehalogenase | *Dehalococcoides mccartyi* GT | 32.1 |
| AAW39273.1 | putative reductive dehalogenase | *Dehalococcoides mccartyi* 195 | 32.2 |
| AAW39262.1 | putative reductive dehalogenase | *Dehalococcoides mccartyi* 195 | 33 |
| AAW39240.1 | putative reductive dehalogenase | *Dehalococcoides mccartyi* 195 | 34 |
| AAW39215.1 | putative reductive dehalogenase | *Dehalococcoides mccartyi* 195 | 35 |
| CAI83519.1 | putative reductive dehalogenase | *Dehalococcoides mccartyi* CBDB1 | 36 |
| ADC74627.1 | reductive dehalogenase | *Dehalococcoides mccartyi* GT | 37 |
| ACZ62477.1 | reductive dehalogenase | *Dehalococcoides mccartyi* VS | 38 |
| ACZ62486.1 | putative reductive dehalogenase | *Dehalococcoides mccartyi* VS | 39 |
| AAR24308.1 | reductive dehalogenase homologous protein RdhA7 | *Dehalococcoides mccartyi* CBDB1 | 40 |
| AAT48554.1 | putative reductive dehalogenase | *Dehalococcoides mccartyi* BAV1 | NA |
| AAW39256.1 | putative reductive dehalogenase | *Dehalococcoides mccartyi* 195 | NA |
| AAW39843.1 | putative reductive dehalogenase | *Dehalococcoides mccartyi* 195 | NA |
| AAW40589.1 | putative reductive dehalogenase | *Dehalococcoides mccartyi* 195 | NA |
| ACZ62413.1 | reductive dehalogenase | *Dehalococcoides mccartyi* VS | NA |
| ACZ62419.1 | reductive dehalogenase | *Dehalococcoides mccartyi* VS | NA |
| ACZ62441.1 | reductive dehalogenase | *Dehalococcoides mccartyi* VS | NA |
| ACZ62470.1 | reductive dehalogenase | *Dehalococcoides mccartyi* VS | NA |
| BAF34982.1 | trichloroethene reductive dehalogenase | uncultured *Dehalococcoides* sp. | NA |
| BAI47830.1 | putative reductive dehalogenase | uncultured bacterium | NA |
| BAI70453.1 | reductive dehalogenase | uncultured bacterium | NA |
| CAI83531.1 | putative reductive dehalogenase | *Dehalococcoides mccartyi* CBDB1 | NA |
| CAI83566.1 | putative reductive dehalogenase | *Dehalococcoides mccartyi* CBDB1 | NA |

NA: Sequences not having designated RD-OG

Even for these sequenced isolates, recently accumulated mutations that may be present in the DNA retrieved for this study could produce mismatches that result in systematic downward Ct shifts. The likelihood of Ct shifts increases when primers are applied to previously unsequenced populations. In this context, heightened variability among gene counts can be expected.

Pilot Applications:

After establishing the sensitivity and selectivity of the assay primer pairs in a controlled experimental context, evaluation of performance of the newly established nl-qPCR platform in applications directly relevant to bioremediation was undertaken. Pilot applications were performed to quantitatively (i) evaluate the biostimulation potential of different sections of a contaminated aquifer and (ii) determine sub-population-level responses of dehalogenating microbes to electron donor limitation in a continuously-fed TCE bioreactor.

Biostimulation Potential in a Contaminated Field Site:

In virtually all field environments, hydrological and geochemical conditions are heterogeneous and levels of contaminants vary spatially. For successful in situ bioremediation of CAHs, engineers often need to gauge the potential effectiveness of the remediation technology in different areas of the site that might respond to the intervention according to variable biological and geochemical characteristics. Accordingly, in one study, focusing on three observation wells, 100-500 horizontal meters apart and representative of diverse areas throughout the site, it was endeavored to assess the level of spatial heterogeneity in rdh gene abundance and biochemical potential for the transformation of 1,2-dichloroethane (1,2-DCA).

Several types of organohalogen-respiring bacteria are known to dechlorinate 1,2-DCA. Two distinct dcaA genes have been found to be associated with 1,2-DCA dihaloelimination to ethene in laboratory cultures. Both discovered dcaA genes are members of RD-OG 6, but they share only 88% pairwise identity at the amino acid level by blastp. The first dcaA (hereafter dcaA type I) was identified in *Desulfitobacterium dichloroeliminans* (Marzorati et al., (2007) *Appl. Environ. Microbiol.* 73: 2990-2999; De Wildeman et al., (2003) *Appl. Environ. Microbiol.* 69: 5643-5647). A second type of dcaA (hereafter dceA type II) was found in a *Dehalobacter* sp. (Grostern et al., (2009) *Appl. Environ. Microbiol.* 75: 2684-2693). Certain strains of *Dehalococcoides mccartyi* and *Dehalogenimonas* sp. have also been shown to be capable of growth-linked dechlorination of 1,2-DCA, but the responsible enzymes have not yet been identified. It remains unclear which of these enzymes is most relevant for degrading 1,2-DCA in the field, and under what conditions.

Aquifer pore water contaminated with 1,2-DCA was collected from observation wells at an industrial site in Italy. The microbiology of the site had not been previously characterized. Thus, it was possible to evaluate whether assay primer pairs of the disclosure designed to be complementary to conserved DNA signatures among database sequences would be effective at amplifying genes in an environment where there was no a priori sequence information. Replicate pore water samples from each well were placed in serum vials and amended with 2 mM sodium lactate, sodium formate, sodium acetate, or a mineral salt control.

Figure 2A:
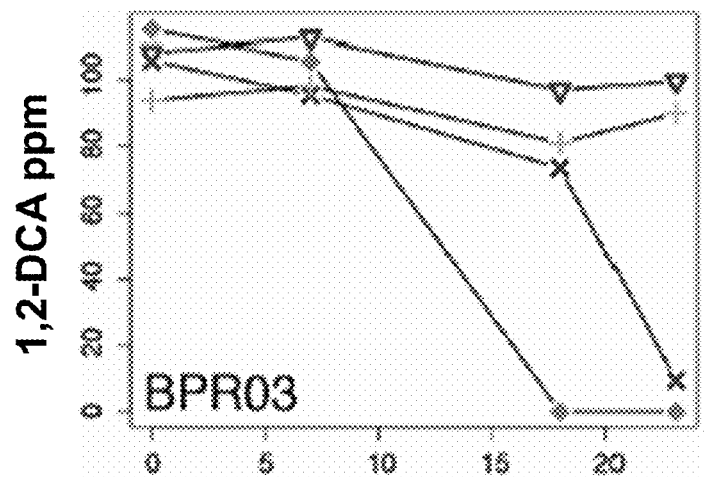
FIGS. 2A-2D are graphs illustrating the heterogeneity in RD-OG composition and biostimulation response in contaminated pore-water.

The quantification of rdh and 16S rRNA marker genes (targeting *Dehalococcoides*, *Geobacter* and *Desulfitobacterium* genera) combined with chemical time-point measurements from the pore water samples revealed a high degree of heterogeneity in biostimulation response and resident OHRB community structure at each sampling well. The effect of the biostimulants on the fate of 1,2-DCA varied and no single biostimulant consistently facilitated dechlorination across all three pore waters (FIG. 2A). The *Geobacter* 16S rRNA gene was detected at all three wells and was abundant in samples from wells BPR03 and PC008, but was less abundant in PC031. The enrichment of *Geobacter* in BPR03 and PC008 pore waters under lactate stimulation occurred in a roughly stoichiometric fashion with the enrichment of a dcaA type I gene. The type II dcaA gene was not detected in the BPR03 nor PC008 pore water, regardless of stimulant condition.

Figure 2B:
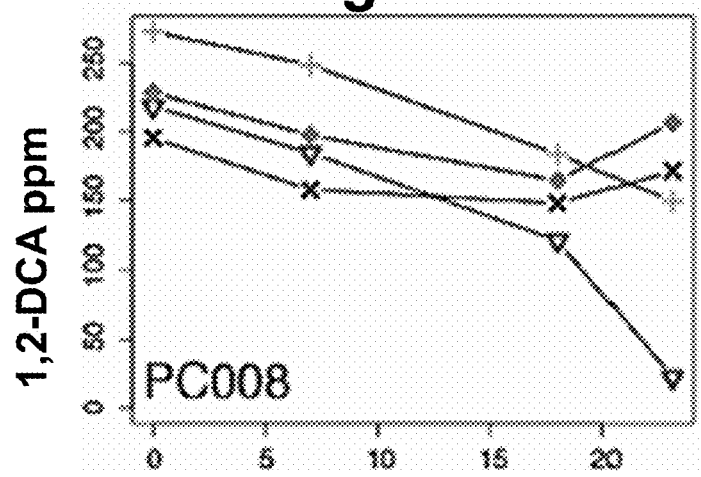
Figure 2C:
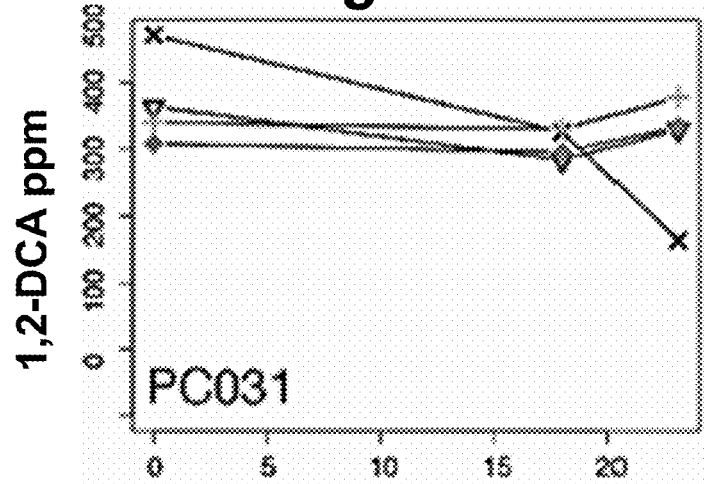
Figure 2D:
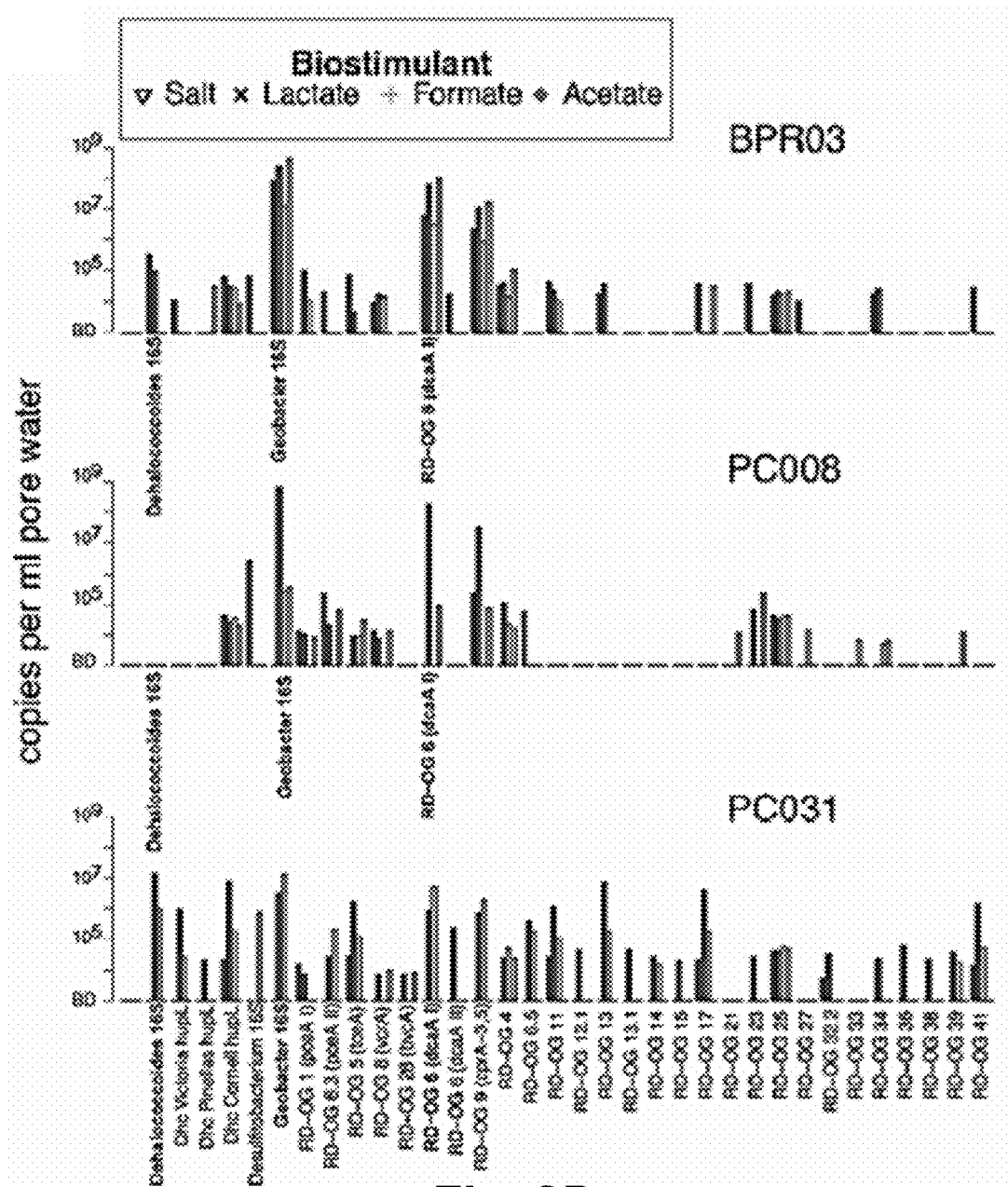

Previous studies of rdh-containing *Geobacter lovleyi* showed the bacterium's capacity for growth-linked dehalogenation of PCE but not for 1,2-DCA (Sung et al., (2006) *Appl. Environ. Microbiol.* 72: 2775-2782). However, the role of *Geobacter* in this environment and the limitations on its activity are not straightforward. Concomitant enrichment of the *Geobacter* 16S rRNA gene and the type I dcaA was neither necessary nor sufficient for 1,2-DCA transformations across all treatments. While 1,2-DCA transformation was observed for lactate amended BPR03 pore water, no similar 1,2-DCA transformation was observed in lactate-amended PC008 pore water, despite equal or greater enrichment of *Geobacter* 16S rRNA and the putative dcaA type I gene (FIG. 2B). It is possible that the enriched well BPR03 *Geobacter* population may contain this type I dcaA gene and is capable of growth with 1,2-DCA as a terminal electron acceptor.

Pore water from well PC031 appeared to have a markedly different organohalogen-respiring community structure than that in either BPR03 or PC008, with *Dehalococcoides* sp. in equivalent or greater abundance than *Geobacter* sp. and *Desulfitobacterium* sp. When stimulated with lactate, a large number of reductive dehalogenase orthologue groups were detected at varying abundances, suggesting the presence of multiple distinct *Dehalococcoides* sub-populations. This is consistent with the significant *Dehalococcoides* sp. diversity found in this area: all three hupL gene groups (Cornell, Victoria, and Pinellas) were detected in both lactate and formate-amended PC031 pore water (as shown in FIG. 2B). The dehalogenation of 1,2-DCA with lactate, but not the formate, suggests that the putative type I dcaA gene enriched in both cases may not be a driver for the observed 1,2-DCA dechlorination.

Determining Composition of Organohalgen-Respiring Bacteria in a Continuous Bioreactor:

In a separate study, the nl-qPCR platform according to the disclosure was used to investigate the effect of electron donor limitation on the population structure of organohalogen-respiring bacteria in a continuous-flow bioreactor inoculated with aquifer material from the Evanite contaminated site in Corvallis, Oreg., USA. The EV2L reactor was operated as a chemostat with influent TCE at 10 mM. After 168 days of the reactor's 5 year operation, the influent formate concentration was reduced from 45 mM to 25 mM.

The high degree of sequence similarity at the 16S rRNA gene level among *Dehalococcoides mccartyi* strains has complicated the tracking of distinct *Dehalococcoides* sub-populations via conventional qPCR or 16S short-amplicon sequencing. However, the relative stoichiometry of different subtypes of *Dehalococcoides* is important for modeling the degradation kinetics and partitioning of TCE, cDCE, and VC electron acceptors among closely related bacterial strains.

Figure 3A:
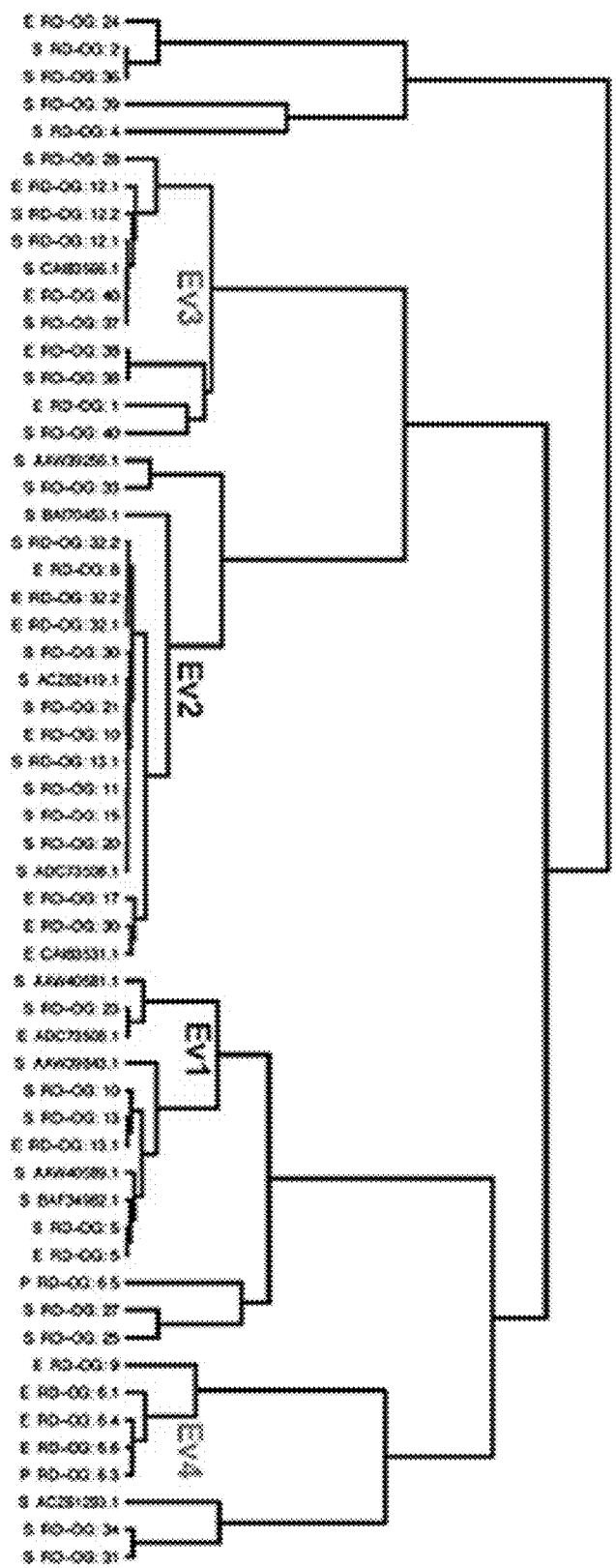
FIGS. 3A and 3B illustrate reductive dehalogenase types detected in a TCE-fed reactor over a 5-year time course.

DNA samples from the reactor's five-year operation were brought to a standard concentration of 10 ng/μl. 20 ng of DNA was applied to duplicate nl-qPCR chips, resulting in a final input of 25 pg of total community DNA per reaction well. The most likely population structure of organohalogen-respiring bacteria in the reactor was inferred using a correlation-based clustering method similar to that described by Marshall et al. Briefly, gene abundance profiles were hierarchically clustered by their time-series correlation, as shown in FIG. 3A. Correlated genes were grouped into clusters representing hypothesized strains if they were at similar absolute abundance.

Figure 3B:
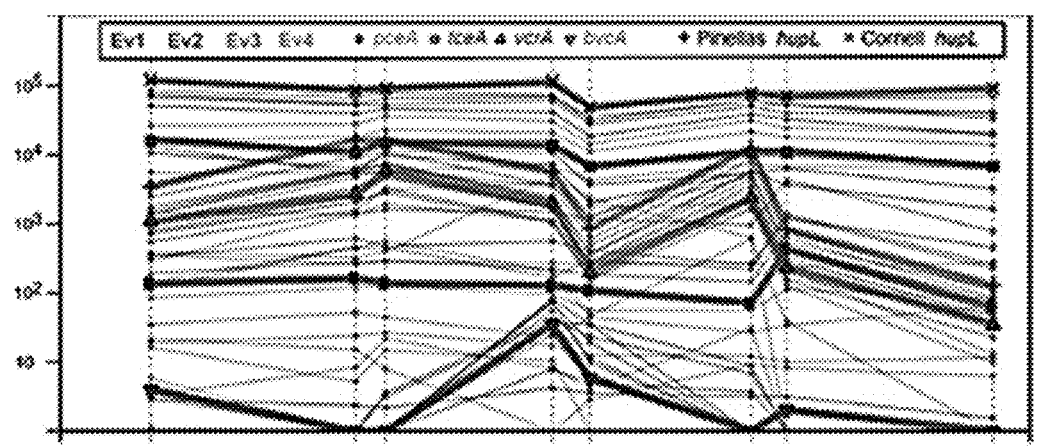

Operationally Identified Strains:

The clustering pattern of rdh and hupL gene counts suggests the presence of at least four distinct organohalogen-respiring sub-populations within the EV2L reactor (FIG. 3A). These operational strains are designated as Ev1, Ev2, Ev3, and Ev4. Throughout the reactor's operation, Ev1 appears to be most numerous (FIG. 3B). Multiple lines of evidence suggested that Ev1 is a *Dehalococcoides*-like-bacterium: Ev1 links at least four orthologue groups (5, 10, 13, and 23), which have so far only been found in *Dehalococcoides* isolates or environmental samples. Group 5 is the best understood, since it contains the characterized trichloroethene reductase tceA first discovered in *Dehalococcoides mccartyi* strain ethenogenes 195 (He et al., (2003) *Nature* 424: 62-65).

Figure 3C:
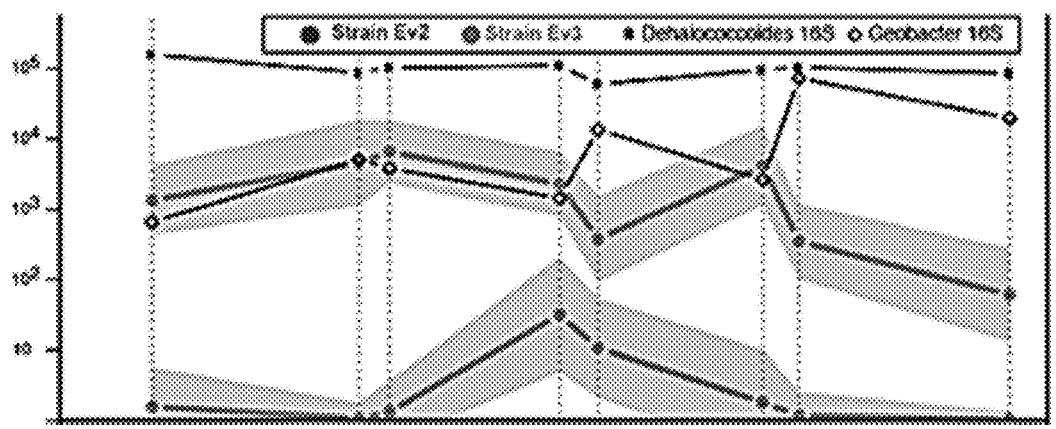
FIG. 3C illustrates 16S level gene count estimates for *Dehalococcoides* and *Geobacter* compared with mean gene abundance estimates of hypothesized vinyl-chloride respiring strains: Ev2 containing vinyl-chloride reductase (vcrA) and Ev3 containing putative vinyl-chloride reductase (bvcA).
Figure 3D:
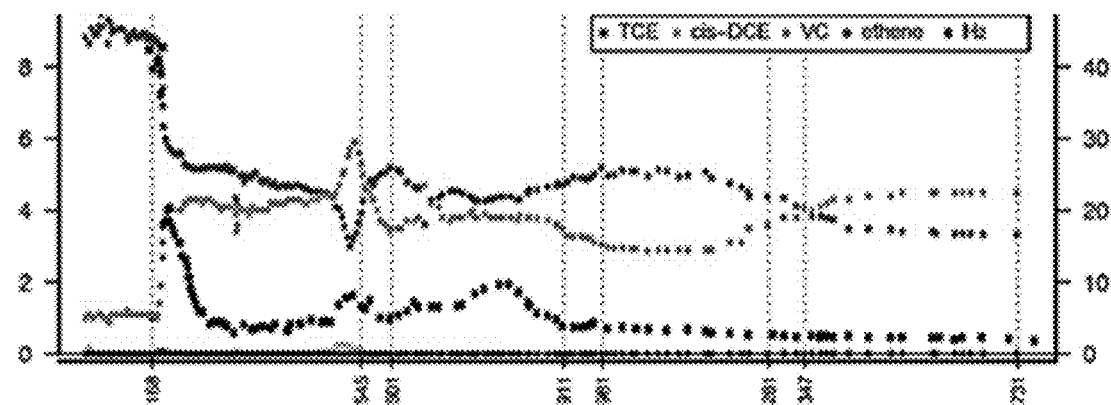
FIG. 3D illustrates chloroethene/ethene/hydrogen concentrations in the EV2L reactor.

The rdh gene clustering supports the assignment of a detected vinyl chloride reductase vcrA gene to the numerically less abundant Ev2, a second *Dehalococcoides*-like operational strain. In addition to vcrA, Ev2 is predicted to contain at least 9 other orthologue groups (10, 11, 13, 15, 17, 20, 21, 30, 32). In contrast to Ev1, Ev2 declined precipitously in the final 500 days of the time course. At day 168, prior to the introduction of formate-limiting conditions, the mean estimate of rdh gene count in Ev2 was 1500+/−600 copies per 25 pg of total community DNA. By the end of experiment, the mean estimate of Ev2 was 90+/−60 copies. Moreover, the decline in Ev2 correlates with changes in reactor's chemical performance, where the percentage of TCE converted fully to ethene dropped from 90% to 30% (FIG. 3C). At day 600, Ev2 was estimated to constitute more than $1/10^{th}$ of the total *Dehalococcoides* population, but by the end, it constituted less than $1/200^{th}$. Because the dominant tceA-containing strain Ev1 remained in far greater abundance, the dramatic decline in the vcrA-containing-population was not obvious from 16S rRNA-based qPCR measurements alone (FIG. 3D).

Ev3, a third operationally defined *Dehalococcoides*-like strain containing RD-OG 1, 12, 28, 38, 40, and 48 was even rarer. This strain appears to have gained a modest presence by day 900, reaching an estimated mean of 40+/−20 copies per 25 pg of total community DNA. This strain was near the limit of detection at the experiment's onset and was no longer detected in the last 300 days of the time-course. The detection of this strain at such low absolute copy numbers highlights the sensitivity of this nl-qPCR platform for tracking rare populations in mixed bacterial ecosystems. This rare *Dehalococcoides*-like strain was not detected when similar samples were studied using a less sensitive tiling DNA-DNA hybridization microarray approach.

Ev4, a fourth-operational non-*Dehalococcoides*-like strain, was also detected. It is predicted to contain genes from orthologue groups 6 and 9. The known substrate range of orthologue group 6 members, so far found in *Dehalobacter* and *Desulfitobacterium* isolates, includes PCE as well as 1,2-DCA (Marzorati et al., (2007) *Appl. Environ. Microbiol.* 73: 2990-2999; De Wildeman et al., (2003) *Appl. Environ. Microbiol.* 69: 5643-5647; Suyama et al., (2002) *J. Bacteriol.* 184: 3419-3425), so this strain's precise role in a TCE-fed reactor is uncertain. Nevertheless, a niche for this strain was apparently stably maintained.

Linkage of rdh to hupL Genes:

The correlation among hupL and rdh gene counts allowed for the inference of linkages between functional genes. For instance, the genome of vcrA-containing operational strain Ev2 appears to contain a Pinellas-type HupL hydrogenase. Similarly, the gene abundance profile of the Cornell type HupL hydrogenase indicates that it is present in the numerically dominant tceA-containing population Ev1 (FIG. 3B). If applied to more systems, this approach can reveal whether particular rdh and hupL genes are in linkage disequilibrium. If hydrogenases have different kinetic characteristics that are phenotypically relevant, consistent linkage between particular rdh and specific hupL types can delineate niche boundaries between sub-populations. This ecological information may prove useful as a design lever for managing community structure during bioremediation, since the ratio of *Dehalococcoides* types influences the kinetics of different degradation steps.

Diametric Ev2 and *Geobacter* Population Shifts:

One strain's expansion consistently co-occurred with the recession of another strain and vice-versa (FIG. 3B). These shifts in a constantly fed mixed reactor are suggestive of fine-scale niche boundaries determining the outcome of direct competition. Despite automation, subtle shifts in chemical composition in a reactor can be sufficient to shift population. Diametric shifts can also reflect density-dependent fitness dynamics observed during phage-predation on a sub-population (Rodriguez-Valera et al., (2009) *Nat. Rev. Microbiol.* 7: 828-836). The stability of the dominant *Dehalococcoides*-type suggests that predation was not the dominant ecological process in these systems, although the frequency of sampling was inadequate to rule it out completely. The modest DNA input requirements associated with the nl-qPCR technique of the present disclosure do advantageously allow more frequent sampling regimes in experiments.

There was an diametric relationship between the vcrA-containing Ev2 population and the 16S rRNA marker gene for *Geobacter* (FIG. 3C). *Geobacter* is most often studied as an iron-respiring bacterium (Lovley et al., (1993) *Arch. Microbiol.* 159: 336-344; Caccavo et al., (1994) *Appl. Environ. Microbiol.* 60: 3752-3759). One species of *Geobacter* has been shown to carry rdh genes and the capacity for growth-linked PCE-reduction (Sung et al., (2006) *Appl. Environ. Microbiol.* 72: 2775-2782; Wagner et al., (2012) *BMC Genomics.* 13: 200). The negative correlation between a presumed *Geobacter* strain and Ev2 is consistent with competition for a shared resource, such as hydrogen, acetate, or a CAH electron acceptor, although other explanations for the diametric relations cannot be excluded. The two-order of magnitude predicted increase in *Geobacter* population between days 1281 and 1347 coincided with a decline in the vcrA-type Ev2, but no decline was detected in the tceA-containing Ev1 strain. Hydrogen concentrations gradually decreased from 5 nM to 1-2 nM over the period of 600 to 1731 days, corresponding to the decrease of Ev2 strain. Competition for hydrogen might be a factor for this decrease, since previous studies of different VC-respiring *Dehalococcoides* strains reported hydrogen thresholds near 1 nM (Cupples & Spormann (2004) *Environ. Sci. & Technol.* 38: 1102-1107; Sung et al., (2006) *Appl. Environ. Microbiol.* 72: 1980-1987).

Since increases in *Geobacter* 16S gene copies were observed after two sampling events, these events may have influenced the selective conditions within the reactor. For instance, an introduction of trace oxygen or a change in reactor pH could tip the ecological balance in the *Geobacter*-like organism's favor. The reactor appeared to return to *Dehalococcoides*-favorable equilibrium between days 981-1281, but a similar re-equilibration did not occur after the subsequent *Geobacter* increase at day 1347, indicating a new stable state was reached (FIGS. 3C and 3D).

*Geobacter* and multiple *Dehalococcoides*-like strains often co-inhabit contaminated sediment environments. It has now been shown that rdh gene profiling by nl-qPCR using the methods of the disclosure can be useful for monitoring competition among closely related strains. Characterization of the biochemical potential, population stoichiometry, and perturbation-response-phenotypes of relevant organohalogen-respiring strains is a prerequisite for accurate modeling.

One aspect of the disclosure encompasses embodiments of a method for identifying a dechlorinating microbial organism, or a plurality of said microbial organisms, in a sample comprising: (a) obtaining a sample suspected of having a population of at least one microbial strain having at least one species of a reductive dehalogenase enzyme; (b) isolating nucleic acid from the sample; (c) applying the isolated nucleic acid to a microfluidic device configured for quantitative real-time PCR and comprising a panel of reductive dehalogenase (rdh)-specific PCR primer pairs, wherein each primer pair of the panel is selected to allow amplification of a specific target nucleotide sequence under a common PCR protocol; (d) simultaneously performing quantitative real-time PCR on the isolated nucleic acid in the microfluidic device with each rdh-specific PCR primer pair of said panel and under conditions wherein the presence of a microbial reductive dehalogenase (rdh)-related nucleic acid sequence results in at least one detectable amplicon encoding a region of a reductive dehalogenase (rdh); (e) detecting the at least one amplicon of step (d); (f) identifying the reductive dehalogenase enzyme encoded by the at least one amplicon; and (g) identifying the microbial strain or strains in the sample of step (a) that has at least one reductive dehalogenase enzyme.

In embodiments of this aspect of the disclosure, the sample can react with a primer pair in a total reaction volume of between about 3 nanoliters and about 500 nanoliters.

In embodiments of this aspect of the disclosure, the at least one primer of each primer pair can have a detectable label attached thereto.

In embodiments of this aspect of the disclosure, the detectable label is a fluorescent dye.

In embodiments of this aspect of the disclosure, the panel of reductive dehalogenase (rdh)-specific PCR primer pairs comprises at least one PCR primer pair selected from the group of PCR primer pairs according to Table 3.

In embodiments of this aspect of the disclosure, the method can further comprise the step of quantitatively determining the population of microbial strains in the sample of step (a) that have a reductive dehalogenase enzyme.

In embodiments of this aspect of the disclosure, the sample can be a sample obtained from a location suspected of comprising at least one microbial strain having a reductive dehalogenase (rdh) enzyme.

In embodiments of this aspect of the disclosure, the method can further comprise the step of obtaining an aqueous sample from a non-aqueous sample.

In embodiments of this aspect of the disclosure, the method can further comprise the step of classifying the identified reductive dehalogenase enzyme(s) encoded by the at least one amplified PCR product according to their respective reductive dehalogenase (rdh) orthologous groups.

In embodiments of this aspect of the disclosure, the panel of reductive dehalogenase (rdh)-specific PCR primer pairs consists essentially of at least one PCR primer pair selected from the group of PCR primer pairs according to Table 3.

In embodiments of this aspect of the disclosure, the panel of reductive dehalogenase (rdh)-specific PCR primer pairs consists of at least one PCR primer pair selected from the group of PCR primer pairs according to Table 3.

Another aspect of the disclosure encompasses embodiments of a microfluidic nanoliter-quantitative PCR device configured for quantitative real-time PCR and comprising a panel of reductive dehalogenase (rdh)-specific PCR primer pairs.

In some embodiments of this aspect of the disclosure, the panel of reductive dehalogenase (rdh)-specific PCR primer pairs comprises at least one PCR primer pair selected from the group of PCR primer pairs according to Table 3.

In some embodiments of this aspect of the disclosure, the panel of reductive dehalogenase (rdh)-specific PCR primer pairs consists essentially of at least one PCR primer pair selected from the group of PCR primer pairs according to Table 3.

In some embodiments of this aspect of the disclosure, the panel of reductive dehalogenase (rdh)-specific PCR primer pairs consists of the PCR primer pairs according to Table 3.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Development of a rdh qPCR Assay Suite:

A suite of novel qPCR primer pairs was designed to detect and distinguish between full-length and near-full-length reductive dehalogenase (rdh) gene groups. The Dehalogenase protein family (Pfam v 26.0) PF13486 (Punta et al., (2012) *Nucl. Acids Res.* 40: D290-D301) as a database of non-redundant Rdh protein sequences was used and consideration was limited to sequences 350-700 amino acids in length. Corresponding rdh nucleotide sequences were downloaded from NCBI (Accession numbers are given in Table 1).

Pfam sequences were clustered based on percent pairwise identity (PID) using blastp as described in Altschul et al., (1990) *J. Mol. Biol.* 215: 403-410, incorporated herein in its entirety by reference). Assay primer pairs were designed for 54 references sequences, most with at least one known high-PID homologue (>90% amino acid level). A Python script directed the software primer3 (Rozen & Skaletsky (2000) *Methods Mol. Biol.* 132: 365-386, incorporated herein by reference in its entirety) to generate thousands of candidate primer pairs that were ranked based on oligonucleotide complementarity to high-PID sequences with the primary reference sequence. Where possible, two assay types for each reference sequence were selected. The first was 'specific' to a reference sequence and those homologues with high PID values. The second 'extended' the number of sequences matched by the primers to include the reference sequence as well as many homologue sequences as possible.

Example 2

Initial Screening of Candidate Assays:

Primer performance data were collected using a SMART-CHIP MYDESIGN® (Wafergen Biosystems, Fremont, Calif.) platform. Chips were prepared by robotically dispensing oligonucleotide primers (Integrated DNA Technology) at a final concentration of 1 µM into 100 nL wells. Assay primer pairs were tested using both (20 sample×248 Assay) and (12 Sample×384 Assay) formats. For each sample, data were collected from two separate chip runs using a standard WaferGen protocol: 95° C. for 3 min, then 40 cycles of 95° C. for 60 sec and 60° C. for 70 sec.

Candidate assay primer pairs were physically tested against a collection of 500 bp synthesized linear DNA standards (Integrated DNA Technology) diluted to concentrations of 20,000, 2000, 200, and 20 copies per 100 nL reaction well. Assay primer pairs at 5 copies per reaction well were also tested.

Candidate assay primer pairs that failed to amplify standards at 5 copies per well or reproducibly amplified the negative control before cycle 28 were excluded from further consideration. Candidate assay primer pairs with PCR efficiencies less than 85% were also excluded, thereby providing 168 assay primer pairs (i.e. primer pairs) that met these requirements. The primers (forward and reverse primers) are listed in Table 2. Primer pairs selected for use in the methods of the disclosure are given in Table 3.

TABLE 2

| Primers | | |
|---|---|---|
| SEQ ID NO: 1 | AAC60788.1_378_ext_F_1302 | TGGATTCATGATGGCGTTGA |
| SEQ ID NO: 2 | AAC60788.1_378_ext_R_1391 | ACCATAGCCCAATGCATCAT |
| SEQ ID NO: 3 | AAC60788.1_624_ext_F_1302 | TGGATTCATGATGGCGTTGA |
| SEQ ID NO: 4 | AAC60788.1_624_ext_R_1384 | CCCAATGCATCATCCATACCA |
| SEQ ID NO: 5 | AAD44542.1_105_ext_F_984 | TTCTGCCGGGTATGCAAAAA |
| SEQ ID NO: 6 | AAD44542.1_105_ext_R_1086 | CACTGTTCCAACGCAGGTAT |
| SEQ ID NO: 7 | AAD44542.1_11_spec_F_1016 | TTGTCCAAACGACGCGATTA |
| SEQ ID NO: 8 | AAD44542.1_11_spec_R_1091 | AAAGTCACTGTTCCAACGCA |
| SEQ ID NO: 9 | AAD44542.1_1304_ext_F_1067 | ATACCTGCGTTGGAACAGTG |
| SEQ ID NO: 10 | AAD44542.1_1304_ext_R_1201 | CCTGCTTTATGGAACCAGGA |
| SEQ ID NO: 11 | AAD44542.1_14_spec_F_742 | GCTGCATTGCCGTCATTATG |
| SEQ ID NO: 12 | AAD44542.1_14_spec_R_868 | GACAATTCTCCCAGACCTGC |
| SEQ ID NO: 13 | AAD44542.1_43_ext_F_849 | GCAGGTCTGGGAGAATTGTC |
| SEQ ID NO: 14 | AAD44542.1_43_ext_R_934 | GTCGTTACTGCGGCTACTTT |
| SEQ ID NO: 15 | AAD44542.1_7_spec_F_572 | TACAGTCGGACTCATGAGCA |
| SEQ ID NO: 16 | AAD44542.1_7_spec_R_766 | TTGGCCATAATGACGGCAAT |
| SEQ ID NO: 17 | AAQ54585.2_1_spec_F_576 | GTGTTTCTGGCGGGAATGTA |
| SEQ ID NO: 18 | AAQ54585.2_1_spec_R_748 | GTCCAGCGATCGTCATAAGG |
| SEQ ID NO: 19 | AAQ54585.2_1053_ext_F_1446 | TGCTCCTGGAACAAAATCGA |
| SEQ ID NO: 20 | AAQ54585.2_1053_ext_R_1544 | CCACTCATCGAACTTACGGG |
| SEQ ID NO: 21 | AAQ54585.2_1536_ext_F_1292 | GGCGATCTCCCATGTGAAAG |
| SEQ ID NO: 22 | AAQ54585.2_1536_ext_R_1474 | TGCCAGGCATCGATTTTGTT |
| SEQ ID NO: 23 | AAQ54585.2_3115_ext_F_1203 | TTGGAACTTGTTCCGGACAA |
| SEQ ID NO: 24 | AAQ54585.2_3115_ext_R_1316 | GGGGTCTTTCACATGGGAGA |
| SEQ ID NO: 25 | AAR24308.1_0_spec_F_235 | GCAAAACAGAAAGCAGACCG |
| SEQ ID NO: 26 | AAR24308.1_0_spec_R_352 | CATGTGAAAAACCTGCCTGC |
| SEQ ID NO: 27 | AAR24308.1_4_spec_F_183 | TCAAGTTGCGTATGCCAGTT |
| SEQ ID NO: 28 | AAR24308.1_4_spec_R_352 | CATGTGAAAAACCTGCCTGC |
| SEQ ID NO: 29 | AAR24308.1_9_spec_F_918 | CACAGATTTGCCATTGGTGC |
| SEQ ID NO: 30 | AAR24308.1_9_spec_R_1042 | AGGAAGGAACATCATCCGGA |

TABLE 2-continued

Primers

| SEQ ID NO: 31 | AAT64888.1_1_spec_F_983 | TAATGGAGGCCGAGTTCAGA |
| SEQ ID NO: 32 | AAT64888.1_1_spec_R_1106 | ACGACCTTGTTCGGAAAGAC |
| SEQ ID NO: 33 | AAT64888.1_18_spec_F_922 | AACGTTCTCTAGGGTGGTCA |
| SEQ ID NO: 34 | AAT64888.1_18_spec_R_1002 | TCTGAACTCGGCCTCCATTA |
| SEQ ID NO: 35 | AAW39060.1_1596_spec_F_1129 | GAGTTGAAGCTTGGGGTCC |
| SEQ ID NO: 36 | AAW39060.1_1596_spec_R_1293 | CGGCATCTATAGGCTTGGTG |
| SEQ ID NO: 37 | AAW39060.1_1629_spec_F_1025 | ACCTATGGACCCATGCTCTT |
| SEQ ID NO: 38 | AAW39060.1_1629_spec_R_1146 | GACCCCAAGCTTCAACTCC |
| SEQ ID NO: 39 | AAW39060.1_2131_spec_F_1129 | GAGTTGAAGCTTGGGGTCC |
| SEQ ID NO: 40 | AAW39060.1_2131_spec_R_1289 | ATCTATAGGCTTGGTGGGGG |
| SEQ ID NO: 41 | AAW39215.1_0_spec_F_793 | TAGCACAGTGGCGTTTACAG |
| SEQ ID NO: 42 | AAW39215.1_0_spec_R_898 | CCAGACATAACACCCCAACC |
| SEQ ID NO: 43 | AAW39215.1_10_spec_F_879 | GGTTGGGGTGTTATGTCTGG |
| SEQ ID NO: 44 | AAW39215.1_10_spec_R_1034 | ACAAAACTTTCTGGCACCGA |
| SEQ ID NO: 45 | AAW39215.1_15_spec_F_801 | TGGCGTTTACAGGCATTTCT |
| SEQ ID NO: 46 | AAW39215.1_15_spec_R_898 | CCAGACATAACACCCCAACC |
| SEQ ID NO: 47 | AAW39215.1_7_spec_F_1052 | TGCTGATCTTTGCCCTTCTG |
| SEQ ID NO: 48 | AAW39215.1_7_spec_R_1229 | AACGCCGCAATAGGTATCTG |
| SEQ ID NO: 49 | AAW39229.1_204_spec_F_1257 | TGTACCGGCGTTTGTGTATT |
| SEQ ID NO: 50 | AAW39229.1_204_spec_R_1419 | GGTCAAGATCCCACCATTCG |
| SEQ ID NO: 51 | AAW39240.1_1121_spec_F_889 | AAAGATTCCCCTTTGTCGGG |
| SEQ ID NO: 52 | AAW39240.1_1121_spec_R_1081 | ATTACCCACATAGCCCGGTT |
| SEQ ID NO: 53 | AAW39240.1_1506_spec_F_666 | GGTGCTCAGGAAATGGATTCA |
| SEQ ID NO: 54 | AAW39240.1_1506_spec_R_819 | GGGCAGTCCACTGGAGTATA |
| SEQ ID NO: 55 | AAW39240.1_2398_spec_F_946 | CTGCGGTTTCCACCCATATG |
| SEQ ID NO: 56 | AAW39240.1_2398_spec_R_1081 | ATTACCCACATAGCCCGGTT |
| SEQ ID NO: 57 | AAW39240.1_4451_spec_F_801 | ATACTCCAGTGGACTGCCC |
| SEQ ID NO: 58 | AAW39240.1_4451_spec_R_961 | TGGGTGGAAACCGCAGTATA |
| SEQ ID NO: 59 | AAW39256.1_76_spec_F_1109 | CGGTTCACATCTTAGAGGACAG |
| SEQ ID NO: 60 | AAW39256.1_76_spec_R_1192 | CGTTCCATACCGGCATCTAT |
| SEQ ID NO: 61 | AAW39256.1_95_spec_F_1109 | CGGTTCACATCTTAGAGGACAG |
| SEQ ID NO: 62 | AAW39256.1_95_spec_R_1183 | CCGGCATCTATGGGTTTGG |
| SEQ ID NO: 63 | AAW39256.1_96_spec_F_1109 | CGGTTCACATCTTAGAGGACAG |
| SEQ ID NO: 64 | AAW39256.1_96_spec_R_1198 | CAGAAGCGTTCCATACCGG |
| SEQ ID NO: 65 | AAW39262.1_2442_spec_F_1050 | ATGTCTTCCCCTGCCATTCA |
| SEQ ID NO: 66 | AAW39262.1_2442_spec_R_1200 | AGGCATCAGCACAAATACCG |
| SEQ ID NO: 67 | AAW39273.1_1218_spec_F_1259 | CAACCTGTTCAGCTGTGCAT |
| SEQ ID NO: 68 | AAW39273.1_1218_spec_R_1416 | CACCCTCCATGCTGGTAAAG |
| SEQ ID NO: 69 | AAW39273.1_2015_ext_F_1101 | TGCGGTATCTGTGCTGAAAC |
| SEQ ID NO: 70 | AAW39273.1_2015_ext_R_1183 | TGGCCGCAATTATTATCCCA |
| SEQ ID NO: 71 | AAW39843.1_0_spec_F_1212 | GAATTTGGCTCAGTTTGCGG |
| SEQ ID NO: 72 | AAW39843.1_0_spec_R_1324 | GCGCATTTACGGCAAGTATG |
| SEQ ID NO: 73 | AAW39843.1_13_spec_F_1169 | TATAGCAGAGATGGGACGCA |
| SEQ ID NO: 74 | AAW39843.1_13_spec_R_1300 | AAACGGAATATCCCAGCGTC |
| SEQ ID NO: 75 | AAW39843.1_19_spec_F_1249 | CTGACTTGCCTCTAATGCCA |
| SEQ ID NO: 76 | AAW39843.1_19_spec_R_1324 | GCGCATTTACGGCAAGTATG |
| SEQ ID NO: 77 | AAW40581.1_4941_spec_F_202 | GCACTACCGCCGCTTTAAA |
| SEQ ID NO: 78 | AAW40581.1_4941_spec_R_276 | GGAGTATCCGCCCGTTATTC |
| SEQ ID NO: 79 | AAW40581.1_91_spec_F_957 | CTGAACGAGGTAACCGAACC |
| SEQ ID NO: 80 | AAW40581.1_91_spec_R_1046 | TACTTCGTAGGGAGTGCCAT |
| SEQ ID NO: 81 | AAW40581.1_96_spec_F_1027 | ATGGCACTCCCTACGAAGTA |
| SEQ ID NO: 82 | AAW40581.1_96_spec_R_1216 | ACCATTTCGTCAGCCACAAT |

TABLE 2-continued

Primers

| | | |
|---|---|---|
| SEQ ID NO: 83 | AAW40581.1_98_spec_F_886 | CCTTTGACCCCAGCAAGATT |
| SEQ ID NO: 84 | AAW40581.1_98_spec_R_1046 | TACTTCGTAGGGAGTGCCAT |
| SEQ ID NO: 85 | AAW40589.1_12_spec_F_1218 | GGCAGTGTTCACGGCTATTT |
| SEQ ID NO: 86 | AAW40589.1_12_spec_R_1344 | ATTTGGCAGGGCATTCATCA |
| SEQ ID NO: 87 | AAW40589.1_5_spec_F_1186 | GCAACTCAAACGTCTGCATC |
| SEQ ID NO: 88 | AAW40589.1_5_spec_R_1312 | CAGGTATGGCAGAAACGGAA |
| SEQ ID NO: 89 | ABQ16695.1_3523_spec_F_1205 | TGCTAATTCCAATCCCACCAA |
| SEQ ID NO: 90 | ABQ16695.1_3523_spec_R_1302 | CCCAGAAATTGTGACAGGCA |
| SEQ ID NO: 91 | ABQ16695.1_627_spec_F_1209 | AATTCCAATCCCACCAAGCT |
| SEQ ID NO: 92 | ABQ16695.1_627_spec_R_1302 | CCCAGAAATTGTGACAGGCA |
| SEQ ID NO: 93 | ABQ16703.1_2_spec_F_1242 | TCACGGTGGAGTGGAGTATT |
| SEQ ID NO: 94 | ABQ16703.1_2_spec_R_1331 | GGTGGGAGCTAAAGGCAAAT |
| SEQ ID NO: 95 | ABQ16703.1_54_spec_F_1312 | ATTTGCCTTTAGCTCCCACC |
| SEQ ID NO: 96 | ABQ16703.1_54_spec_R_1393 | CAAGCATCGGCACAAATACC |
| SEQ ID NO: 97 | ABY28312.1_3639_spec_F_842 | CGCTCACTTGGCTATACCTG |
| SEQ ID NO: 98 | ABY28312.1_3639_spec_R_942 | CGGTTTCCTTCCGTAATACCG |
| SEQ ID NO: 99 | ACF24861.1_1091_spec_F_1344 | TGGCAGGCGGATAAATTCTT |
| SEQ ID NO: 100 | ACF24861.1_1091_spec_R_1437 | CGGCACTGTCAAACCCATAA |
| SEQ ID NO: 101 | ACF24861.1_1415_ext_F_1342 | TGTGGCAGGCGGATAAATTC |
| SEQ ID NO: 102 | ACF24861.1_1415_ext_R_1430 | GTCAAACCCATAAACCGGCA |
| SEQ ID NO: 103 | ACH87594.1_2227_ext_F_161 | CAAGGTGGATGCAAAGTACCA |
| SEQ ID NO: 104 | ACH87594.1_2227_ext_R_340 | TTGATCCCAAGTCTTTCCGC |
| SEQ ID NO: 105 | ACH87594.1_2865_ext_F_161 | CAAGGTGGATGCAAAGTACCA |
| SEQ ID NO: 106 | ACH87594.1_2865_ext_R_299 | CCCCGTATCTTTCTTGCCTG |
| SEQ ID NO: 107 | ACH87594.1_437_pr_F_407 | AACCCAGCGCCATAATGAAA |
| SEQ ID NO: 108 | ACH87594.1_437_pr_R_516 | GACCACCACTTACGCAGTTA |
| SEQ ID NO: 109 | ACH87594.1_4754_ext_F_138 | ACGGAAACCTCAGAATTTCCA |
| SEQ ID NO: 110 | ACH87594.1_4754_ext_R_299 | CCCCGTATCTTTCTTGCCTG |
| SEQ ID NO: 111 | ACH87594.1_522_pr_F_353 | GACAAATGCAGAAACAGGCG |
| SEQ ID NO: 112 | ACH87594.1_522_pr_R_516 | GACCACCACTTACGCAGTTA |
| SEQ ID NO: 113 | ACH87594.1_646_pr_F_401 | CATGTTAACCCAGCGCCATA |
| SEQ ID NO: 114 | ACH87594.1_646_pr_R_516 | GACCACCACTTACGCAGTTA |
| SEQ ID NO: 115 | ACH87598.1_3654_ext_F_690 | TTTTCTGAGGAAGCTTGGCT |
| SEQ ID NO: 116 | ACH87598.1_3654_ext_R_873 | CTTGTCCGGAGCAAGTTCC |
| SEQ ID NO: 117 | ACL18777.1_2120_ext_F_1011 | GATTTCTGCCGGGTATGCAA |
| SEQ ID NO: 118 | ACL18777.1_2120_ext_R_1117 | TCACTGTTCCAGCGCAGATA |
| SEQ ID NO: 119 | ACL18777.1_2126_ext_F_1016 | CTGCCGGGTATGCAAGAAAT |
| SEQ ID NO: 120 | ACL18777.1_2126_ext_R_1117 | TCACTGTTCCAGCGCAGATA |
| SEQ ID NO: 121 | ACL18777.1_38_spec_F_248 | TAATGATCAGTGGCTGGGGA |
| SEQ ID NO: 122 | ACL18777.1_38_spec_R_421 | AAAATACCCAGCGCTCCATC |
| SEQ ID NO: 123 | ACL18777.1_77_spec_F_355 | CACAGGTTGCCATGTACCAT |
| SEQ ID NO: 124 | ACL18777.1_77_spec_R_485 | TATGGGCAGTTTCTCCTGGT |
| SEQ ID NO: 125 | ACZ61261.1_113_spec_F_456 | TCTGCTTTACCGGTTGAACC |
| SEQ ID NO: 126 | ACZ61261.1_113_spec_R_568 | ACCTGAGGCGTACCGAAATA |
| SEQ ID NO: 127 | ACZ61261.1_36_spec_F_398 | CACCTCTTCGTCATGGATGG |
| SEQ ID NO: 128 | ACZ61261.1_36_spec_R_475 | GGTTCAACCGGTAAAGCAGA |
| SEQ ID NO: 129 | ACZ61261.1_94_spec_F_409 | CATGGATGGGGCTTGATGTT |
| SEQ ID NO: 130 | ACZ61261.1_94_spec_R_568 | ACCTGAGGCGTACCGAAATA |
| SEQ ID NO: 131 | ACZ61261.1_98_spec_F_692 | TCCGGTTGGTTTTCAGGATG |
| SEQ ID NO: 132 | ACZ61261.1_98_spec_R_785 | CAGTGCATTTTCTTTGGCGG |
| SEQ ID NO: 133 | ACZ61272.1_0_spec_F_1075 | CCGGTTTGTGTGAATCAGGA |
| SEQ ID NO: 134 | ACZ61272.1_0_spec_R_1175 | GGCTAGAGGAAGGTCAGTGA |

TABLE 2-continued

Primers

| SEQ ID NO: | Name | Sequence |
|---|---|---|
| SEQ ID NO: 135 | ACZ61272.1_4_spec_F_1085 | TGAATCAGGACGTACCACCT |
| SEQ ID NO: 136 | ACZ61272.1_4_spec_R_1175 | GGCTAGAGGAAGGTCAGTGA |
| SEQ ID NO: 137 | ACZ61272.1_8_spec_F_1156 | TCACTGACCTTCCTCTAGCC |
| SEQ ID NO: 138 | ACZ61272.1_8_spec_R_1261 | CTGATTGTGTTGGAAGGGCA |
| SEQ ID NO: 139 | ACZ61277.1_0_spec_F_741 | GAAAAGCTGGTGATTCCGGA |
| SEQ ID NO: 140 | ACZ61277.1_0_spec_R_886 | GTTTGCCAAACAGATGCCAG |
| SEQ ID NO: 141 | ACZ61277.1_1673_ext_F_1317 | GGTATCTGCATGGGTTCCTG |
| SEQ ID NO: 142 | ACZ61277.1_1673_ext_R_1445 | ACCAAAGAACTTGTCAGCCT |
| SEQ ID NO: 143 | ACZ61277.1_2882_ext_F_1317 | GGTATCTGCATGGGTTCCTG |
| SEQ ID NO: 144 | ACZ61277.1_2882_ext_R_1446 | AACCAAAGAACTTGTCAGCCT |
| SEQ ID NO: 145 | ACZ61277.1_3_spec_F_741 | GAAAAGCTGGTGATTCCGGA |
| SEQ ID NO: 146 | ACZ61277.1_3_spec_R_841 | ACTCTCAAATTGCCGCTACC |
| SEQ ID NO: 147 | ACZ61277.1_7_spec_F_1244 | TCCGGGCAAAAGGTTTTCT |
| SEQ ID NO: 148 | ACZ61277.1_7_spec_R_1357 | GCATTGTCCACGTTGAACAC |
| SEQ ID NO: 149 | ACZ61293.1_101_spec_F_876 | AAACTCCGCACCTTTGATCC |
| SEQ ID NO: 150 | ACZ61293.1_101_spec_R_993 | CCGGCTTGGTAAATTCAGGT |
| SEQ ID NO: 151 | ACZ61293.1_61_spec_F_931 | TCAGCGGTGAAACCAATGAA |
| SEQ ID NO: 152 | ACZ61293.1_61_spec_R_1038 | AGGGGGTATTCTCGTATCGG |
| SEQ ID NO: 153 | ACZ61293.1_764_spec_F_955 | CCCTGAACGAAGTAACCGAA |
| SEQ ID NO: 154 | ACZ61293.1_764_spec_R_1038 | AGGGGGTATTCTCGTATCGG |
| SEQ ID NO: 155 | ACZ61341.1_1883_spec_F_437 | GGACAGGTGGCATATTACCC |
| SEQ ID NO: 156 | ACZ61341.1_1883_spec_R_517 | TCGGGAGAAAGCTCAACCTT |
| SEQ ID NO: 157 | ACZ61341.1_2104_spec_F_270 | TTTTCCCAGATAGTCAGGCG |
| SEQ ID NO: 158 | ACZ61341.1_2104_spec_R_456 | GGGTAATATGCCACCTGTCC |
| SEQ ID NO: 159 | ACZ61341.1_4924_spec_F_258 | CGCGAACATGGTTTTTCCC |
| SEQ ID NO: 160 | ACZ61341.1_4924_spec_R_456 | GGGTAATATGCCACCTGTCC |
| SEQ ID NO: 161 | ACZ61341.1_589_spec_F_259 | GCGAACATGGTTTTTCCCAG |
| SEQ ID NO: 162 | ACZ61341.1_589_spec_R_456 | GGGTAATATGCCACCTGTCC |
| SEQ ID NO: 163 | ACZ62362.1_1266_ext_F_957 | TTTATCCGCGGTTTGGGTTA |
| SEQ ID NO: 164 | ACZ62362.1_1266_ext_R_1097 | GTTGGTTGTGCCGTATTTGG |
| SEQ ID NO: 165 | ACZ62362.1_137_spec_F_178 | TTAACAAGAACCCGTGGTGG |
| SEQ ID NO: 166 | ACZ62362.1_137_spec_R_304 | AAGTCAGCTACAGTGGGTCT |
| SEQ ID NO: 167 | ACZ62362.1_3471_ext_F_957 | TTTATCCGCGGTTTGGGTTA |
| SEQ ID NO: 168 | ACZ62362.1_3471_ext_R_1063 | GAAGACATACGCCCGTGTTC |
| SEQ ID NO: 169 | ACZ62362.1_361_spec_F_48 | TTTCATTCCACACTCTCGCG |
| SEQ ID NO: 170 | ACZ62362.1_361_spec_R_197 | CCACCACGGGTTCTTGTTAA |
| SEQ ID NO: 171 | ACZ62362.1_37_spec_F_105 | GGTTTAGGGACTATGAGCGC |
| SEQ ID NO: 172 | ACZ62362.1_37_spec_R_197 | CCACCACGGGTTCTTGTTAA |
| SEQ ID NO: 173 | ACZ62362.1_389_spec_F_94 | TAGTCGGAGCAGGTTTAGGG |
| SEQ ID NO: 174 | ACZ62362.1_389_spec_R_197 | CCACCACGGGTTCTTGTTAA |
| SEQ ID NO: 175 | ACZ62362.1_67_spec_F_178 | TTAACAAGAACCCGTGGTGG |
| SEQ ID NO: 176 | ACZ62362.1_67_spec_R_358 | ATTTCGGGGTTTCAAGGTC |
| SEQ ID NO: 177 | ACZ62391.1_11_ext_F_550 | ATGGGAGCGTACCAAAATGG |
| SEQ ID NO: 178 | ACZ62391.1_11_ext_R_707 | TAGAGTCATCGGCTGAGCTT |
| SEQ ID NO: 179 | ACZ62391.1_13_ext_F_550 | ATGGGAGCGTACCAAAATGG |
| SEQ ID NO: 180 | ACZ62391.1_13_ext_R_703 | GTCATCGGCTGAGCTTTCTT |
| SEQ ID NO: 181 | ACZ62391.1_3_ext_F_550 | ATGGGAGCGTACCAAAATGG |
| SEQ ID NO: 182 | ACZ62391.1_3_ext_R_667 | CATTTGGGATCTGCCAGGTT |
| SEQ ID NO: 183 | ACZ62391.1_6_ext_F_479 | TCCTGATCAACCCGGTAAGT |
| SEQ ID NO: 184 | ACZ62391.1_6_ext_R_667 | CATTTGGGATCTGCCAGGTT |
| SEQ ID NO: 185 | ACZ62413.1_0_spec_F_1196 | ACCCACCACGCCTATAGATT |
| SEQ ID NO: 186 | ACZ62413.1_0_spec_R_1274 | CTGAGTCGGACAGGTTTGAG |

TABLE 2-continued

Primers

| SEQ ID NO: 187 | ACZ62419.1_0_spec_F_1235 | TCTTCCTCTAGCGCCTACTC |
| SEQ ID NO: 188 | ACZ62419.1_0_spec_R_1312 | GCTTCGGCACATATACCACA |
| SEQ ID NO: 189 | ACZ62419.1_30_spec_F_1150 | TAGGTGAGCACAGCCGTAT |
| SEQ ID NO: 190 | ACZ62419.1_30_spec_R_1254 | GAGTAGGCGCTAGAGGAAGA |
| SEQ ID NO: 191 | ACZ62419.1_5_spec_F_1208 | GCGGACTCATGCTGTCTTTT |
| SEQ ID NO: 192 | ACZ62419.1_5_spec_R_1308 | CGGCACATATACCACAGGTC |
| SEQ ID NO: 193 | ACZ62441.1_2_spec_F_1111 | GGGCTGCCATGACTATTGAG |
| SEQ ID NO: 194 | ACZ62441.1_2_spec_R_1237 | CAGTTGTGACAAAAGCGACG |
| SEQ ID NO: 195 | ACZ62459.1_179_spec_F_1518 | GGTGTTTACGAACCTCCGAA |
| SEQ ID NO: 196 | ACZ62459.1_179_spec_R_1594 | TTCACCCCCATCGGAGTATT |
| SEQ ID NO: 197 | ACZ62459.1_430_spec_F_112 | CATTCTCCATGCAGGGTCAG |
| SEQ ID NO: 198 | ACZ62459.1_430_spec_R_206 | TTCCCAGCTGAAAGGGGTAA |
| SEQ ID NO: 199 | ACZ62477.1_52_ext_F_809 | TGCCATACCCAACAAATGCA |
| SEQ ID NO: 200 | ACZ62477.1_52_ext_R_913 | TACCAGACCGCAAAACCTTC |
| SEQ ID NO: 201 | ACZ62477.1_760_ext_F_809 | TGCCATACCCAACAAATGCA |
| SEQ ID NO: 202 | ACZ62477.1_760_ext_R_927 | AGCGGGCATAAGAATACCAG |
| SEQ ID NO: 203 | ACZ62477.1_782_spec_F_809 | TGCCATACCCAACAAATGCA |
| SEQ ID NO: 204 | ACZ62477.1_782_spec_R_914 | ATACCAGACCGCAAAACCTT |
| SEQ ID NO: 205 | ACZ62486.1_0_ext_F_1024 | GCGGTGTTATGACTCCCAAA |
| SEQ ID NO: 206 | ACZ62486.1_0_ext_R_1187 | CTTGCTGATAGCTCCCATCG |
| SEQ ID NO: 207 | ACZ62486.1_1038_spec_F_926 | GGGTCTGGGATATATCTCGCT |
| SEQ ID NO: 208 | ACZ62486.1_1038_spec_R_1071 | CGTGCATTACCCGTACAGAG |
| SEQ ID NO: 209 | ACZ62486.1_319_spec_F_920 | CCTGTGGGGTCTGGGATATA |
| SEQ ID NO: 210 | ACZ62486.1_319_spec_R_1071 | CGTGCATTACCCGTACAGAG |
| SEQ ID NO: 211 | ACZ62486.1_47_spec_F_1024 | GCGGTGTTATGACTCCCAAA |
| SEQ ID NO: 212 | ACZ62486.1_47_spec_R_1195 | GGCTCATCCTTGCTGATAGC |
| SEQ ID NO: 213 | ACZ62486.1_970_ext_F_931 | TGGGATATATCTCGCTGGACA |
| SEQ ID NO: 214 | ACZ62486.1_970_ext_R_1043 | TTTGGGAGTCATAACACCGC |
| SEQ ID NO: 215 | ACZ62486.1_983_spec_F_113 | TGAAATGGCTTCAGCACCC |
| SEQ ID NO: 216 | ACZ62486.1_983_spec_R_245 | CATAGGGGAGGGCCTTTAT |
| SEQ ID NO: 217 | ACZ62492.1_147_spec_F_814 | GGACTATGCGTCAGCCATAC |
| SEQ ID NO: 218 | ACZ62492.1_147_spec_R_916 | TGGGCTTTGGTATTGTAGGC |
| SEQ ID NO: 219 | ACZ62492.1_799_spec_F_814 | GGACTATGCGTCAGCCATAC |
| SEQ ID NO: 220 | ACZ62492.1_799_spec_R_923 | CTGGAAGTGGGCTTTGGTAT |
| SEQ ID NO: 221 | ACZ62501.1_1067_spec_F_1077 | ATGTGGCGTTTCTGCCATAC |
| SEQ ID NO: 222 | ACZ62501.1_1067_spec_R_1219 | AACTGTTTCTTGCCGGGTAC |
| SEQ ID NO: 223 | ACZ62501.1_2033_spec_F_1084 | GTTTCTGCCATACCTGCACC |
| SEQ ID NO: 224 | ACZ62501.1_2033_spec_R_1219 | AACTGTTTCTTGCCGGGTAC |
| SEQ ID NO: 225 | ACZ62520.1_209_spec_F_874 | CTGCTACCCTTACCGGTTTG |
| SEQ ID NO: 226 | ACZ62520.1_209_spec_R_1013 | CATACCGGCATCAATGGGAG |
| SEQ ID NO: 227 | ACZ62520.1_3576_ext_F_994 | CTCCCATTGATGCCGGTATG |
| SEQ ID NO: 228 | ACZ62520.1_3576_ext_R_1095 | CCCAGGTTGGTTCATGCTC |
| SEQ ID NO: 229 | ACZ62520.1_3979_ext_F_882 | CTTACCGGTTTGGGTGAGG |
| SEQ ID NO: 230 | ACZ62520.1_3979_ext_R_1006 | GCATCAATGGGAGGTGTAGG |
| SEQ ID NO: 231 | ACZ62520.1_768_spec_F_866 | CATTGCCACTGCTACCCTTA |
| SEQ ID NO: 232 | ACZ62520.1_768_spec_R_1006 | GCATCAATGGGAGGTGTAGG |
| SEQ ID NO: 233 | ACZ62529.1_1422_spec_F_1329 | ACCACCGGCATTTTCAACA |
| SEQ ID NO: 234 | ACZ62529.1_1422_spec_R_1418 | GTCAAGATCCCACCATTCGG |
| SEQ ID NO: 235 | ACZ62529.1_1912_spec_F_1073 | TTTCCGCTTCTGCCATAGC |
| SEQ ID NO: 236 | ACZ62529.1_1912_spec_R_1223 | CAGCTTGCACTCAGGTTCAT |
| SEQ ID NO: 237 | ACZ62529.1_3935_ext_F_1257 | TGTACCGGCGTTTGTGTATT |
| SEQ ID NO: 238 | ACZ62529.1_3935_ext_R_1416 | CAAGATCCCACCATTCGGC |

TABLE 2-continued

Primers

| SEQ ID NO: 239 | ACZ62529.1_746_spec_F_796 | GTGTTTGTTATGCCGCCAAT |
| SEQ ID NO: 240 | ACZ62529.1_746_spec_R_901 | GCAGACTGCAAACCCTGATA |
| SEQ ID NO: 241 | ACZ62535.1_2901_spec_F_978 | CGTTATGTGGGTTCCGAGG |
| SEQ ID NO: 242 | ACZ62535.1_2901_spec_R_1152 | AGAAACGGTAAATGCCTGCA |
| SEQ ID NO: 243 | ACZ62535.1_2902_spec_F_977 | CCGTTATGTGGGTTCCGAG |
| SEQ ID NO: 244 | ACZ62535.1_2902_spec_R_1152 | AGAAACGGTAAATGCCTGCA |
| SEQ ID NO: 245 | ACZ62535.1_325_spec_F_1133 | TGCAGGCATTTACCGTTTCT |
| SEQ ID NO: 246 | ACZ62535.1_325_spec_R_1323 | TTTCGTTGGAATACTGGCGG |
| SEQ ID NO: 247 | ACZ62535.1_4389_spec_F_1133 | TGCAGGCATTTACCGTTTCT |
| SEQ ID NO: 248 | ACZ62535.1_4389_spec_R_1315 | GAATACTGGCGGCAGAGAG |
| SEQ ID NO: 249 | ADC73508.1_197_ext_F_106 | TGTTCCGCGGCTTTGAAATA |
| SEQ ID NO: 250 | ADC73508.1_197_ext_R_275 | GAGTATCCGCCCGTTATTCG |
| SEQ ID NO: 251 | ADC73508.1_20_spec_F_1019 | CCGCTATGAAAACACCCCTT |
| SEQ ID NO: 252 | ADC73508.1_20_spec_R_1205 | AGCCACAATCTTGCATTCCA |
| SEQ ID NO: 253 | ADC73508.1_202_spec_F_916 | TCAAGTACGGCTGGTTCAAG |
| SEQ ID NO: 254 | ADC73508.1_202_spec_R_1038 | AAGGGGTGTTTTCATAGCGG |
| SEQ ID NO: 255 | ADC73508.1_3_spec_F_877 | CACTCCACACCTTTGATCCC |
| SEQ ID NO: 256 | ADC73508.1_3_spec_R_1038 | AAGGGGTGTTTTCATAGCGG |
| SEQ ID NO: 257 | ADC73508.1_338_ext_F_49 | AAATCGAAGCCACCGTAGAC |
| SEQ ID NO: 258 | ADC73508.1_338_ext_R_125 | TATTTCAAAGCCGCGGAACA |
| SEQ ID NO: 259 | ADC74627.1_1_spec_F_757 | CGGCAGTAAATCCCACCAAT |
| SEQ ID NO: 260 | ADC74627.1_1_spec_R_876 | GTGCAGCGTTCTGAGTAGTT |
| SEQ ID NO: 261 | ADC74627.1_2_spec_F_757 | CGGCAGTAAATCCCACCAAT |
| SEQ ID NO: 262 | ADC74627.1_2_spec_R_875 | TGCAGCGTTCTGAGTAGTTG |
| SEQ ID NO: 263 | ADC74627.1_9_spec_F_741 | GATTTTGTATGCACACCGGC |
| SEQ ID NO: 264 | ADC74627.1_9_spec_R_876 | GTGCAGCGTTCTGAGTAGTT |
| SEQ ID NO: 265 | ADC74655.1_1033_spec_F_656 | ATCCGTTCCAGGCAATAAGC |
| SEQ ID NO: 266 | ADC74655.1_1033_spec_R_792 | GCAGAAACCCGTCACATGAA |
| SEQ ID NO: 267 | ADC74655.1_1058_spec_F_656 | ATCCGTTCCAGGCAATAAGC |
| SEQ ID NO: 268 | ADC74655.1_1058_spec_R_749 | CTTTTGCGAAGTGGGGATGT |
| SEQ ID NO: 269 | ADC74655.1_161_ext_F_876 | CAGTTTATCCGCGGGTTAGG |
| SEQ ID NO: 270 | ADC74655.1_161_ext_R_983 | CTGACCCATACGGCAATGTT |
| SEQ ID NO: 271 | ADC74655.1_166_ext_F_876 | CAGTTTATCCGCGGGTTAGG |
| SEQ ID NO: 272 | ADC74655.1_166_ext_R_982 | TGACCCATACGGCAATGTTC |
| SEQ ID NO: 273 | ADC74655.1_2926_ext_F_950 | GAGCGGTGTTGGTGAACATT |
| SEQ ID NO: 274 | ADC74655.1_2926_ext_R_1120 | GTTTCAGCACAGATACCGCA |
| SEQ ID NO: 275 | BAE84628.1_1113_spec_F_317 | AAATGCGGAAAGACTTGGGA |
| SEQ ID NO: 276 | BAE84628.1_1113_spec_R_411 | GGGTTAACATGGCACCCAAA |
| SEQ ID NO: 277 | BAE84628.1_3406_ext_F_1459 | GGAACAAAGTCGAGACCTGG |
| SEQ ID NO: 278 | BAE84628.1_3406_ext_R_1546 | TCATCAAACTTGCGGGCTG |
| SEQ ID NO: 279 | BAE84628.1_400_spec_F_317 | AAATGCGGAAAGACTTGGGA |
| SEQ ID NO: 280 | BAE84628.1_400_spec_R_405 | ACATGGCACCCAAATGTTGA |
| SEQ ID NO: 281 | BAE84628.1_4184_ext_F_1102 | GTGTTCCTATGGCCGTTCAG |
| SEQ ID NO: 282 | BAE84628.1_4184_ext_R_1229 | CTTGTCCGGAGCAAGTTCC |
| SEQ ID NO: 283 | BAF34982.1_9_spec_F_1138 | GGGAACAATCACGCGTATCA |
| SEQ ID NO: 284 | BAF34982.1_9_spec_R_1251 | CGGCATCTATAGGCTTGGTG |
| SEQ ID NO: 285 | BAG72170.1_2661_spec_F_1104 | CCTGCAAGAAGTGTGCAGAT |
| SEQ ID NO: 286 | BAG72170.1_2661_spec_R_1200 | ACTCTGGGTTTGCCGTCTA |
| SEQ ID NO: 287 | BAG72170.1_2758_spec_F_1001 | ACTCCTGAAACCGGTCCTAA |
| SEQ ID NO: 288 | BAG72170.1_2758_spec_R_1111 | CTTGCAGGAGTGGCAGAAG |
| SEQ ID NO: 289 | BAG72170.1_283_spec_F_1001 | ACTCCTGAAACCGGTCCTAA |
| SEQ ID NO: 290 | BAG72170.1_283_spec_R_1123 | ATCTGCACACTTCTTGCAGG |

TABLE 2-continued

Primers

| | | |
|---|---|---|
| SEQ ID NO: 291 | BAG72170.1_866_spec_F_1029 | CCTTTACCATGCTGACCGAT |
| SEQ ID NO: 292 | BAG72170.1_866_spec_R_1123 | ATCTGCACACTTCTTGCAGG |
| SEQ ID NO: 293 | BAI47830.1_259_spec_F_251 | AGTGAGCGGCATTTACAAGG |
| SEQ ID NO: 294 | BAI47830.1_259_spec_R_348 | GTAGAGCCATAGTTGCCACC |
| SEQ ID NO: 295 | BAI47830.1_561_spec_F_193 | AATGCCTGGTTTCCGTGAAG |
| SEQ ID NO: 296 | BAI47830.1_561_spec_R_348 | GTAGAGCCATAGTTGCCACC |
| SEQ ID NO: 297 | BAI70453.1_0_spec_F_309 | TCTTGGTTGGGTCCTCAGAA |
| SEQ ID NO: 298 | BAI70453.1_0_spec_R_459 | CGTTTTCATCCAGCTCCAGT |
| SEQ ID NO: 299 | BAI70453.1_10_spec_F_718 | TGGGTTATCAGGCTATGGCT |
| SEQ ID NO: 300 | BAI70453.1_10_spec_R_908 | ACCGGCATCAATAGGTTTGG |
| SEQ ID NO: 301 | BAI70453.1_14_spec_F_182 | ACAGAAAATTGCGGCGGATA |
| SEQ ID NO: 302 | BAI70453.1_14_spec_R_342 | CGGGGGTAGGAGATTTCTGA |
| SEQ ID NO: 303 | BAI70453.1_28_ext_F_1104 | GCCTGTGTGTACACCAAGAA |
| SEQ ID NO: 304 | BAI70453.1_28_ext_R_1289 | CCAGAAATCTTCGGCACCTT |
| SEQ ID NO: 305 | BAI70453.1_44_ext_F_1046 | GGTGAAATGCCAGAGTACCC |
| SEQ ID NO: 306 | BAI70453.1_44_ext_R_1241 | GTCAGGCCCGAATTCAGTAC |
| SEQ ID NO: 307 | BAI70453.1_45_ext_F_927 | GACTGCGCTAAATGCTCTGA |
| SEQ ID NO: 308 | BAI70453.1_45_ext_R_1065 | GGGTACTCTGGCATTTCACC |
| SEQ ID NO: 309 | BAI70453.1_6_spec_F_16 | TGATAACTTCTGGTGCTGCG |
| SEQ ID NO: 310 | BAI70453.1_6_spec_R_126 | TAACCTTACGGGCGTCAAAC |
| SEQ ID NO: 311 | CAD28790.2_81_pr_F_209 | TGAAAAGACTTTCGACCCGG |
| SEQ ID NO: 312 | CAD28790.2_81_pr_R_403 | ATGGCACCCAAATGTTGAGT |
| SEQ ID NO: 313 | CAD28790.2_953_pr_F_385 | CTCAACATTTGGGTGCCATG |
| SEQ ID NO: 314 | CAD28790.2_953_pr_R_484 | TCAAATTCTACAGCCCAGGC |
| SEQ ID NO: 315 | CAI83519.1_2479_spec_F_141 | AACAAAAGGCCATGGTGGG |
| SEQ ID NO: 316 | CAI83519.1_2479_spec_R_252 | GAGCAGTCATGGGATAAGCC |
| SEQ ID NO: 317 | CAI83531.1_104_spec_F_1181 | CACCGATTTACCTCTCTCGC |
| SEQ ID NO: 318 | CAI83531.1_104_spec_R_1267 | CAAGCCTCGGCACAGATAC |
| SEQ ID NO: 319 | CAI83566.1_1_spec_F_314 | ACAACGCATGCAAGATGGTA |
| SEQ ID NO: 320 | CAI83566.1_1_spec_R_464 | GGGAAGTCCTTGTTCTTCGG |
| SEQ ID NO: 321 | CAI83566.1_10_spec_F_444 | CCCGAAGAACAAGGACTTCC |
| SEQ ID NO: 322 | CAI83566.1_10_spec_R_539 | TACTTGCCCTGCACCAAAAA |
| SEQ ID NO: 323 | CAI83566.1_14_spec_F_1161 | CCTGGACACAAGGCATTCTT |
| SEQ ID NO: 324 | CAI83566.1_14_spec_R_1247 | CATACAGATACCGCAGCCTG |
| SEQ ID NO: 325 | CAI83566.1_4_spec_F_1134 | AAATGGGATTGTGCGCCTTA |
| SEQ ID NO: 326 | CAI83566.1_4_spec_R_1247 | CATACAGATACCGCAGCCTG |
| SEQ ID NO: 327 | CAI83566.1_6_spec_F_445 | CCGAAGAACAAGGACTTCCC |
| SEQ ID NO: 328 | CAI83566.1_6_spec_R_640 | CAAGATGAGCCGTACGTACC |
| SEQ ID NO: 329 | CAJ75430.1_2099_pr_F_321 | GCGGAAAGACTTGGGATCAA |
| SEQ ID NO: 330 | CAJ75430.1_2099_pr_R_408 | GTGGCATGACACCCGTATG |
| SEQ ID NO: 331 | CAJ75430.1_2693_pr_F_280 | CAGGCAAGAAAGATACGGGG |
| SEQ ID NO: 332 | CAJ75430.1_2693_pr_R_408 | GTGGCATGACACCCGTATG |
| SEQ ID NO: 333 | CAR57931.1_1638_pr_F_298 | GGAAAGACCTGCCCATACTT |
| SEQ ID NO: 334 | CAR57931.1_1638_pr_R_372 | CGCCTGTTTCTGCATTTGTC |
| SEQ ID NO: 335 | CAR57931.1_2137_pr_F_298 | GGAAAGACCTGCCCATACTT |
| SEQ ID NO: 336 | CAR57931.1_2137_pr_R_376 | AGAACGCCTGTTTCTGCATT |

TABLE 3

| qPCR primer pairs (assays)-SEQ ID NOs. | | | | | |
|---|---|---|---|---|---|
| 1 and 2 | 3 and 4 | 5 and 6 | 7 and 8 | 9 and 10 | 11 and 12 |
| 13 and 14 | 15 and 16 | 17 and 18 | 19 and 20 | 21 and 22 | 23 and 24 |
| 25 and 26 | 27 and 28 | 29 and 30 | 31 and 32 | 33 and 34 | 35 and 36 |
| 37 and 38 | 39 and 40 | 41 and 42 | 43 and 44 | 45 and 46 | 47 and 48 |
| 49 and 50 | 51 and 52 | 53 and 54 | 55 and 56 | 57 and 58 | 59 and 60 |
| 61 and 62 | 63 and 64 | 65 and 66 | 67 and 68 | 69 and 70 | 71 and 72 |
| 73 and 74 | 75 and 76 | 77 and 78 | 79 and 80 | 81 and 82 | 83 and 84 |
| 85 and 86 | 87 and 88 | 89 and 90 | 91 and 92 | 93 and 94 | 95 and 96 |
| 97 and 98 | 99 and 100 | 101 and 102 | 103 and 104 | 105 and 106 | 107 and 108 |
| 109 and 110 | 111 and 112 | 113 and 114 | 115 and 116 | 117 and 118 | 119 and 120 |
| 121 and 122 | 123 and 124 | 125 and 126 | 127 and 128 | 129 and 130 | 131 and 132 |
| 133 and 134 | 135 and 136 | 137 and 138 | 139 and 140 | 141 and 142 | 143 and 144 |
| 145 and 146 | 147 and 148 | 149 and 150 | 151 and 152 | 153 and 154 | 155 and 156 |
| 157 and 158 | 159 and 160 | 161 and 162 | 163 and 164 | 165 and 166 | 167 and 168 |
| 169 and 170 | 171 and 172 | 173 and 174 | 175 and 176 | 177 and 178 | 179 and 180 |
| 181 and 182 | 183 and 184 | 185 and 186 | 187 and 188 | 189 and 190 | 191 and 192 |
| 193 and 194 | 195 and 196 | 197 and 198 | 199 and 200 | 201 and 202 | 203 and 204 |
| 205 and 206 | 207 and 208 | 209 and 210 | 211 and 212 | 213 and 214 | 215 and 216 |
| 217 and 218 | 219 and 220 | 221 and 222 | 223 and 224 | 225 and 226 | 227 and 228 |
| 229 and 230 | 231 and 232 | 233 and 234 | 235 and 236 | 237 and 238 | 239 and 240 |
| 241 and 242 | 243 and 244 | 245 and 246 | 247 and 248 | 249 and 250 | 251 and 252 |
| 253 and 254 | 255 and 256 | 257 and 258 | 259 and 260 | 261 and 262 | 263 and 264 |
| 265 and 266 | 267 and 268 | 269 and 270 | 271 and 272 | 273 and 274 | 275 and 276 |
| 277 and 278 | 279 and 280 | 281 and 282 | 283 and 284 | 285 and 286 | 287 and 288 |
| 289 and 290 | 291 and 292 | 293 and 294 | 295 and 296 | 297 and 298 | 299 and 300 |
| 301 and 302 | 303 and 304 | 305 and 306 | 307 and 308 | 309 and 310 | 311 and 312 |
| 313 and 314 | 315 and 316 | 317 and 318 | 319 and 320 | 321 and 322 | 323 and 324 |
| 325 and 326 | 327 and 328 | 329 and 330 | 331 and 332 | 333 and 334 | 335 and 336 |

The results from these serial dilution experiments at the three highest dilutions were used to construct assay specific standard curves.

A set of three *Mus musculus* genes were spiked into the master mix of both calibration and experimental chips to test for PCR inhibitors and ensure roughly similar amplification performance.

Negative controls consisted of a complex genomic mixture absent reductive dehalogenases. The mixture was constructed from DNA isolated from the following archaea and bacteria: *Methanococcus maripaludis* 109, *Methanothermococcus thermolithotrophicus* DSM 2095, *Sporomusa ovata* DSM 2662, *Shewanella oneidensis* MR-1, *Geobacter metallireducens* GS-15, *Clostridium sporogenes*, *Sinorhizobium meliloti*, and *Bacteroides thetaiotaomicron*.

Example 3

Assay Specificity Tests:

To validate the selectivity of newly-designed assay primer pairs to distinguish among rdh groups, total DNA was isolated by a POWERSOIL® kit (MoBio Laboratories, Inc, Carlsbad, Calif.) or by methods such as described in Behrens et al., (2008) *Appl. Environ. Microbiol.* 74: 5695-5703 from cultures highly enriched for *Dehalococcoides mccartyi* VS, GT, CBDB1, and *ethenogenes* 195. Samples were prepared at various bulk concentrations varying from 10 to 0.01 ng/µl. These were further diluted in LIGHTCYCLER® 480 SYBR Green I Master Mix (Roche Applied Science, Inc) to final concentrations of 25 to 0.1 pg per well. Additionally, a separate sample was amended with the above-mentioned genomic negative control mixture (50 pg) such that the *Dehalococcoides* DNA represented a minority fraction of total complex DNA mixture in each reaction.

The systems of the disclosure were then examining for consistent amplification of high PID homologs across *Dehalococcoides* isolates, while also measuring the frequency of false positives due to off-target amplifications. It was predicted that primer sets containing three or more cumulative mismatches with a target gene would not amplify efficiently. If it did, it was classified as a false positive. By comparing this expectation with the amplification result, each assay/isolate combination was designated as true-positive, true-negative, false-positive, or false-negative if confirmed by duplicate chip results.

The final rdh PCR suite of primers included multiple pairs for each reference group. Individual assay primer pair results were aggregated in concordance with the recently developed Reductive Dehalogenase Orthologue Group naming system Hug et al., (2013) *Philo. Trans. Roy. Soc. B: Biol. Sci.* 368: 20120322-20120322). Each group presence/absence classification (true-positive, false-positive, false-negative, or true-negative) was determined by the majority result of all assay primer pairs targeting that group. If an equal number of assay primer pairs returned estimates above and below 1 copy per reaction, the group was considered absent.

Example 4

Pore Water Biostimulation:

Pore waters extracted from sampling wells from an Italian industrial site were transferred in an anoxic glove box into nitrogen-filled serum vials. The vials were sparged to remove volatile organic chloroethenes. 1,2-DCA remained in concentrations ranging from 1.5 to 6 mM, reflecting differential contamination at each observation well. 2 mM lactate, acetate, or formate was supplied as an electron donor in replicate vials of each pore water. As a control, a fourth replicate vial received salts in lieu of an electron donor. All vials were amended with a vitamin solution (Table 4).

TABLE 4

| Vitamin Mix (final concentration of each component in the stimulated pore water) | |
|---|---|
| Vitamin B12 | 100 µg/L |
| p-aminobenzoic acid | 80 µg/L |

TABLE 4-continued

Vitamin Mix (final concentration of each component in the stimulated pore water)

| | |
|---|---|
| D(+)-biotin | 20 µg/L |
| Nicotinic acid | 200 µg/L |
| Calcium pantothenate | 100 µg/L |
| Pyridoxine hydrochloride | 300 µg/L |
| Thiamine-HCl × 2H$_2$O | 200 µg/L |

Chemical degradation was measured by gas chromatography at 7, 18 and 23 days. After day 23, DNA was isolated from 8 ml of pore water with the MP SOIL® DNA (MP Biomedicals) bead-beating protocol.

Recovered DNA, ranging in concentration from 0.1 ng to 30 ng/µl, was applied to the nl-qPCR chip containing the validated assay suite of primers shown in Table 2. Gene target estimates ranged from 4×10$^3$ to 4.6×10$^8$ copies per ml pore water. 4×10$^3$ copies per ml pore water was the practical limit of detection given constraints introduced by the DNA isolation method used on-site.

Example 5

Sampling of the Continuous Bioreactor:

Operation and sampling procedure for the Evanite two-liter (EV2L) TCE-degrading continuously-fed reactor has been previously described (Berggren et al., (2013) *Environ. Sci. & Technol.* 47: 1879-1886). Briefly, cells were grown at a mean-cell residence time of 50 days and fed formate as an electron donor. Reactor liquid (50 ml) was spun by centrifuge (8000 RCF) for 30 min with solids transferred to a MOBIO POWERSOIL® bead-beating tube followed by isolation with Phenol:Chloroform:Isoamyl Alcohol saturated with Tris-HCl pH 8.05. The resulting DNA per sample was diluted to 10 ng/µl, corresponding to 25 pg DNA per 100 nL qPCR reaction.

Example 6

Detection of Rare Community Members:

In practice, the limits of detection in environmental samples depend not only on assay quality, but also on the quantity of nucleic acid template and the fraction of target DNA within a mixed community. Assuming modest 20 ng DNA recovered from an environment dominated by bacteria and archaea, a nL-qPCR platform was developed that enabled detection of rdh genes in rare population members that constitute on the order of 10-3 of the total microbial population.

This estimate was based on the following calculations where the volume of DNA applied to a sample mastermix can range from 1-10 µL (¹⁄₄₀th to ⅛th of the total mastermix volume) per sample depending on the demands of the experiment.

| | | |
|---|---|---|
| F | [%] | Minimum Fraction of Community Detectable |
| CpW | [copies] | Copies needed for detection |
| CINPUT | [ng/µl] | Sample Concentration |
| VINPUT | [µL] | Sample Input Volume |
| VMM | [µL] | Master Mix Volume |
| VWELL | [µL] | Reaction Well Volume |
| G | [bp] | Average Bacterial Genome Size |

One can calculate the DNA mass per well by:

$$DNA_{MASSng} = \left(\frac{C_{INPUT}V_{INPUT}}{V_{MIX}}\right)\left(\frac{V_{WELL}}{1}\right)$$

One can convert DNA mass to genomic copies assuming a dsDNA bp=650 Daltons by $$\text{Number of Copies} = \frac{DNA_{MASSng}}{G} * \left(\frac{6.022 * 10^{23}}{10^9 * 650}\right)$$

by substituting from above:

$$\text{Number of Copies} = \left(\frac{C_{INPUT}V_{INPUT}}{V_{MIX}}\right)\left(\frac{V_{WELL}}{1}\right) * \frac{1}{G} * \left(\frac{6.022 * 10^{23}}{10^9 * 650}\right)$$

Assuming 1 to 10 copies of the target organism's DNA are needed for detection we can estimate the minimum fraction of the community detectable.

$$F = \left(\left(\frac{1}{CpW}\right)\left(\frac{C_{INPUT}V_{INPUT}}{V_{MIX}}\right)\left(\frac{V_{WELL}}{1}\right) * \frac{1}{G} * \left(\frac{6.022 * 10^{23}}{10^9 * 650}\right)\right)^{-1}$$

$$F(CpW = 10, V_I = 2, C_{INPUT} = 10, G = 3.5E^6) = 1.5E^{-3}$$

$$F(CpW = 1, V_{INPUT} = 2, C_{INPUT} = 10, G = 3.5E^6) = 1.5E^{-4}$$

(These estimates assume no contaminating eukaryotic or viral DNA which may be considerable in some sample types).

Poisson Noise at Low Copy Numbers:

To investigate the sensitivity of the nl-qPCR assays, each primer pair was tested against a dilution series of linear 500 bp DNA standards. The Ct difference between two replicate reactions increased as the number of starting gene copies per reaction well decreased. Simulation, run using the statistical software environment R, indicated increasing Ct difference should be expected from stochastic processes associated with small-number statistics ("Poisson noise"). In the simulation, it was assumed drawing pairs of observations from an underlying Poisson distribution with varying parameter mean from 1 to 20,000.

FIG. 5 shows the expected Poisson noise and observed difference in replicate Ct of the assays (n=116) at 20,000, 2000, 200, and 20 starting copies per reaction. Because of the observed variability at 20 starting copy numbers, 3-point standard curves were generated with the more concentrated standards (200, 2000, 20000 starting copies). The nature of the errors were examined, defined as the difference between the observed Ct at 20 starting copies and the value predicted by the linear regression from the 3-point calibration ordinary least squares line.

A systematic loss in sensitivity at low copy numbers was not seen. Strong bias in the errors would have suggested diminished assay performance against dilute targets, whereas the relatively unbiased errors observed here suggest the result of stochastic processes (where an over or under estimate are equally likely). Given the random nature of errors, the errors due to Poisson noise could likely be overcome and improved calibration accuracy achieved by increasing the number of technical replicates at low starting copies per reaction.

Because of the observed variability at the dilution of 20 copies per reaction 3-point standard curves were generated with the more concentrated standards (200, 2000, 20000 starting copies). The nature of the errors were examined, defined as the difference between the observed Ct at 20 starting copies and the value predicted by the linear regression from the 3-point calibration, based on ordinary least squares (see FIG. 6). A systematic loss in sensitivity at low copy numbers was not observed. Strong bias in the errors would have suggested diminished assay performance against dilute targets, whereas the relatively unbiased errors observed here suggest the result of stochastic processes (where an over or under estimate are equally likely).

Example 7

Specific Parameters and Programs for Primer Selection:

The "Primer3 www primer tool" (University of Massachusetts Medical School) is software for the design of oligonucleotide PCR primers. The command-line version 2.3.4 of Primer3 was used with the following parameters to design thousands of assay primer pairs for each rdh or hupL reference sequence. By using standard WAFERGEN® validated assays known to perform well within a standard WAFERGEN® thermocycler program, the input parameters of Primer3 were tuned to produce assays with similar predicted thermodynamic binding properties. The parameters used in the control file were:

PRIMER_NUM_RETURN=2500
PRIMER_MIN_TM=59
PRIMER_OPT_TM=60
PRIMER_MAX_TM=61
PRIMER_MIN_SIZE=15
PRIMER_MAX_SIZE=28
PRIMER_NUM_NS_ACCEPTED=1
PRIMER_PRODUCT_SIZE_RANGE=75-200
PRIMER_GC_CLAMP=0
PRIMER_FILE_FLAG=1
PRIMER_EXPLAIN_FLAG=1
PRIMER_TM_FORMULA=1
PRIMER_SALT_CORRECTIONS=1
PRIMER_THERMODYNAMIC_ALIGNMENT=1
PRIMER_SALT_DIVALENT=3
PRIMER_DNTP_CONC=0.6
PRIMER_LIB_AMBIGUITY_CODES_CONSENSUS=0

These parameters produced many high efficiency assays when run at a 60° C. annealing temperature in the ROCHE LIGHTCYCLER® SYBR Green I Master Mix. Use of an alternative master mix or annealing temperatures will necessitate retuning of these parameters to account for the change in PCR reaction conditions.

The freely available Emboss program "fuzznuc" (as described by Rice et al., (2000) EMBOSS: The European Molecular Biology Open Software Suite in *Trends in Genetics* 16: 276-277, incorporated herein by reference in its entirety) was used to perform fuzzy matching between each candidate assay primer pair and the relevant reductive dehalogenase genes. This permitted determination of how many gene sequences were complementary to a given primer.

The fuzznuc pattern file used was:
pat1 <mismatch=4>
forward primer sequence
>pat2 <mismatch=4>
reverse primer sequence This input allowed for match detection of sequences with up to 4 mismatches per primer, and was produced for each candidate assay as follows.

Example 8

Detection of Rare Community Members:

The limits of detection in environmental samples depend not only on assay quality, but also on the quantity of nucleic acid template and the fractional enrichment the target DNA within a mixed community. With about 20 ng DNA recovered from an environment dominated by bacteria and archaea, an nl-qPCR platform was developed that enabled detection of rdh genes in rare population members that constitute on the order of $10^{-3}$ of the total microbial population.

This estimate was based on the following calculations where the volume of DNA applied to a sample mastermix can range from 2-10 µl (0.025 to about 0.125 of the total mastermix volume) per sample depending on the demands of the experiment.

| | | |
|---|---|---|
| F | [%] | Minimum Fraction of Community Detectable |
| CpW | [copies] | Copies needed for detection |
| $C_{INPUT}$ | [ng/µl] | Sample Concentration |
| $V_{INPUT}$ | [µl] | Sample Input Volume |
| $V_{MM}$ | [µl] | Master Mix Volume |
| $V_{WELL}$ | [µl] | Reaction Well Volume |
| G | [bp] | Average Bacterial Genome Size |

The DNA mass per well is given by:

$$DNA_{MASS_{ng}} = \left(\frac{C_{INPUT} V_{INPUT}}{V_{MIX}}\right)\left(\frac{V_{WELL}}{1}\right)$$

and converted to genomic copies, assuming a dsDNA bp=650 Daltons, by $$\text{Number of Copies} = \frac{DNA_{MASS_{ng}}}{G} * \left(\frac{6.022 * 10^{23}}{10^9 * 650}\right)$$

by substituting from above:

$$\text{Number of Copies} = \left(\frac{C_{INPUT} V_{INPUT}}{V_{MIX}}\right)\left(\frac{V_{WELL}}{1}\right) * \frac{1}{G} * \left(\frac{6.022 * 10^{23}}{10^9 * 650}\right)$$

Assuming 1 to 10 copies of the target organism's DNA are needed for detection, the minimum fraction of the community detectable is given by:

$$F = \left(\left(\frac{1}{CpW}\right)\left(\frac{C_{INPUT} V_{INPUT}}{V_{MIX}}\right)\left(\frac{V_{WELL}}{1}\right) * \frac{1}{G} * \left(\frac{6.022 * 10^{23}}{10^9 * 650}\right)\right)^{-1}$$

$F(CpW = 10, V_{INPUT} = 2, C_{INPUT} = 10, G = 3.5E^6) = 1.5E^{-3}$ $F(CpW = 1, V_{INPUT} = 2, C_{INPUT} = 10, G = 3.5E^6) = 1.5E^{-4}$

*These estimates assume no contaminating eukaryotic or viral DNA which may be considerable in some sample types.

Example 9

Calculating Copies Per mL from Counts Per 0.1 μl Reaction Well:

| | | |
|---|---|---|
| $N_{well}$ | | Copies per well estimated from observed Ct and standard curve. |
| $C_{mm}$ | | Copies per μl once diluted into the MasterMix |
| $C_{DNA}$ | | Copies per μl of eluted isolated DNA |
| $C_S$ | | Copies per μl of original water sample |
| $V_{WELL}$ | [μl] | Reaction Well Volume 0.1 μL |
| $V_{MM}$ | [μl] | Total Volume of the Master Mix |
| $V_{INPUT}$ | [μl] | Total volume of DNA applied to the chip |
| $V_{DNA}$ | [μl] | Volume of DNA eluent following DNA isolation protocol (Usually varies between 20 and 100 μl) |
| $V_S$ | [ml] | Volume of original liquid sample (Usually varies between 1 ml-1000 ml) |

The concentration of gene copies in the original sample is related to the concentration in the isolated DNA (assuming 100% DNA isolation efficiency) by:

$$C_S = \left(\frac{V_{DNA}}{V_S}\right) C_{DNA}$$

The concentration of gene copies in the isolated DNA concentrate is related to that in the sample mastermix:

$$C_{DNA} = \left(\frac{V_{MM}}{V_{Input}}\right) C_{MM}$$

The concentration in the master mix is related to the number of copies in each nl-qPCR reaction well:

$$C_{MM} = \frac{N_{well}}{V_{well}}$$

Combining these relations, the copies in the original water sample from the number of copies found in an individual nl-qPCR reaction well is calculated:

$$C_{S,\mu l} = \left(\frac{V_{DNA}}{V_s}\right)\left(\frac{V_{MM}}{V_{input}}\right)\frac{N_{well}}{V_{well}} = \left(\frac{80\,\mu l}{8,000\,\mu l}\right)\left(\frac{80\,\mu l}{2\,\mu l}\right)\frac{N_{well}}{0.1\,\mu l} = 4 N_{well}\left[\frac{1}{\mu l}\right]$$

Converting to copies per mL pore water.

$$C_{S,ml} = 4 N_{well}\left[\frac{1}{\mu l}\right] * \left[\frac{1000\,\mu l}{1\,ml}\right] = 4000\,N_{well}\left[\frac{1}{ml}\right]$$

Example 10

Practical Pore Water Detection Limits:

$4 \times 10^3$ copies per ml pore water was the practical limit of detection given constraints introduced by the DNA isolation method used on-site; however, a strategy to further concentrate isolated DNA could lower the detection limit to 200 copies per ml pore water.

Assuming almost 100% DNA extraction efficiency, the practical detection limit (PDL) can be calculated from the following parameters.

$V_s$ [ml] Vol. of original liquid sample about 0.5 ml to about 1000 ml)

$V_{DNA}$ [μl] Vol. of DNA eluent following Isolation Protocol about 10 to about 100 μl $V_{INPUT}$ [μl] Vol. of DNA applied to the chip (between about 2 to about 10 μl)

$V_{WELL}$ [μl] Vol. qPCR reaction well

MDL [copies] Machine Detection Limit $$PDL = MDL * \left(\frac{V_{DNA}}{V_s}\right) * \left(\frac{V_{MM}}{V_{INPUT}}\right) * \left(\frac{1}{V_{well}}\right) * \left(\frac{1000\,\mu l}{1\,ml}\right) =$$

$$PDL = MDL * \left(\frac{80}{8000}\right) + \left(\frac{80}{2}\right) * \left(\frac{1}{0.1}\right) * \left(\frac{1000\,\mu l}{1\,ml}\right) =$$

4000 copies per ml original sample

If a lower detection limits is required, the following protocol can be employed:

$V_S$ [8 ml]

$V_{DNA}$ [20 μl] from use of a DNA CLEAN & CONCENTRATOR®-5, Qiagen Mini-elute or Rotary Evaporation $V_{CHIP}$ [10 μl] Use all of sample for two replicates MDL [1 copy]

$$PDL = MDL * \left(\frac{20}{8000}\right) * \left(\frac{80}{10}\right) * \left(\frac{1}{0.1}\right) * \left(\frac{1000\,\mu l}{1\,ml}\right) =$$

200 copies per ml original sample

Still lower detection limits can be achieved by filtering a large volume of pore water from which to perform the DNA extraction.

Example 11

Evaluation of Known 16SrRNA Gene Primers for Parallel Use with the rdhA Primer Suite:

Determining the relative stoichiometry among specific functional genes and phylogenetically informative 16S rRNA marker genes is desirable. Designing and validating selective 16S rRNA gene primers is a challenge due to the high level of conservation in the ribosomal gene. Which 16S rRNA qPCR primers for organohalogen-respiring genera would be compatible with the nL-qPCR conditions of the methods of the disclosure were determined.

Table 5 illustrates those primers selected from the literature given the major genera thought to be involved in dehalogenating chloroethenes and chloroethanes. Recommended PCR conditions varied significantly for these primers, but most had an annealing temperature between 55° C. and 63° C. All were tested only at the Wafergen standard nL-qPCR conditions used for the rdh primer validation their performance was evaluated in that context against linear DNA standards of 16S rRNA gene fragments from *Dehalococcoides mccartyi* strain 195, *Geobacter metallireducens*, *Desulfitobacterium hafniense* Y51, *Dehalogenimonas lykanthroporepellens*, and *Dehalobacter* sp. WL. The primers that performed suitably under our standard nL-qPCR conditions are indicated in Table 5.

TABLE 5

Evaluation of known 16S rRNA primers for use with rdhA primer suite

| | Genus | Forward Primer Sequence | Reverse Primer Sequence |
|---|---|---|---|
| 1 | *Dehalobacter* | GTTAGGGAAGAACGGCATCTGT (SEQ ID NO: 337) | CCTCTCCTGTCCTCAAGCC ATA (SEQ ID NO: 338) |
| 2 | *Dehalococcoides/ Dehaligenimonas* | GAGGCAGCAGCAAGGAA (SEQ ID NO: 339) | GGCGGGACACTTAAAGCG (SEQ ID NO: 340) |
| 3 | *Dehalobacter* | GCACAAGCGGTGGAGCATGTGG (SEQ ID NO: 341) | ACAATCCGAACTGAGAACG (SEQ ID NO: 342) |
| 4 | *Dehalobacter* | GATTGACGGTACCTAACGAGG (SEQ ID NO: 343) | TACAGTTTCCAATGCTTTAC GG (SEQ ID NO: 344) |
| 5 | *Dehalococcoides* | GGCGTAAAGTGAGCGTAG (SEQ ID NO: 345) | GACAACCTAGAAAACCGC (SEQ ID NO: 346) |
| 6 | *Dehalococcoides* | GATGAACGCTAGCGGCG (SEQ ID NO: 347) | CAGACCAGCTACCGATCGA A (SEQ ID NO: 348) |
| 7 | *Dehalococcoides* | GAAGTAGTGAACCGAAAGG (SEQ ID NO: 349) | TCTGTCCATTGTAGCGTG (SEQ ID NO: 350) |
| 8 | *Dehalococcoides* | AAGGCGGTTTTCTAGGTTGTCAC (SEQ ID NO: 351) | CTTCATGCATGTCAAAT (SEQ ID NO: 352) |
| 9 | *Dehalogenimonas* | GGTCATCTGATACTGTTGGACTT GA (SEQ ID NO: 353) | ACCCAGTGTTTAGGGCGTG GACTA (SEQ ID NO: 354) |
| 10 | *Desulfitobacterium* | GTACGACGAAGGCCTTCGGGT (SEQ ID NO: 355) | CCCAGGGTTGAGCCCTAGG T (SEQ ID NO: 356) |
| 11 | *Desulfitobacteriam* | GCACAAGCGGTGGAGCATGTGG (SEQ ID NO: 357) | TATCTAGAGTGCTCRACC (SEQ ID NO: 358) |
| 12 | <u>Eub*acteria*</u> | CCTACGGGAGGCAG<u>CAG</u> (SEQ ID NO: 359) | <u>ATTACCGCGG</u>CTGCTGGC (SEQ ID NO: 360) |
| 13 | *Geobacter* | AAGCGTTGTTCGGAWTTAT (SEQ ID NO: 361) | GGCACTGCAGGGGTCAATA (SEQ ID NO: 362) |
| 14 | *Geobacter* | AGGAAGCACCGGCTAACTCC (SEQ ID NO: 363) | TACCCGCRACACCTAGT (SEQ ID NO: 364) |
| 15 | Dehalococcoides | GGGAGTATCGACCCTCTC (SEQ ID NO: 365) | GGATTAGCTCCAGTTCACA CT (SEQ ID NO: 366) |

| | Amplicon (bp) | Primer reference | Rejection Criteria |
|---|---|---|---|
| 1 | 226 | Smits et al., (2004) *Microbiol. Methods* 57: 369-378 | Low Selectivity |
| 2 | 512 | Fagervold et al., (2005) *Appl. Environ. Microbiol.* 71: 8085-8090 | Low Efficiency |
| 3 | 380 | Marzorati et al., (2007) *Appl. Environ. Microbiol.* 73: 2990-2999 | Amplified Negative Control |
| 4 | 169 | Groestern et al., (2006) *Appl. Environ. Microbiol.* 72: 428-436 | Amplified Desulfitobacterium |
| 5 | 181 | Behrens et al., (20008) *Appl. Environ. Microbiol.* 74: 5695-5703 | Poor Efficiency |
| 6 | 265 | Duhamel et al., (2006 FEMS *Microbiol. Ecol.* 58: 538-549 | Low Efficiency |
| 7 | 235 | Schaefer et al., (2009) *Chemosphere* 75: 141-148. S34 | |
| 8 | 278 | Smits et al., (2004) *Microbiol. Methods* 57: 369-378 | |
| 9 | 193 | Yan et al., (2009) *Environ. Microbiol.* 11: 833-843 | Low Efficiency, Amplified Dhc |
| 10 | 224 | Smits et al., (2004) *Microbiol. Methods* 57: 369-378 | |

TABLE 5-continued

Evaluation of known 16S rRNA primers for use with rdhA primer suite

| 11 | 225 | Marzorati et al., (2007) *Appl. Environ. Microbiol.* 73: 2990-2999 | Multi-Product Amplification |
| 12 | 193 | Muyzer et al., (1993) *Appl. Environ. Microbiol.* 59: 695-700 | Inconsistent Amplification |
| 13 | 312 | Cummings et al., (2003) *Microb. Ecol.* 46: 257-269 | |
| 14 | 346 | Bond et al., (2002) *Science* 295: 483-485 | Low Efficiency |
| 15 | 446 | Hendrickson et al., (2002) *Appl. Environ. Microbiol.* 68: | Low Efficiency |

Example 12

Quantification of Genes from nL1qPCR Results-Method of Estimating Starting Copies:

Quantifying genes by nL-qPCR was performed by methods of quantification similar to those used for μL-PCR. A standard curve was produced for each assay by use of synthesized linear DNA standards (Integrated DNA Technology). In this study, assays were run over a serial dilution range of 20,000, 2,000, and 200 starting copies per reaction. Data from each set of standards was duplicated on two separate chips. A cycle number (Ct) is determined at which the amplification passes through a critical threshold value determined by the default parameter of the Wafergen qPCR gene expression analysis software. A linear regression best-fit line was constructed based on Ct values and log 10 (input concentrations), determining an assay specific slope and intercept parameter $$Ct = slope * \log 10[DNA\ copies] + intercept$$

For each assay the PCR efficiency is directly related to the slope parameter and was calculated as follows:

$$efficiency = 10^{\left(-\frac{1}{slope}\right)} - 1$$

For each experimental sample a Ct value was related to an estimate of starting copies per reaction as follows:

$$[DNA\ copies] = 10^{ct-intercept/slope}$$

Example 13

Quantitative estimates of starting gene copies are frequently made by the inclusion of standard DNA fragments at a known concentration run alongside experimental samples. Running a calibration with every plate or chip is desirable since it can account for chip-specific or master-mix variability, which might otherwise bias the results. However, when running a few samples against many different assays (e.g. 20 samples×384 assays), dedicating chip capacity to calibration can greatly increase the cost of a project. For instance, conducting a 3-point calibration curve in duplicate would consume 25% the capacity of 24 sample×216 assay chip. A 5-point calibration curve would consume 40% of the chip capacity. Moreover if some assays target multiple templates, these templates must be run as separate calibration samples. As a result, the number of samples that must be dedicated to calibration can quickly consume the full capacity of a single chip.

For the assays of the disclosure, for low sample:assay chip ratios, it can be advantageous to use previously generated standard curves made with the same lot of master-mix and rely on an exogenous DNA spike-in to ensure similar performance across-multiple chips. Some known nL-qPCR studies abandon the use of standards and adopt a statistical approach to Ct interpretation. Even when using the standard curve library approach, as used in developing the assays of the disclosure, the lack of standard curves on each chip potentially reduced the absolute accuracy of nL estimates compared with traditional lower throughput uL-qPCR. All results were duplicated on at least two separate chips and found only modest chip-to-chip variation. However, if a new lot of master mix (polymerase enzyme and buffer) was used, new standard curves would be generated as reagent quality could contribute to significant bias. Accordingly, where absolute accuracy is paramount, it can be advantageous to first screen samples at a low samples:assays format and then select a subset of assays to be run against the same samples and a comprehensive set of calibration standards at a high sample:assay format (e.g. 96:54 samples:assays).

We claim:

1. A method for identifying a dechlorinating microbial organism, or a plurality of said microbial organisms, in a sample comprising:
   (a) obtaining a sample suspected of having a population of at least one dechlorinating microbial strain having at least one species of a reductive dehalogenase enzyme;
   (b) isolating nucleic acid from the sample;
   (c) applying the isolated nucleic acid to a microfluidic device configured for quantitative real-time PCR and comprising a panel of reductive dehalogenase (rdh)-specific PCR primer pairs selected to allow amplification of a specific target nucleotide sequence under a common PCR protocol, said panel comprising at least five reductive dehalogenase (rdh)-specific PCR primer pairs selected from the group consisting of SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318 319 and 320, 321 and 322, 323 and 324, 325 and 326, 327 and 328, 329 and 330, 331 and 332, 333 and 334, and 335 and 336;
   (d) performing quantitative real-time PCR on the isolated nucleic acid in the microfluidic device with each rdh-specific PCR primer pair of said panel and under conditions wherein the presence of a microbial reductive dehalogenase (rdh)-related nucleic acid sequence results in at least one detectable amplicon encoding a region of a reductive dehalogenase (rdh);
   (e) detecting the at least one amplicon of step (d);

(f) identifying the reductive dehalogenase enzyme encoded by the at least one amplicon; and (g) identifying the dechlorinating microbial strain or strains in the sample of step (a) that has at least one reductive dehalogenase enzyme.

2. The method of claim 1, wherein the sample reacts with each primer pair in a total reaction volume of between about 3 nanoliters and about 500 nanoliters.

3. The method of claim 1, wherein at least one primer of each primer pair has a detectable label attached thereto.

4. The method of claim 3, wherein the detectable label is a fluorescent dye.

5. The method of claim 1, wherein the method further comprises the step of quantitatively identifying the population of dechlorinating microbial strains in the sample of step (a) that have a reductive dehalogenase enzyme.

6. The method of claim 1, wherein the method further comprises the step of classifying the identified reductive dehalogenase enzyme(s) encoded by the at least one amplified PCR product according to their respective reductive dehalogenase (rdh) orthologous groups.

7. The method of claim 1, wherein the sample is obtained from a location suspected of having at least one dechlorinating microbial strain having a reductive dehalogenase (rdh) enzyme.

8. The method of claim 1, wherein the method further comprises the step of obtaining the aqueous sample from a non-aqueous sample.

9. The method of claim 1, wherein the panel of reductive dehalogenase (rdh)-specific PCR primer pairs consists essentially of at least five of the PCR primer pairs SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318, 319 and 320, 321 and 322, 323 and 324, 325 and 326, 327 and 328, 329 and 330, 331 and 332, 333 and 334, and 335 and 336.

10. The method of claim 1, wherein the panel of reductive dehalogenase (rdh)-specific PCR primer pairs consists of at least five of the PCR primer pairs SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318, 319 and 320, 321 and 322, 323 and 324, 325 and 326, 327 and 328, 329 and 330, 331 and 332, 333 and 334, and 335 and 336.

11. A microfluidic nanoliter quantitative PCR device configured for a plurality of quantitative real-time PCR reactions and comprising a panel of reductive dehalogenase (rdh)-specific PCR primer pairs, wherein the panel of reductive dehalogenase (rdh)-specific PCR primer pairs comprises at least five of the PCR primer pairs SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318, 319 and 320, 321 and 322, 323 and 324, 325 and 326, 327 and 328, 329 and 330, 331 and 332, 333 and 334, and 335 and 336.

12. The microfluidic device of claim 11, wherein the panel of reductive dehalogenase (rdh)-specific PCR primer pairs consists essentially of at least five of the PCR primer pairs SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318, 319 and 320, 321 and 322, 323 and 324, 325 and 326, 327 and 328, 329 and 330, 331 and 332, 333 and 334, and 335 and 336.

13. The microfluidic device of claim 11, wherein the panel of reductive dehalogenase (rdh)-specific PCR primer pairs consists of at least five of the PCR primer pairs SEQ ID NOs: 1 and 2, 3 and 4, 5 and 6, 7 and 8, 9 and 10, 11 and 12, 13 and 14, 15 and 16, 17 and 18, 19 and 20, 21 and 22, 23 and 24, 25 and 26, 27 and 28, 29 and 30, 31 and 32, 33 and 34, 35 and 36, 37 and 38, 39 and 40, 41 and 42, 43 and 44, 45 and 46, 47 and 48, 49 and 50, 51 and 52, 53 and 54, 55 and 56, 57 and 58, 59 and 60, 61 and 62, 63 and 64, 65 and 66, 67 and 68, 69 and 70, 71 and 72, 73 and 74, 75 and 76, 77 and 78, 79 and 80, 81 and 82, 83 and 84, 85 and 86, 87 and 88, 89 and 90, 91 and 92, 93 and 94, 95 and 96, 97 and 98, 99 and 100, 101 and 102, 103 and 104, 105 and 106, 107 and 108, 109 and 110, 111 and 112, 113 and 114, 115 and 116, 117 and 118, 119 and 120, 121 and 122, 123 and 124, 125 and 126, 127 and 128, 129 and 130, 131 and 132, 133 and 134, 135 and 136, 137 and 138, 139 and 140, 141 and 142, 143 and 144, 145 and 146, 147 and 148, 149 and 150, 151 and 152, 153 and 154, 155 and 156, 157 and 158, 159 and 160, 161 and 162, 163 and 164, 165 and 166, 167 and 168, 169 and 170, 171 and 172, 173 and 174, 175 and 176, 177 and 178, 179 and 180, 181 and 182, 183 and 184, 185 and 186, 187 and 188, 189 and 190, 191 and 192, 193 and 194, 195 and 196, 197 and 198, 199 and 200, 201 and 202, 203 and 204, 205 and 206, 207 and 208, 209 and 210, 211 and 212, 213 and 214, 215 and 216, 217 and 218, 219 and 220, 221 and 222, 223 and 224, 225 and 226, 227 and 228, 229 and 230, 231 and 232, 233 and 234, 235 and 236, 237 and 238, 239 and 240, 241 and 242, 243 and 244, 245 and 246, 247 and 248, 249 and 250, 251 and 252, 253 and 254, 255 and 256, 257 and 258, 259 and 260, 261 and 262, 263 and 264, 265 and 266, 267 and 268, 269 and 270, 271 and 272, 273 and 274, 275 and 276, 277 and 278, 279 and 280, 281 and 282, 283 and 284, 285 and 286, 287 and 288, 289 and 290, 291 and 292, 293 and 294, 295 and 296, 297 and 298, 299 and 300, 301 and 302, 303 and 304, 305 and 306, 307 and 308, 309 and 310, 311 and 312, 313 and 314, 315 and 316, 317 and 318, 319 and 320, 321 and 322, 323 and 324, 325 and 326, 327 and 328, 329 and 330, 331 and 332, 333 and 334, and 335 and 336.

* * * * *